United States Patent
Wan et al.

(10) Patent No.: US 10,907,172 B2
(45) Date of Patent: Feb. 2, 2021

(54) EXPRESSION OF TRANSCRIPTION REGULATORS THAT PROVIDE HEAT TOLERANCE

(75) Inventors: Jiangxin Wan, Bath (CA); Yafan Huang, Bath (CA)

(73) Assignee: Performance Plants, Inc., Kingston (CA)

( * ) Notice: Subject to any disclaimer, the term of this patent is extended or adjusted under 35 U.S.C. 154(b) by 502 days.

(21) Appl. No.: 13/381,202

(22) PCT Filed: Jun. 30, 2010

(86) PCT No.: PCT/IB2010/001766
§ 371 (c)(1),
(2), (4) Date: Dec. 28, 2011

(87) PCT Pub. No.: WO2011/001286
PCT Pub. Date: Jan. 6, 2011

(65) Prior Publication Data
US 2012/0110698 A1    May 3, 2012

Related U.S. Application Data

(60) Provisional application No. 61/221,813, filed on Jun. 30, 2009.

(51) Int. Cl.
*C12N 15/82*    (2006.01)

(52) U.S. Cl.
CPC ................ *C12N 15/8273* (2013.01)

(58) Field of Classification Search
None
See application file for complete search history.

(56) References Cited

U.S. PATENT DOCUMENTS

2006/0041961 A1* 2/2006 Abad ................... C07K 14/415
                                                                 800/289
2007/0033671 A1* 2/2007 Jiang et al. ................... 800/278

FOREIGN PATENT DOCUMENTS

WO    WO-2007113237 A2    10/2007
WO    WO-09027824 A2    3/2009

OTHER PUBLICATIONS

Wang et al. Iron-deficiency-mediated stress regulation of four subgroup 1b BHLH genes in *Arabidopsis thaliana*. Planta. 2007. 226: 897-908.*
Wang et al. Iron-definiciency-mediated stress regulation of four subgroup 1b BHLH genes in *Arabidopsis thaliana*. Planta. 2007. 226: 897-908.*
Yuan et al. FIT interacts with AtbHLH38 and AtbHLH39 in regulating iron uptake gene expression for iron homeostasis in *Arabidopsis*. Cell Research. 2008. 18: 385-397.*
Jakoby et al. FRU (BHLH029) is required for induction of iron mobilization genes in *Arabidopsis thaliana*. FEBS Letters. 2004. 577: 528-534.*
Rosso et al. An *Arabidopsis thaliana* T-DNA mutagenized population (GABI-Kat) for flanking sequence tag-based reverse genetics. Plant Molecular Biology. 2003. 53: 247-259.*
Feller et al. Evolutionary and comparative analysis of MYB and bHLH plant transcription factors. The Plant Journal. 2011. 66: 94-116.*
Zhu. Plant salt tolerance. Trends in Plant Science. 2001. 6(2): 66-71.*
Bailey et al "Update on the Basic Helix-Loop-Helix Transcription Factor Gene Family in *Arabidopsis thaliana*." Plant Cell. 15.11(2003):2497-2501.
Birnbaum et al. "A Gene Expression Map of the *Arabidopsis* Root." Science. 302(2003):1956-1960.
Brownlie et al. "The Crystal Structure of an Intact Human Max-DNA Complex: New Insights Into Mechanisms of Transcriptional Control." Structure. 5.4(1997):509-520.
Buckhout et al. "Early Iron-Deficiency-Induced Transcriptional Changes in *Arabidopsis* Roots as Revealed by Microarray Analyses." BMG Genomics. 10(2009):147.
GenBank Accession No. DV488230, retrieved Nov. 16, 2012.
GenBank Accession No. DV488393, retrieved Nov. 16, 2012.
Jin et al. "Multifunctionality and Diversity Within the Plant MYB-Gene Family." Plant Mol. Biol. 41(1999):577-585.
Kang et al. "Target Genes for OBP3, a Dof Transcription Factor, Include Novel Basic Helix-Loop-Helix Domain Proteins Inducible by Salicylic Acid." Plant J. 35(2003):362-372.
Kirik et al. "Ectopic Expression of a Novel MYB Gene Modifies the Architecture of the *Arabdiposis* Inflorescence." Plant. J. 13.6(1998):729-742.
Kirik et al. "Two Novel MYB Homologues With Changed Expression in Late Embryogenesis-Defective *Arabdiposis* Mutants." Plant Mol. Biol. 37(1998):819-827.
Kranz et al. "Towards Functional Characterisation of the Members of the R2R3-MYB Gene Family From *Arabidopsis thaliana*." Plant J. 16.2(1998):263-276.
Ling et al. "The Tomato fer Gene Encoding a bHLH Protein Controls Iron-Uptake Responses in Roots." PNAS. 99.21(2002):13938-13943.
Martinez-Garcia et al. "Direct Targeting of Light Signals to a Promoter-Element-Bound Transcription Factor." Science. 288. 5(2000):859-863.
Meissner et al. "Functional Search in a Large Transcription Factor Gene Family in *Arabidopsis*: Assessing the Potential of Reverse Genetics to Identify Insertional Mutations in R2R3 MYB Genes." Plant Cell. 11(1999):1827-1840.

(Continued)

*Primary Examiner* — Ashley K Buran
(74) *Attorney, Agent, or Firm* — Cooley LLP; Chen Chen; Cynthia Kozakiewicz

(57) ABSTRACT

The invention relates to methods of producing a desired phenotype in a plant by manipulation of gene expression within the plant. The method relates to means to increase expression level of a bHLH subgroup 1b gene expression or activity, wherein a desired phenotype such as increased heat tolerance relative to a wild type control plant following heat stress results in reduced flower abortion and increased yield. Included are plants produced by said methods. The invention also relates to nucleic acid sequences and constructs useful such methods and methods of generating and isolating plants having increased expression of a bHLH subgroup 1b expression or activity.

12 Claims, 1 Drawing Sheet

Specification includes a Sequence Listing.

(56) References Cited

OTHER PUBLICATIONS

Ogo et al. "Isolation and Characterization of IRO2, a Novel Iron-Regulated bHLH Transcription Factor in Graminaceous Plants." *J. Exp. Bot.* 57.11(2006):2867-2878.
Oppenheimer et al. "A myb Gene Required for Leaf Trichome Differentiation in *Arabidopsis* is Expressed in Stipules." *Cell.* 67(1991):483-493.
Paz-Ares et al. "The Regulatory ci Locus of *Zea mays* Encodes a Protein With Homology to myb Proto-Oncogene Products and With Structural Similarities to Transcriptional Activators." *EMBO J.* 6.12(1987):3553-3558.
Ramsay et al. "MYB-bHLH-WD40 Protein Complex and the Evolution of Cellular Diversity." *Trends Plant Sci.* 10.2(2005):63-70.
Ramsay et al. "Two Basic-Helix-Loop-Helix Genes (MYC-146 and GL3) From *Arabidopsis* can Activate Anthocyanin Biosynthesis in a White-Flowered *Matthiola incana* Mutant." *Plant Mol. Biol.* 52.3(2003):679-688.
Schmid et al. "A Gene Expression Map of *Arabidopsis thaliana* Development." *Nat. Genet.* 37.5(2005):501-506.
Schmitz et al. "The Tomato Blind Gene Encodes a MYB Transcription Factor That Controls the Formation of Lateral Meristems." *PNAS.* 99.2(2002):1064-1069.
Stracke et al. "The R2R3-MYB Gene Family in *Arabidopsis thaliana*." *Curr. Opin. Plant Biol.* 4.5(2001):447-456.
TAIR Gene Model No. AT2G41240, retrieved Nov. 9, 2012.
TAIR Gene Model No. AT2G44790, retrieved Nov. 9, 2012.
TAIR Gene Model No. AT3G56970, retrieved Nov. 9, 2012.
TAIR Gene Model No. AT3G56980, retrieved Nov. 9, 2012.
TAIR Gene Model No. AT5G04150, retrieved Nov. 9, 2012.
TAIR Gene Model No. AT5G52640, retrieved Nov. 9, 2012.
TAIR Gene Model No. AT5G65790, retrieved Nov. 9, 2012.
Toledo-Ortiz et al. "The *Arabidopsis* Basic/Helix-Loop-Helix Transcription Factor Family." *Plant Cell.* 15.8(2003):1749-1770.
Tominaga et al. "Functional Analysis of the Epidermal-Specific MYB Genes CAPRICE and WEREWOLF in *Arabidopsis.*" *Plant Cell.* 19.7(2007):2264-2277.
Van De Mortel et al. "Expression Differences for Genes Involved in Lignin, Glutathione and Sulphate Metabolism in Response to Cadmium in *Arabidopsis thalian* and the Related Zn/Cd-hyperaccumulator *Thlaspi caerulescens.*" *Plant Cell Environ.* 31.3(2008):301-324.
Vorwieger et al. "Iron Assimilation and Transcription Factor Controlled Synthesis of Riboflavin in Plants." *Planta.* 226.1(2007):147-158.
Yanhui et al. "The MYB Transcription Factor Superfamily of *Arabidopsis*: Expression Analysis and Phylogenetic Comparison With the Rice MYB Family." *Plant Mol. Biol.* 60.1(2006):107-124.
Zhang et al. "A Network of Redundant bHLH Proteins Functions in all TTG1-Dependent Pathways of *Arabidopsis.*" *Development.* 130(2003):4859-4869.
Heim et al. "The Basic Helix-Loop-Helix Transcription Factor Family in Plants: A Genome-Wide Study of Protein Structure and Functional Diversity." *Mol. Biol. Evol.* 20.5(2003) 735-747.
Wang et al. "Iron Deficiency-mediated Stress Regulation of Four Subgroup Ib BHLH Genes in *Arabidopsis Thaliana.*" *Planta* 226(2007): 897-908.
Yuan et al. "FIT Interacts with AtbHLH38 and AtbHLH39 in Regulating Iron Uptake Gene Expression for Iron Homeostasis in *Arabidopsis.*" *Cell Research* 18(2008):385-397.
Chinnusamy, V. et al. "ICE1: a regulator of cold-induced transcriptome and freezing tolerance in *Arabidopsis*," *Genes Dev.*, vol. 17, No. 8, p. 1043-1054 (2003).
Wang, Y.-J. et al. "A rice transcription factor OsbHLH1 is involved in cold stress response," *Theor Appl Genet.*, vol. 107, No. 8, p. 1402-1409 (2003).

\* cited by examiner

ClustalW alignment of AtbHLH proteins

```
AtbHLH39    -MCALVPPLFPNFGWPSTGEYDSYYLAGDILNNGGFLDFPVPEETYGAVTAVTQHQNSFG
AtbHLH38    -MCALVPSFFTNFGWPSTNQYESYYGAGDNLNNGTFLELTVP-QTY----EVTHHQNSLG
AtbHLH100   -MCALVPPLYPNFGWPCG--DHSFYETDDVSN--TFLDFPLP-------DLTVTHEN---
AtbHLH101   MEYPWLQSQVHSFSPTLHFPSFLHPLDDSKSHNINLHHMSLS---------HSNNTNSNN
             . :    .*. .        .  .. :   : .:.:.             : *

AtbHLH39    VSVSSEGN-EIDNNPVVVKKLNHNASERDRRRKINSLFSSLRSCLPASGQSKKLSIPATV
AtbHLH38    VSVSSEGN-EIDNNPVVVKKLNHNASERDRRKKINTLFSSLRSCLPASDQSKKLSIPETV
AtbHLH100   --VSSENNRTLLDNPVVMKKLNHNASERERRKKINTMFSSLRSCLPPTNQTKKLSVSATV
AtbHLH101   NNYQEEDR----GAVVLEKKLNHNASERDRRRKLNALYSSLRALLPLSDQKRKLSIPMTV
              ..*..      . *: **********:**:*:*::****: ** :.*.:***:. **

AtbHLH39    SRSLKYIPELQEQVKKLIKKKEELLVQISGQRNTECYVK--QPPKAVANYISTVSATRLG
AtbHLH38    SKSLKYIPELQQQVKRLIQKKEEILVRVSGQRDFELYDK--QQPKAVASYLSTVSATRLG
AtbHLH100   SQALKYIPELQEQVKKLMKKKEELSFQISGQRDLVYTDQNSKSEEGVTSYASTVSSTRLS
AtbHLH101   ARVVKYIPEQKQELQRLSRRKEELLKRISRKTHQEQLRNKAMMDSIDSSSSQRIAANWLT
             :: :***** ::::::* ::***:   ::* : .    :     . :. . :::. *

AtbHLH39    DNEVMVQISSSKIHNFSISNVLSGLEEDRFVLVDMSSSRSQGERLFYTLHLQVEKIENYK
AtbHLH38    DNEVMVQVSSSKIHNFSISNVLGGIEEDGFVLVDVSSSRSQGERLFYTLHLQVENMDDYK
AtbHLH100   ETEVMVQISSLQTEKCSFGNVLSGVEEDGLVLVGASSSRSHGERLFYSMHLQIK---NGQ
AtbHLH101   DTEIAVQIATSKWT--SVSDMLLRLEENGLNVISVSSSVSSTARIFYTLHLQMRG--DCK
             :.*: **::: :     *..:* :**: : ::. *** *   *:**::***:.   : :

AtbHLH39    LNCEELSQRMLYLYEECGNSYI 258  (SEQ ID NO: 122)
AtbHLH38    INCEELSERMLYLYEKCENSFN 253  (SEQ ID NO: 123)
AtbHLH100   VNSEELGDRLLYLYEKCGHSFT 242  (SEQ ID NO: 124)
AtbHLH101   VRLEELINGMLLGLRQS----- 240  (SEQ ID NO: 125)
            :. *** : :*   .:.
```

EXPRESSION OF TRANSCRIPTION REGULATORS THAT PROVIDE HEAT TOLERANCE

RELATED APPLICATIONS

This application is a national stage application, filed under 35 U.S.C. § 371, of International Application No. PCT/IB2010/001766 filed Jun. 30, 2010, which claims priority to U.S. Provisional Application Ser. No. 61/221,813, filed Jun. 30, 2009, the contents of which are hereby incorporated by reference in its entirety.

INCORPORATION BY REFERENCE

The contents of the text file named "22542018001WOST25.txt", which was created on Jun. 30, 2010 and is 157 KB in size, are hereby incorporated by reference in their entirety.

REFERENCE TO RELATED APPLICATIONS

This application claims priority to U.S. Provisional Application Ser. No. 61/221,813, filed Jun. 30, 2009, the contents of which are hereby incorporated by reference in its entirety.

FIELD OF THE INVENTION

The invention is in the field of plant molecular biology and relates to transgenic plants having novel phenotypes, methods of producing such plants and polynucleotides and polypeptides useful in such methods. More specifically, the invention relates to expression of a transcriptional regulator and transgenic plants having increased activity of the transcriptional regulator to produce a plant having a beneficial phenotype.

BACKGROUND OF THE INVENTION

Environmental stresses are responsible for significant yield increase in agricultural crops. The relationship between climate variation and production of corn and soybean throughout the United States for the period 1982-1998 was studied (Lobell and Asner, 2003) and found that even gradual temperature changes have a measurable impact on crop yield. In corn and soybean it has been estimated that yield is reduced by 17% per degree as the growth temperature rises above the season optimum. Both monocots and dicots are sensitive to heat stress, particularly during flowering and seed development which translates into a significant impact on seed yield (Young et al., 2004; Sato et al., 2002; Angadi et al., 2000; Carlson, 1990; Wahid, A., et al. 2007). In the field, heat stress is often accompanied with other environmental stresses as drought which further adds to the burden of plant productivity. Heat stress can have a myriad of cellular effects on plants such as, altered membrane fluidity and permeability, protein aggregation and protein denaturation, the resulting cellular damage may result in deleterious changes in plant growth and development which impacts the ability to survive. It has been suggested that plants possess an inherent ability for basal and acquired thermotolerance and that a common heat response mechanisms is present in diverse plant species (Kapoor et al., 1990; Vierling, 1991; Flahaut et al., 1996; Burke et al., 2000; Hong and Vieling, 2000; Massie et al., 2003; Larkindale et al., 2005). A number of studies have been conducted to identify and characterize genes and pathways that are involved in plant thermotolerance. For example, heat shock transcription factors (HSF) and heat shock proteins (HSP) have received much attention to elucidate the roles and effects of these genes in response to heat stress as have plant growth hormones such as abscisic acid and ethylene. It is unclear how plants sense heat however, it is apparent that multiple signaling pathways and cellular components are involved (Larkindale et al. 2005, Plant Physiol. 138:882-897) and that cross talk of signaling pathways exists between environmental and nutritional stresses such as, heat shock stress, water stress/drought, cold stress, oxidative stress and heavy metal stress.

Transcription factors are DNA binding proteins that interact with specific promoter or enhancer sequences and alter the gene expression of the associated gene. Where the specific sequence that binds the transcription factor is associated with a suite of genes whole pathways can be coordinately regulated with various component genes being simultaneously up-regulated or down-regulated. A transcription factors may coordinately alter a suite of genes in response to a stimulus such as an environmental stress, nutritional status or pathogen attack, for example, or can be a component of a signaling pathway, such as a hormone signaling pathway for example. Transcription factors posses a modular structure and are classified primarily on the basis of the DNA binding domain. Some transcriptional regulators are participants in multiple signal cascades. The pathway and downstream genes regulated may vary depending on the presence or absence of other regulators and pathway components. The transcriptional regulators interact as a network whereby the outcome is dependent on a multitude of interacting factors.

Transcriptional activation is primarily mediated through transcription factors that interact with enhancer and promoter elements. Binding of transcription factors to such DNA elements constitutes a crucial step in transcriptional initiation. Each transcription factor binds to its specific binding sequence in a promoter and activates expression of the linked coding region through interactions with coactivators and/or proteins that are a part of the transcription complex.

The transcription factor bHLH39 is a member of one of the largest families of transcription factors in *Arabidopsis thaliana* comprised of as many as 162 proteins (Heim et al., 2003, Toledo-Ortiz et al., 2003, Bailey et al., 2003). This family of proteins is distinguished from other transcription factors by its basic helix-loop-helix domain (bHLH). Studies have shown the basic region to be critical for DNA-binding, while the hydrophobic helix-loop-helix region is required for homodimer and heterodimer formation. bHLH proteins can have multiple binding partners, and consequently modulate the expression level of a different subset genes depending on its current partner (Zhang et al., 2003). Functional studies have implicated bHLH proteins in a range of cellular processes such as root epidermal cell fate determination (Tominaga, R., et al, 2007), anthocyanin production (Ramsay et al., 2003), and light signaling (Martinez-Garica et al., 2000) and iron uptake (Ling et al., 2002).

The basic region of bHLH proteins, consisting of approximately 15-17 residues, is responsible for binding to cis elements in promoters of target genes. Seventy-five percent of all *Arabidopsis* bHLH proteins are predicted to bind to the core motif known as the E-box (5'CANNTG-3') (Toledo-Ortiz et al., 2003). Specificity for the E-box can be predicted according to the presence of two critical residues, glutamic acid-85 and arginine-88. bHLH39, and its three closest *Arabidopsis* homologues, bhLH38, bHLH100, and bHLH101 all contain the critical glutamic acid and arginine, and therefore are predicted to bind to this motif. The type of E-box binding can be further divided according to the binding preference of two central nucleotides. bHLH39 is predicted to bind to the G-box motif CACGTG according to the presence of two residues, arginine-89 and histadine-81. Arginine-89 and Histadine-81 are responsible for contacting the two central "CG" nucleotides in the G-box and stabilizing the interacting. These two critical residues are also found in the three other *Arabidopsis* bHLH39 homologues. The four critical residues are conserved in all 95 homologues except in two cases, the *Cicer arietinum* homologue has an arginine in place of the histadine-81, and a *Vitis vinifera* homologue has a valine substituted for the glutamic acid-85 (FIG. 1).

Further evidence supporting the binding specificity of bHLH39 comes from reports of the rice ortholog OsIRO2 which binds to 5'-CACGTGG-3' (Ogo et al., 2006). As is the case with OsIRO2, residues outside of the core binding motif most likely also affect binding specificity.

The bHLH proteins bind as dimers to their DNA targets, and binding partner specificity is coded in the Helix-loop-helix domain. Evidence from the crystal structure of an intact human Max-DNA complex showed residue leucine 99 to be critical for dimer formation (Brownlie et al, 1997). This residue is conserved across all bHLH39 homologues except a *Vitis vinifera* homologue. Other residues that show over 95% conservation across all bHLH39 homologues included Arginine-100, Tyrosine-124, Isoleucine-125, and Proline-126. The requirement for a proline at position 126 appears to be specific to bHLH39, bHLH38, bHLH100, and bHLH101, suggesting this residue is important in facilitating dimerization specificity for this group.

According to structural similarities outside of the DNA-binding domain, bHLH39 is similar to 10 other bHLH proteins, which together form subgroup 1b (Heim et al., 2003). The bHLH39 and its closest *Arabidopsis* homologue, bHLH38, show 79% similarity and are located in tandem on the genome, suggesting a recent evolutionary duplication. Other members of the subgroup 1b include bHLH100 and bHLH101. The percent similarity between AtbHLH39 and three other AtbHLH subgroup 1b members (according to Clustal W alignment) are shown below in Table A.

TABLE A

Percent similarity between AtbHLH39, AtbHLH38, AtbHLH100 and AtbHLH101

|  | AtbHLH39 | AtbHLH38 | AtbHLH100 | AtbHLH101 |
| --- | --- | --- | --- | --- |
| AtbHLH39 | 100 | 79 | 60 | 31 |
| AtbHLH38 |  | 100 | 57 | 32 |
| AtbHLH100 |  |  | 100 | 29% |
| AtbHLH101 |  |  |  | 100 |

Both bHLH39 and bHLH38 were identified in a search for downstream targets of a DNA binding with one finger (Dof) transcription factor, ocs-element binding factor (OBP3) which is inducible by salicylic acid. In this case bHLH39 was named ORG3 and bHLH38 was named ORG2. The bHLH39 and bHLH38 were shown to have co-regulated and enhanced expression in OBP3 overexpression lines and being down-regulated in OBF3 loss-of-function lines (Kang et al., 2003). Subsequently, bHLH39 and bHLH38 were shown to be responsive to iron deficiency-mediated stress, along with their two closest homologues in bHLH subgroup 1b, bHLH100, and bHLH101. The role of bHLH39 and bHLH38 expression in relation to iron deficiency has been studied. A transcriptional regulator FIT (AtbHLH29) has been shown to interact with bHLH28 or bHLH39 to transcriptionally regulate the iron uptake genes FRO2 and IRT1. The overexpression of either AtbHLH38 or AtbHLH39 with FIT was found to alter the expression pattern of FRO2 and IRT1 to constitutive activation and result in iron deficiency tolerance (Yuan, et al., 2008). FRO2, a ferric chelate reductase, is responsible for the increase of iron in the soil, a process required to increase the solubility and bioavailability of iron. The iron is subsequently transported across the membrane by the iron transporter, IRT1. Ectopic expression of either AtbHLH38 or AtbHLH39 protein under the control of the 35S promoter in tobacco plants leads to the synthesis and excretion of riboflavin, a known defense mechanism to iron deficient conditions (Vorwieger et al., 2007).

In a transcription regulatory pathway it is common for a first transcription regulator to regulate a second transcription regulator, depending on the network of interacting factors a single transcriptional regulator can play roles in a variety of pathways resulting in a variety of physiological or biochemical outcomes. Such a relationship has been shown between some MYB and some bHLH proteins (Ramsay and Glover, 2005).

The MYB family of transcription factors is composed of at least 198 genes (Yanhui et al. 2006) and has been proposed to have regulatory functions in a wide array of processes ranging from growth and development to defense responses. Plant MYB proteins are classified based on the presence and number of imperfect MYB repeats each composed of about 52 amino acids. The MYB domain forms a helix-turn-helix conformation and represents the DNA binding domain. Three major groups of MYB proteins have been classified as R1R2R3-MYB, R2R3-MYB and MYB-related proteins.

The R2R3-MYB family of proteins in *Arabidopsis* consists of 125 proteins and is characterized by having a R2R3DNA binding domain at their N-terminus (Kranz et al., 1998, and Stracke et al., 2001). These genes are involved in a number of biological processes including mediating hormone actions, secondary metabolism (Paz-Ares et al., 1987), control of cell morphogenesis (Oppenheimer et al., 1991), meristem, floral and seed development (Kirik et al., 1998, Schmitz et al., 2002) and response to various environmental factors (Kranz et al., 1998; Jin and Martin, 1999; Meissner et al, 1999).

SUMMARY OF THE INVENTION

This invention is bases upon the discovery that overexpression of a bHLH subgroup 1b gene transcriptional regulator results in a plant with an altered phenotype such for example increased heat stress tolerance, reduced flower abortion during heat stress, and increased yield relative to a wild type plant.

More specifically, the invention relates to the identification of a bHLH39 or bHLH101 as transcriptional regulators that when overexpressed will produce plants having a heat stress tolerance phenotype.

In one aspect the invention provides a method of producing a transgenic plant, by transforming a plant, a plant tissue culture, or a plant cell with a vector containing a nucleic acid construct that increases the expression or activity of a bHLH subgroup 1b gene to obtain a plant, tissue culture or a plant cell with increased bHLH subgroup 1b expression or activity and growing the plant or regenerating a plant from the plant tissue culture or plant cell, wherein a plant having increased heat stress tolerance relative to a wild type plant is produced.

Accordingly, the present invention provides a method of producing a plant having an improved property, wherein the method includes increasing the expression or activity of an endogenous bHLH subgroup 1b gene, wherein a plant is produced having an advantageous phenotype or improved property. In a particular embodiment, the present invention provides a method for producing plants having increased heat stress tolerance relative to a wild type plant, wherein the method includes include generation of transgenic plants and modification of plants genome using the methods described herein.

Heat stress tolerance refers to the ability of a plant to withstand the debilitating effects of heat which reduces yield of a wild type plant and out perform a wild type plant. As used herein, the term "increased heat stress tolerance" refers to a plant heat stress tolerance is greater as compared to the heat stress tolerance of a corresponding wild-type plant. For example, a plant having increased heat stress tolerance as compared to a wild-type plant may have 5%, 10%, 15%, 20%, 25%, 30%, 40%, 50%, 60% 70%, 75% or greater heat stress tolerance than the corresponding wild-type plant.

The methods of the invention involve increasing the activity of an endogenous or heterologous bHLH subgroup 1b gene by overexpression or promoter modification, wherein a plant is produced having an advantageous phenotype or improved property, such as increased heat stress tolerance relative to a wild type plant. In one aspect, the invention provides a method of producing a plant having increased heat stress tolerance relative to a wild type plant, by introducing into a plant cell a nucleic acid construct that increases the expression or activity of bHLH subgroup 1b gene or protein. For example, a plant having increased heat stress tolerance relative to a wild type plant is produced by a) providing a nucleic acid construct containing a promoter operably linked to a nucleic acid construct that expresses bHLH subgroup 1b activity; b) inserting the nucleic construct into a vector; c) transforming a plant, tissue culture, or a plant cell with the vector to obtain a plant, tissue culture or a plant cell with increased bHLH subgroup 1b activity; d) growing the plant or regenerating a plant from the tissue culture or plant cell, wherein a plant having increased heat stress tolerance relative to a wild type plant is produced. The construct includes a promoter such as a constitutive promoter, a tissue specific promoter or an inducible promoter. Preferably, the tissue specific promoter is a root promoter. A preferable inducible promoter is a heat or drought inducible promoter.

Provided by the invention is a transgenic plant having an advantageous phenotype or improved property such as increased heat stress tolerance, produced by the methods described herein.

In another aspect the invention provides a plant having a non-naturally occurring mutation in a bHLH gene, wherein the plant has increased bHLH subgroup 1b expression or activity and the plant has increased heat stress tolerance relative to a wild type plant. Increased bHLH expression or activity refers to a 2, 3, 4, 5, 6, 7, 8, 9, 10, 15, 20, 25, 30, 40, 50, 60, or 75-fold increase or greater, at the DNA, RNA or protein level of an bHLH gene as compared to wild-type bHLH, or a 2, 3, 4, 5, 6, 7, 8, 9, 10, 15, 20, 25, 30, 40, 50, 60 or 75 fold increase of bHLH activity as compared to wild-type bHLH activity.

A further aspect is a plant having an endogenous bHLH subgroup 1b gene that has an altered promoter sequence operably associated with it. Insertion of enhancer elements or promoter mutations that result in increased gene expression are envisioned by the present invention.

The invention further provides a transgenic seed produced by the transgenic plant(s) of the invention, wherein the seed produces plant having an advantageous phenotype or improved property such as for example, increased heat stress tolerance relative to a wild type plant.

In another embodiment, the invention provides nucleic acids for expression of nucleic acids in a plant cell to produce a transgenic plant having an advantageous phenotype or improved property such as increased heat stress tolerance relative to a wild type plant.

Exemplary sequences encoding a wild type bHLH gene or portion thereof that find use in aspects of the present invention are described in SEQ ID NO's: 1-17, 29-52, 79-83 and 89-97. Exemplary sequences encoding a bHLH39 gene are described in SEQ ID NO's:1-17. Exemplary sequences encoding a bHLH38 gene are described in SEQ ID NO's: 29-52. Exemplary sequences encoding a bHLH101 gene are described in SEQ ID NO's:79-83. Exemplary sequences encoding a bHLH100 gene are described in SEQ ID NO's: 89-97. The invention further provides compositions which contain the nucleic acids of the invention for expression in a plant cell to produce the transgenic plants described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from and are encompassed by the following detailed description and claims.

BRIEF DESCRIPTION OF THE DRAWINGS

FIG. 1 is a ClustalW alignment of various AtbLHL proteins, including AtbHLH39, AtbHLH38, AtbHLH100 and AtbHLH101.

DETAILED DESCRIPTION

The invention is based in part on the discovery of plants having an improved agronomic property, such as for example, increased heat stress tolerance relative to a wild-type control. More specifically, the invention is based upon the discovery that overexpression of a bHLH subgroup 1b transcriptional regulator confers on the plant an improved agronomic property, such as for example, increased heat stress tolerance relative to a wild-type control which can include reduced flower abortion and increased yield The surprising result that overexpression of a bHLH39 subgroup 1b gene is sufficient to confer heat tolerance has been shown. According to microarray and EMSA analysis, bHLH39 is a downstream target of Myb68, another transcription factor which confers heat tolerance when overexpressed. Microarray analysis shows the gene expression of IRT1 is not significantly affected in the 35S-bHLH39, suggesting the heat tolerance conferred by bHLH39 occurs through a separate pathway from the iron deprivation response.

Accordingly the invention provides methods of enhancing (e.g., increasing) the heat stress tolerance of plants by increasing the expression or activity of a bHLH subgroup 1b gene or polypeptide. Methods to increase the expression or activity of a bHLH subgroup 1b gene are known in the art. For example, a plant having increased heat stress tolerance as compared to a wild-type (e.g. control) plant is produced by introducing to a plant cell a nucleic acid construct that increases the expression or activity of a bHLH subgroup 1b gene or polypeptide. The invention also includes the transgenic plants produced by the methods of the invention and the seeds produced by the transgenic plants that produce a plant having increased heat stress tolerance.

For convenience, before further description of the present invention, certain terms employed in the specification, examples and appended claims are defined herein. These definitions should be read in light of the remainder of the disclosure and as understood by a person of ordinary skill in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

A "promoter sequence", or "promoter", means a nucleic acid sequence capable of inducing transcription of an operably linked gene sequence in a plant cell. Promoters include for example (but not limited to) constitutive promoters, tissue specific promoters such as a root promoter, an inducible promoters such as a drought inducible promoter, a heat inducible promoter or an endogenous promoters such as a promoter normally associated with a gene of interest., i.e. a bHLH subgroup 1b gene or cryptic or synthetic promoter sequences which are capable of directing expression of a gene in a plant cell but are not normally associated with an expressible gene.

The term "expression cassette" means a vector construct wherein a gene or nucleic acid sequence is transcribed. Additionally, the expressed mRNA may be translated into a polypeptide.

The terms "expression" or "overexpression" are used interchangeably and mean the expression of a gene such that the transgene or operably linked gene is expressed. The total level of expression in a cell may be elevated relative to a corresponding wild-type cell.

The term "non-naturally occurring mutation" refers to any method that introduces mutations or genetic changes into a plant or plant population. For example, chemical mutagenesis such as ethane methyl sulfonate or methanesulfonic acid ethyl ester, fast neutron mutagenesis, DNA insertional means such as a T-DNA insertion or site directed mutagenesis methods. Also included are methods to induce genetic change such as meganuclease methods that are a particular class of "DNA scissors" they are capable of cutting a chromosome at a specific site in a living cell.

The term "heat stress" refers to a condition where plant growth or productivity is inhibited relative to a plant where heat is not a limiting factor.

The term "heat stress tolerance" refers to the ability of a plant to outperform a wildtype plant under heat stress conditions.

The term "drought stress" refers to a condition where plant growth or productivity is inhibited relative to a plant where water is not limiting. The term "water-stress" is used synonymously and interchangeably with the drought water stress.

The term "drought tolerance" refers to the ability of a plant to outperform a wildtype plant under drought stress conditions or water limited conditions or to use less water during grow and development relative to a wildtype plant.

The term "dry weight" means plant tissue that has been dried to remove the majority of the cellular water and is used synonymously and interchangeably with the term biomass.

The term "null" is defined as a segregated sibling of a transgenic line that has lost the inserted transgene and is therefore used as a control line.

A number of various standard abbreviations have been used throughout the disclosure, such as g, gram; WT, wild-type; DW, dry weight; WUE, water use efficiency; d, day.

The term "bHLH subgroup 1b" means a bHLH39, bHLH38, bHLH100 or bHLH101 transcriptional regulator. In some cases the term bHLH is used to refer to the bHLH subgroup 1b, as appropriate in the context.

The term "bHLH nucleic acid" refers to at least a portion of a bHLH nucleic acid. Similarly the term "bHLH protein" or "bHLH polypeptide" refers to at least a portion thereof. A portion is of at least 21 nucleotides in length with respect to a nucleic acid and a portion of a protein or polypeptide is at least 7 amino acids. The term "AtbHLH" refers to an *Arabidopsis thaliana* bHLH gene, the term "Bn bHLH" refers to a *Brassica napus* bHLH gene.

Determining Homology Between Two or More Sequences

To determine the percent homology between two amino acid sequences or between two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch (1970). Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the coding sequence portion of the DNA sequence shown in SEQ ID NO:1.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Increased Expression of bHLH subgroup 1b Expression and Activity

An aspect of the invention pertains to means and methods of increasing or overexpressing bHLH subgroup 1b gene expression and activity, resulting in an increase of bHLH subgroup 1b protein expression and activity. The term "bHLH expression or activity" embraces both these levels of increase. Increased bHLH expression or activity refers to a 2, 3, 4, 5, 6, 7, 8, 9, 10, 15, 20, 25, 30, 40, 50, 60, or 75-fold increase or greater, at the DNA, RNA or protein level of an bHLH subgroup 1b gene as compared to wild-type bHLH, or a 2, 3, 4, 5, 6, 7, 8, 9, 10, 15, 20, 25, 30, 40, 50, 60 or 75 fold increase of bHLH subgroup 1b protein activity as compared to wild-type bHLH subgroup 1b activity.

Sequences encoding a bHLH subgroup 1b gene or portion thereof that are useful in preparing constructs for bHLH subgroup 1b expression include for example, SEQ ID NO's: 1-17, 29-52, 79-83 and 89-97.

Expression constructs are to provide overexpression either constitutively throughout the plant, or in specific tissues. Alternatively expression can be engineered to occur in response to a temporal, spatial or environmentally regulated stimulus.

Strategies of gene expression will be apparent to the skilled worker including those not discussed here and those developed in the future.

Identification of AtbHLH Homologues

Homologues of Arabidopsis thaliana bHLH subgroup 1b (AtbHLH) were identified using database sequence search tools, such as the Basic Local Alignment Search Tool (BLAST) (Altschul et al., 1990 and Altschul et al., 1997). The tblastn or blastn sequence analysis programs were employed using the BLOSUM-62 scoring matrix (Henikoff and Henikoff, 1992). The output of a BLAST report provides a score that takes into account the alignment of similar or identical residues and any gaps needed in order to align the sequences. The scoring matrix assigns a score for aligning any possible pair of sequences. The P values reflect how many times one expects to see a score occur by chance. Higher scores are preferred and a low threshold P value threshold is preferred. These are the sequence identity criteria. The tblastn sequence analysis program was used to query a polypeptide sequence against six-way translations of sequences in a nucleotide database. Hits with a P value less than −25, preferably less than −70, and more preferably less than −100, were identified as homologous sequences (exemplary selected sequence criteria). The blastn sequence analysis program was used to query a nucleotide sequence against a nucleotide sequence database. In this case too, higher scores were preferred and a preferred threshold P value was less than −13, preferably less than −50, and more preferably less than −100.

A bHLH subgroup 1b gene can be isolated via standard PCR amplification techniques. Use of primers to conserved regions of a bHLH subgroup 1b gene and PCR amplification produces a fragment or full length copy of the desired gene. Template may be DNA, genomic or a cDNA library, or RNA or mRNA for use with reverse transcriptase PCR(RtPCR) techniques. Conserved regions can be identified using sequence comparison tools such as BLAST or CLUSTALW for example. Suitable primers have been used and described elsewhere in this application.

Alternatively, a fragment of a sequence from a bHLH subgroup 1b gene is $^{32}$P-radiolabeled by random priming (Sambrook et al., 1989) and used to screen a plant genomic library (the exemplary test polynucleotides) As an example, total plant DNA from Arabidopsis thaliana, Nicotiana tabacum, Lycopersicon pimpinellifolium, Prunus avium, Prunus cerasus, Cucumis sativus, or Oryza sativa are isolated according to Stockinger et al. (Stockinger et al., 1996). Approximately 2 to 10 μg of each DNA sample are restriction digested, transferred to nylon membrane (Micron Separations, Westboro, Mass.) and hybridized. Hybridization conditions are: 42.degree. C. in 50% formamide, 5×SSC, 20 mM phosphate buffer 1×Denhardt's, 10% dextran sulfate, and 100 μg/ml herring sperm DNA. Four low stringency washes at RT in 2×SSC, 0.05% sodium sarcosyl and 0.02% sodium pyrophosphate are performed prior to high stringency washes at 55° C. in 0.2.times.SSC, 0.05% sodium sarcosyl and 0.01% sodium pyrophosphate. High stringency washes are performed until no counts are detected in the washout according to Walling et al. (Walling et al., 1988). Positive isolates are identified, purified and sequenced. Other methods are available for hybridization, for example the ExpressHyb™ hybridization solution available from Clontech.

bHLH Recombinant Expression Vectors and Host Cells

Another aspect of the invention pertains to vectors, preferably expression vectors, containing a nucleic acid encoding a bHLH subgroup 1b protein, a bHLH subgroup 1b gene or genomic sequence or portions thereof and analogs or homologs thereof. As used herein the term expression vector includes vectors which are designed to provide transcription of the nucleic acid sequence. Transcribed sequences may be designed to express the gene construct to increase the total expression or activity of an endogenous gene activity correlating to the transcribed sequence. The expressed sequence may be an endogenous bHLH subgroup 1b encoding protein or from a heterologous species.

The transcribed nucleic acid may be translated into a polypeptide or protein product. The polypeptide may be a non-full length, mutant or modified variant of the endogenous protein. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication).

Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel (1990). Regulatory sequences include those that direct constitutive expression of a nucleotide sequence in many types of host cell and those that direct expression of the nucleotide sequence only in certain host cells (e.g., tissue-specific regulatory sequences) or inducible promoters (e.g., induced in response to abiotic factors such as environmental conditions, heat, drought, nutrient status or physiological status of the cell or biotic such as pathogen responsive). Examples of suitable promoters include for example constitutive promoters, ABA inducible promoters, tissue specific promoters and abiotic or biotic stress inducible promoters. It will be appreciated by those skilled in the art that the design of the expression vector can depend on such factors as the choice of the host cell to be transformed, the level of expression of protein desired as well as timing and location of expression, etc. The expression vectors of the invention can be introduced into host cells to thereby produce proteins or peptides, including fusion proteins or peptides, encoded by nucleic acids as described herein (e.g., bHLH subgroup 1b proteins, mutant forms of bHLH subgroup 1b proteins, fusion proteins, etc.).

The recombinant expression vectors of the invention can be designed for expression of bHLH subgroup 1b genes, bHLH subgroup 1b proteins, or portions thereof, in prokaryotic or eukaryotic cells. For example, bHLH subgroup 1b genes or bHLH subgroup 1b proteins can be expressed in bacterial cells such as Escherichia coli, insect cells (using baculovirus expression vectors,) yeast cells, plant cells or mammalian cells. Suitable host cells are discussed further in Goeddel (1990). Alternatively, the recombinant expression vector can be transcribed and translated in vitro, for example using T7 promoter regulatory sequences and T7 polymerase.

In one embodiment, a nucleic acid of the invention is expressed in plants cells using a plant expression vector. Examples of plant expression vectors systems include tumor inducing (Ti) plasmid or portion thereof found in *Agrobacterium*, cauliflower mosaic virus (CaMV) DNA and vectors such as pBI121.

For expression in plants, the recombinant expression cassette will contain in addition to the bHLH subgroup 1b nucleic acids, a promoter region that functions in a plant cell, a transcription initiation site (if the coding sequence to transcribed lacks one), and optionally a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector.

Examples of suitable promoters include promoters from plant viruses such as the $^{35}$S promoter from cauliflower mosaic virus (CaMV) (Odell et al., 1985), promoters from genes such as rice actin (McElroy et al., 1990), ubiquitin (Christensen et al., 1992; pEMU (Last et al., 1991), MAS (Velten et al., 1984), maize H3 histone (Lepetit et al., 1992); and Atanassvoa et al., 1992), the 5'- or 3'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, ALS promoter, (WO 96/30530), a synthetic promoter, such as Rsyn7, SCP and UCP promoters, ribulose-1,3-diphosphate carboxylase, fruit-specific promoters, heat shock promoters (HSP 81.1 or HSP18.2), seed-specific promoters, root specific promoters i.e. uclacyanin2 (UCC2, At2g44790) and other transcription initiation regions from various plant genes, for example, including the various opine initiation regions, such as for example, octopine, mannopine, and nopaline. In some cases a promoter associated with the gene of interest (e.g. bHLH) may be used to express a construct targeting the gene of interest, for example the native AtbHLH promoter. Additional regulatory elements that may be connected to a bHLH subgroup 1b encoding nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements of bHLH subgroup 1b gene are known and include, but are not limited to, 3' termination and/or polyadenylation regions such as those of the *Agrobacterium tumefaciens* nopaline synthase (nos) gene (Bevan et al., 1983); the potato proteinase inhibitor II (PINII) gene (Keil et al., 1986) and hereby incorporated by reference); and An et al. (1989); and the CaMV 19S gene (Mogen et al., 1990).

Plant signal sequences, including, but not limited to, signal-peptide encoding DNA/RNA sequences which target proteins to the extracellular matrix of the plant cell (Dratewka-Kos et al., 1989) and the *Nicotiana plumbaginifolia* extension gene (De Loose et al., 1991), or signal peptides which target proteins to the vacuole like the sweet potato sporamin gene (Matsuoka et al., 1991) and the barley lectin gene (Wilkins et al., 1990), or signals which cause proteins to be secreted such as that of PRIb (Lund et al., 1992), or those which target proteins to the plastids such as that of rapeseed enoyl-ACP reductase (Verwoert et al., 1994) are useful in the invention.

In another embodiment, the recombinant expression vector is capable of directing expression of the nucleic acid preferentially in a particular cell type (e.g., tissue-specific regulatory elements are used to express the nucleic acid). Tissue-specific regulatory elements are known in the art. For example, the promoter associated with a coding sequence identified in the TAIR data base as At2g44790 ($P_{4790}$) is a root specific promoter. Especially useful in connection with the nucleic acids of the present invention are expression systems which are operable in plants. These include systems which are under control of a tissue-specific promoter, as well as those which involve promoters that are operable in all plant tissues.

Organ-specific promoters are also well known. For example, the chalcone synthase-A gene (van der Meer et al., 1990) or the dihydroflavonol-4-reductase (dfr) promoter (Elomaa et al., 1998) direct expression in specific floral tissues. Also available are the patatin class I promoter is transcriptionally activated only in the potato tuber and can be used to target gene expression in the tuber (Bevan, 1986). Another potato-specific promoter is the granule-bound starch synthase (GBSS) promoter (Visser et al., 1991).

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, 1986).

The resulting expression system or cassette is ligated into or otherwise constructed to be included in a recombinant vector which is appropriate for plant transformation. The vector may also contain a selectable marker gene by which transformed plant cells can be identified in culture. The marker gene may encode antibiotic resistance. These markers include resistance to G418, hygromycin, bleomycin, kanamycin, and gentamicin. Alternatively the marker gene may encode a herbicide tolerance gene that provides tolerance to glufosinate or glyphosate type herbicides. After transforming the plant cells, those cells having the vector will be identified by their ability to grow on a medium containing the particular antibiotic or herbicide. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

A number of cell types may act as suitable host cell for expression of a polypeptide encoded by an open reading frame in a polynucleotide of the invention. Plant host cells include, for example, plant cells that could function as suitable hosts for the expression of a polynucleotide of the invention include epidermal cells, mesophyll and other ground tissues, and vascular tissues in leaves, stems, floral organs, and roots from a variety of plant species, such as *Arabidopsis thaliana*, *Nicotiana tabacum*, *Brassica napus*, *Zea mays*, *Oryza sativa*, *Gossypium hirsutum* and *Glycine max*.

Transformed Plants Cells and Transgenic Plants

The invention includes a protoplast, plants cell, plant tissue and plant (e.g., monocot or dicot) transformed with a bHLH subgroup 1b nucleic acid, a vector containing a bHLH subgroup 1b nucleic acid or an expression vector containing a bHLH subgroup 1b nucleic acid. As used herein, "plant" is meant to include not only a whole plant but also a portion thereof (i.e., cells, and tissues, including for example, leaves, stems, shoots, roots, flowers, fruits and seeds).

The plant can be any plant type including, for example, species from the genera *Arabidopsis*, *Brassica*, *Oryza*, *Zea*, *Sorghum*, *Brachypodium*, *Miscanthus*, *Gossypium*, *Triticum*, *Glycine*, *Pisum*, *Phaseolus*, *Lycopersicon*, *Trifolium*, *Cannabis*, *Cucurbita*, *Rosa*, *Vitis*, *Juglans*, *Fragaria*, *Lotus*, *Medicago*, *Onobrychis*, *Trigonella*, *Vigna*, *Citrus*, *Linum*, *Geranium*, *Manihot*, *Daucus*, *Raphanus*, *Sinapis*, *Atropa*, *Capsicum*, *Datura*, *Hyoscyamus*, *Nicotiana*, *Solanum*, *Petunia*, *Digitalis*, *Majorana*, *Ciahorium*, *Helianthus*, *Lactuca*, *Bromus*, *Asparagus*, *Antirrhinum*, *Heterocallis*, *Nemesis*, *Pelargonium*, *Panieum*, *Pennisetum*, *Ranunculus*, *Senecio*, *Salpiglossis*, *Cucumis*, *Browaalia*, *Lolium*, *Avena*, *Hordeum*, *Secale*, *Picea*, *Caco*, and *Populus*.

The invention also includes cells, tissues, including for example, leaves, stems, shoots, roots, flowers, fruits and seeds and the progeny derived from the transformed plant.

Numerous methods for introducing foreign genes into plants are known and can be used to insert a gene into a plant host, including biological and physical plant transformation protocols (See, for example, Miki et al., (1993) "Procedure for Introducing Foreign DNA into Plants", In: Methods in Plant Molecular Biology and Biotechnology, Glick and Thompson, eds., CRC Press, Inc., Boca Raton, pages 67-88; and Andrew Bent in, Clough S J and Bent A F, (1998) "Floral dipping: a simplified method for *Agrobacterium*-mediated transformation of *Arabidopsis thaliana*"). The methods chosen vary with the host plant, and include chemical transfection methods such as calcium phosphate, polyethylene glycol (PEG) transformation, microorganism-mediated gene transfer such as *Agrobacterium* (Horsch et al., 1985), electroporation, protoplast transformation, micro-injection, flower dipping and biolistic bombardment.

Agrobacterium-Mediated Transformation

The most widely utilized method for introducing an expression vector into plants is based on the natural transformation system of *Agrobacterium tumefaciens* and *A. rhizogenes* which are plant pathogenic bacteria which genetically transform plant cells. The Ti and Ri plasmids of *A. tumefaciens* and *A. rhizogenes*, respectfully, carry genes responsible for genetic transformation of plants (See, for example, Kado, 1991). Descriptions of the *Agrobacterium* vector systems and methods for *Agrobacterium*-mediated gene transfer are provided in Gruber et al. (1993) and Moloney et al., (1989).

Transgenic *Arabidopsis* plants can be produced easily by the method of dipping flowering plants into an *Agrobacterium* culture, based on the method of Andrew Bent in, Clough S J and Bent A F, 1998. Floral dipping: a simplified method for *Agrobacterium*-mediated transformation of *Arabidopsis thaliana*. Wild type plants are grown until the plant has both developing flowers and open flowers. The plants are inverted for 1 minute into a solution of *Agrobacterium* culture carrying the appropriate gene construct. Plants are then left horizontal in a tray and kept covered for two days to maintain humidity and then righted and bagged to continue growth and seed development. Mature seed is bulk harvested.

Direct Gene Transfer

A generally applicable method of plant transformation is microprojectile-mediated transformation, where DNA is carried on the surface of microprojectiles measuring about 1 to 4 µm. The expression vector is introduced into plant tissues with a biolistic device that accelerates the microprojectiles to speeds of 300 to 600 m/s which is sufficient to penetrate the plant cell walls and membranes (Sanford et al., 1993; Klein et al., 1992).

Plant transformation can also be achieved by the Aerosol Beam Injector (ABI) method described in U.S. Pat. Nos. 5,240,842 and 6,809,232. Aerosol beam technology is used to accelerate wet or dry particles to speeds enabling the particles to penetrate living cells. Aerosol beam technology employs the jet expansion of an inert gas as it passes from a region of higher gas pressure to a region of lower gas pressure through a small orifice. The expanding gas accelerates aerosol droplets, containing nucleic acid molecules to be introduced into a cell or tissue. The accelerated particles are positioned to impact a preferred target, for example a plant cell. The particles are constructed as droplets of a sufficiently small size so that the cell survives the penetration. The transformed cell or tissue is grown to produce a plant by standard techniques known to those in the applicable art.

Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregate and can transmit the bHLH subgroup 1b gene construct to its progeny. A more preferred transgenic plant is homozygous for the gene construct, and transmits that gene construct to all offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the bHLH subgroup 1b gene.

Method of Producing Transgenic Plants

Also included in the invention are methods of producing a transgenic plant having increased heat stress tolerance, reduced flower abortion, and increased yield relative to a wild type plant following a heat stress. The method includes introducing into one or more plant cells a compound that increases bHLH subgroup 1b expression or activity in the plant to generate a transgenic plant cell and regenerating a transgenic plant from the transgenic cell. The compound can be, e.g., (i) a bHLH subgroup 1b polypeptide; (ii) a bHLH subgroup 1b nucleic acid, analog, homologue, orthologue, portion, variant or complement thereof; (iii) a nucleic acid that increases expression of a bHLH subgroup 1b nucleic acid. A nucleic acid that increases expression of a bHLH subgroup 1b nucleic acid may include promoters or enhancer elements. The bHLH subgroup 1b nucleic acid can be either endogenous or exogenous, for example an Arabidopsis bHLH subgroup 1b nucleic acid may be introduced into a *Brassica* or corn species. Preferably, the compound is a bHLH subgroup 1b nucleic acid sequence endogenous to the species being transformed. Alternatively, the compound is a bHLH subgroup 1b nucleic acid sequence exogenous to the species being transformed and having at least 70%, 75%, 80%, 85%, 90% or greater homology to the endogenous target sequence.

In various aspects the transgenic plant has an altered phenotype as compared to a wild type plant (i.e., untransformed). By altered phenotype is meant that the plant has a one or more characteristic that is different from the wild type plant. For example, when the transgenic plant has been contacted with a compound that increases the expression or activity of a bHLH subgroup 1b nucleic acid, the plant has a phenotype such as increased heat stress tolerance, reduced flower abortion, and increased yield relative to a wild type plant following heat stress.

The plant can be any plant type including, for example, species from the genera *Arabidopsis, Brassica, Oryza, Zea, Sorghum, Brachypodium, Miscanthus, Gossypium, Triticum, Glycine, Pisum, Phaseolus, Lycopersicon, Trifolium, Cannabis, Cucurbita, Rosa, Vitis, Juglans, Fragaria, Lotus, Medicago, Onobrychis, Trigonella, Vigna, Citrus, Linum, Geranium, Manihot, Daucus, Raphanus, Sinapis, Atropa, Capsicum, Datura, Hyoscyamus, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Lolium, Avena, Hordeum, Secale, Picea, Caco,* and *Populus.*

EXAMPLES

Example 1

Identification of Homologous Genes

Blast searches of bHLH39 and its *Arabidopsis* homologues bHLH38, bHLH100, and bHLH101 were performed against NCBI's protein, nucleotide, and EST databases and TIGR's unigene database (1e-01). Genomic sequence databases was used for species whose complete sequence in known, such as Rice and Sorghum. To confirm a sequence was indeed an ortholog of the sequences of interest, all putative homologues were then blasted against the complete *Arabidopsis* protein database, and any sequence whose top *Arabidopsis* hit was not one of the four sequences of interest was filtered from any further analysis. The minimize redundancy between multiple hits, all EST sequence hits were assembled using the cap3 assembly program ensuring they have a minimum of 90% identity across at least 40 nucleotide with a maximum of 5 gaps. Open reading frames were determined using the EMBOSS program getorf.

Blast searches of AtbHLH39, AtbHLH38, AtbHLH100, AtbHLH101 retrieved 96 homologues sequences from 40 different species. Sequence conservation was limited to DNA binding and dimerization domains, with little to no conservation outside of this area. Homologues were discovered in both monocots and dicots suggesting an important functional requirement in plants. Homologues of AtbHLH39 in agronomical important species such as rice and corn were retrieved as well as species used in biofuels such as Brachypodium and Switchgrass.

According to blast searches against the Brachypodium genomic database, there are three homologues to this group of genes, and all three are most similar to AtbHLH38. There is EST evidence for two of three the homologues. Whether the third homologue is a pseudogene or codes for a functional protein is yet to be determined.

In two other monocot species, rice and Sorghum, there is only one homologue from this group, and in both species the homologue is closest to AtbHLH38. In both rice and Sorghum, the gene encodes at least two splice variants.

There are at least two homologues of this group in *Brassica napus*, one protein with close homology to AtbHLH39, and another with close homology to AtbhLH38. However, the BnbHLH39 homologue contains a nonsense mutation which results in the coding of a partial protein with no DNA binding or dimerization domain. This finding is confirmed with several EST's, and also occurs in *Brassica rapa.*

Example 2

Vector Construction

The binary vector pBI121 was optimized for transformation of *Arabidopsis* and different crops. The GUS gene in pBI121 was deleted by SmaI and EcolCR1 digestions and religation, resulting in vector pBI121ΔGUS. This vector was used to clone gene for overexpression. The C-terminal 1.1-Kb portion of the GUS gene was isolated from pBI121 as an EcoR V-Sac I fragment (positions 6613-7715 in pBI121) and cloned at the Sma I and Sac I sites in pBI121ΔGUS, resulting in pBI121tGUS (with N-terminal portion of the GUS gene deleted). The vector was used to make gene down-regulation Hairpin constructs with the partial GUS sequence as the loop or spacer.

The NPTII gene in the vector pBI121 and its derivatives contains a point mutation (G to T at position 3383 in pBI121, amino acid substitution E182D). The mutant enzyme showed several fold lower enzyme activity than its wild type (PNAS, 87:3435-3439, 1990). In order to improve transformation efficiency of different crops, the vectors pBIΔGUS and pBItGUS were restored with the WT-NPTII gene: a Nhe I-BstB I fragment (0.9 kb, positions 2715-3648) was replaced with a Nhe I-BstB I fragment of exactly the same sequence except the single nucleotide difference. The fragment was isolated by restriction digestion from plasmid pRD400 which contained the WT-NPTII gene (PNAS, 87:3435-3439, 1990; Gene, 122:383-384, 1992). The modified vectors were named pBI300ΔGUS and pBI300tGUS, respectively. The WT-NPTII gene was also isolated from pBI300ΔGUS as a Nhe I-Hind III fragment (2.2 kb) and cloned at the corresponding sites in pBI121. This generated vector pBI300GUS. To distinguish these vectors from others, pBI121-based binary vectors containing the WT-NPTII gene were designated pBI300 series.

In order to use Basta as a selection agent, a Basta resistance marker was subcloned into pBI121. A 1.3-kb Ase I fragment encompassing the Basta selection marker (35S-Bar-nosT) was amplified by PCR from vector pEGAD using a forward primer containing a Pme I site and a reverse primer containing a Hind III site. The fragment was cloned, between the sites of PmeI (position 2492) a III (position 4950) in pBI121, pBIΔGUS and pBItGUS. As a result the, the kanamycin selection marker (Pnos-NPTII-nosT) was replaced with the Basta selection marker in these vectors. To distinguish these vectors from others, pBI121-based binary vectors containing the Basta selection marker gene were designated pBI800 series.

pBI300 vectors contain the WT-NPTII gene driven by the nopaline synthase (nos) promoter. Since the promoter is not active in monocotyledon plants, it was necessary to replace it with a strong promoter for transformation of monocotyledon plants. For this purpose, the Brachyposium TIF1 gene (BdTIF1, also called BdGOS2) promoter was cloned into vectors of the pBI300 series to drive the WT-NPTII gene. The BdTIF1 promoter sequence (-1 through -2548 with respect to the ATG start codon, including the first exon, first intron and portion of the second exon) was amplified by PCR as a PmeI-NheI fragment and cloned at the corresponding sites in HSP81.1-AtMyb68-pBI300 (a pBI300-based vector containing the *Arabidopsis* heat shock protein 81.1 promoter and *Arabidopsis* Myb68 coding sequence, see below for details). As a result the TIF1p promoter was placed 5' upstream to the WT-NPTII gene with a small fragment of about 120 bp (including 65 bp of the nos promoter) between them. In order to eliminate the 120-bp fragment, the WT-NPTII coding sequence and flanking vector sequence was amplified as a Nhe I-Sal I fragment (2.1 Kb) and ligated to the plasmid digested with Nhe I and Sal I. The cloning resulted in vector HSP81.1-AtMyb68-pBI500. pBI121-based vectors containing the WT-NPTII gene driven by the BdTIF1 promoter were designated pBI500 series. The HSP81.1-AtMyb68 sequence was also replaced with the 35S promoter sequence as a Hind III-BamH I fragment isolated by restriction digestion from pBI300ΔGUS. This generated vector pBI500ΔGUS.

Example 3 bHLH Subgroup b1 Over-Expression Constructs

Construct 35S-AtbHLH39:
The AtbHLH39 (At3g56980) coding sequence was amplified by RT-PCR from Arabidopsis using forward primer BHLH039FW-XbaI and reverse primer BHLH039RV-BamH I. The PCR product (0.8 Kb) was cloned at the Xba I and BamH I site in the binary vector pBI300ΔGUS and pBI800ΔGUS, generating construct 35S-AtbHLH39-pBI300 and 35S-AtbHLH39-pBI800, respectively.
Construct 35S-AtbHLH101:
The AtbHLH101 (At5g04150) coding sequence was amplified by RT-PCR from Arabidopsis using forward primer BHLH101FW-XbaI and reverse primer BHLH101RV-BamH I. The PCR product (0.7 Kb) was cloned at the Xba I and BamH I site in the binary vector pBI300ΔGUS and pBI800ΔGUS, generating construct 35S-AtbHLH101-pBI300 and $^{35}$S-AtbHLH101-pBI800, respectively.
Construct 35S-AtbHLH38:
Using the same strategy as described above, the AtbHLH38 (at3g56970) coding sequence is amplified by RT-PCR from Arabidopsis using a forward primer containing an Xba I site and reverse primer containing a Bam HI site, and cloned at the Xba I and BamH I site in the binary vector pBI300ΔGUS, generating construct 35S-AtbHLH38-pBI300.
Construct 35S-AtbHLH100:
Using the same strategy as described above, the AtbHLH100 (At2g41240) coding sequence is amplified by RT-PCR from Arabidopsis using a forward primer containing an Xba I site and reverse primer containing a Bam HI site, and cloned at the Xba I and BamH I site in the binary vector pBI300ΔGUS, generating construct 35S-AtbHLH100-pBI300.
Constructs HSP81.1-AtbHLH39:
Several steps were involved in the development of the construct. A first, promoter sequence (−401 to −1 with respect to the ATG start codon) of the Arabidopsis heat shock protein gene HSP81.1 (At5g52640) was PCR amplified with primers having Sal I and Xba I ends from Arabidopsis genomic DNA, and cloned at the same sites in pBI101, thereby replacing the 35S promoter. This vector was named pHSP81.1-GUS. Sequencing revealed point mutations of T to C at position −266 and C to T at −121 in the promoter. The GUS staining of Arabidopsis seedlings transformed with this construct showed the same heat induction expression profile as reported in the literature. Hence these mutations do not apparently affect the functionality of the promoter. Secondly, MCS2-oligo from New England Biolabs was annealed and ligated to pHSP81.1-GUS that had been digested with Xba I and Sma I. This resulted in vector pHSP81.1MCS-GUS. Thirdly, the GUS sequence was deleted by SmaI and Eco1CR1 digestion, and vector self-religation. This led to vector pHSP81.1MCSΔGUS. Fourthly, the AtMyb68 coding sequence (At5g65790) was cloned at the XbaI and BamH I sites for Myb68 overexpression. Fifthly, the mutant NPTII sequence was replaced with its WT sequence as described above, producing vector HSP81.1-AtMyb68-pBI300. Finally, the AtbHLH39 coding sequence as an Xba I-BamH I fragment was cloned at the Xba I and BamH I site thereby replacing the AtMyb68 sequence, resulting in construct HSP81.1-AtbHLH39-pBI300. Likewise the Xba I-BamH I fragment of AtbHLH39 coding sequence replaced the AtMyb68 sequence in HSP81.1-AtMyb68-pBI500, resulting in the vector HSP81.1-AtbHLH39-pBI500.
Construct UCC2-AtBHLH39:
Arabidopsis uclacyanin2 gene (UCC2, At2g44790) is expressed at very high level in the roots. Its expression is detectable but at very low levels in other parts of the plant. Its cell-specific expression profile in the root is similar to that of AtbHLH39, i.e. predominantly expressed in endodermis and cortex and stele. The UCC2 gene promoter sequence (−1 through −1475 with respect to the ATG start codon) was amplified by PCR using forward primer containing a Sal I site (P790-Sal-F) and reverse primer containing an XbaI site (P790-Xb-R). The PCR product of the UCC2 promoter was cloned at the Sal I and Xba I sites in the vector HSP81.1-AtMyb68-pBI300 (see above), replacing the HSP81.1 promoter. The AtbHLH39 coding sequence was then cloned into this vector as an Xba I-BamH I fragment, replacing the AtMyb68 coding sequence. The resulting vector is named UCC2-AtbHLH39-pBI300.
Construct BdBS-AtbHLH39-pBI500:
Brachypodium biotin synthase (BdBS) gene promoter (−1 through −553 with respect to the ATG start codon) was PCR amplified as a Sal I-Xba I fragment and was cloned to substitute the HSP81.1 promoter in HSP81.1-AtbHLH39-pBI500. The resulting vector was named BdBS-AtbHLH39-pBI500.
Construct BdUCC-AtbHLH39-pBI500:
The closest Brachypodium homolog of the Arabidopsis uclacyanin2 gene was found in genomic sequence super_67. The sequence was 34% identical to Arabidopsis uclacyanin2 along aligned regions. The open reading frame was determined. A reverse blast of the translated protein sequence to the Arabidopsis TAIR8 proteins found it to be the most similar to Arabidopsis Uclacyanin1, a close homologue of uclacyanin2 In Arabidopsis, uclacyanin1 shares similar expression pattern to uclacyanin2 but with an overall weaker expression. The promoter sequence of the Brachypodium uclacyanin homolog (BdUCC) promoter (−22 through −1405 relative to the ATG start codon) was amplified as a Sal I-Xba I fragment as was cloned to substitute the HSP81.1 promoter in HSP81.1-AtbHLH39-pBI500. The resulting vector was named BdUCC-AtbHLH39-pBI500.

Example 4

Cloning of the Brachypodium bHLH39

There are three Brachypodium bHLH genes with high homology to the Arabidopsis bHLH subgroup 1b comprising bHLH39, bHLH 38, bHLH 100 and bHLH 101. All three Brachypodium homologues are most closely related to AtbHLH38. There is strong EST evidence for homologue #1

(super_13.506): the 5' portion is identical to sequence in EST DV488230 while the 3' portion is identical to DV488393 which contains polyAs. However, DV488393 also contains sequence apparently belonging to an intron. Therefore, the exact open reading frame remains to be determined. The putative coding sequence (BdbHLH39H1) is cloned by RT-PCR using forward primer BdH1-Xb-F (containing an Xba I site) and reverse primer BdH1-Bm-R (containing a BamH I site), and cloned into the corresponding sites in a vector to make constructs HSP81.1-BdbHLH39H1-pBI500, BdBS-BdbHLH39-BI500 and BdUCC-BdbHLH39H1-pBI500.

Primers

TABLE 1

Cloning Primers

| SEQ ID | Name | Sequence (5' to 3') | PCR product |
|---|---|---|---|
| 106 | BHLH039FW-XbaI | aaaTCTAGAATGTGTGCATTAGTACCTCCATTGTTTC | AtbHLH39 CDS, |
| 107 | BHLH039RV-BamHI | aaaGGATCCTCATATATATGAGTTTCCACATTCCTCATAC | 0.8 Kb |
| 108 | BHLH101FW-XbaI | aaatCTAGAATGGAGTATCCATGGCTGCAGTCTC | AtbHLH101CDS, |
| 109 | BHLH101RV-BamHI | aaaGGATCCTTATGATTGGCGTAATCCCAAGAGC | 0.7 Kb |
| 110 | P790-Sal-F | acgtGTCGAC CTT AGC CAA TGG ATG AGG ATG | AtUCC2 |
| 111 | P790-Xb-R | acgtTCTAGA TTT TTG TTT ACT GTA GAA GAG | promoter, 1.5 Kb |
| 112 | BdGOS-Pm-F10 | acgtGTTTAAAC GCA TAG ACT CTC AGC GGA GAG | BdTIF1 promoter, |
| 113 | BdGOS-Nh-R | acgtGCTAGC gaaaactcctggtgagagtgg | 2.5 Kb |
| 114 | NPTII-Nh-F | acgtGCTAGC atgattgaacaagatggattgcac | WT-NPTII and |
| 115 | NPTII-Sal-R | acgtGTCGAC CTG CAG GCA TGC AAG CTT GG | flanking sequence, 2.1 Kb |
| 116 | BdBSp-Sal-F | acgtGTCGAC ctctggatgcctaaacaaacgac | BdBS promoter, |
| 117 | BdBSp-Xb-R | acgtTCTAGA ggcttttgtcggtcggcctg | 0.5 Kb |
| 118 | BdUCCp-Sa-F4 | acgtGTCGAC GGA GGT GCA GTT TGC AGC AG | BdUCC promoter, |
| 119 | BdUCCp-Xb-R4 | acgtTCTAGA TAT AGA GAG AGG GTG ATC AAC GA | 1.4 Kb |
| 120 | BdH1-Xb-F | acgtTCTAGA ATG GGG CAC AAG CAG CTG TTC | BdbHLH39 homolog, |
| 121 | BdH1-Bm-R | acgtGGATCC TCA CTG ATG CAT ATG CAG TCC | super_13.506 (0.7 Kb) |

Example 5

Plant Transformations

The constructs described above have been or are transformed into *Arabidopsis* and Brachypodium as appropriate. Other species are transformed with an appropriate vector and transformed plants produced.

TABLE 2

Transformation of Constructs

| CONSTRUCT | TARGET SPECIES | Transformed |
|---|---|---|
| 35S-AtbHLH39-pBI300 | Dicots i.e. *Arabidopsis*(At), *Brassica*(Bn) | At, Bn |
| 35S-AtbHLH39-pBI800 | Dicots i.e. *Arabidopsis*(At), *Brassica*(Bn) | |
| 35S-AtbHLH101-pBI300 | Dicots i.e. *Arabidopsis*(At), *Brassica*(Bn) | At |
| 35S-AtbHLH101-pBI800 | Dicots i.e. *Arabidopsis*(At), *Brassica*(Bn) | |
| 35S-AtbHLH38-pBI300 | Dicots i.e. *Arabidopsis*(At), *Brassica*(Bn) | |
| 35S-AtbHLH100-pBI300 | Dicots i.e. *Arabidopsis*(At), *Brassica*(Bn) | |
| HSP81.1-AtbHLH39-pBI300 | Dicots i.e. *Arabidopsis*(At), *Brassica*(Bn) | At, Bn |
| HSP81.1-AtbHLH39-pBI500 | Monocots, i.e. *Brachypodium* | |
| UCC2-AtbHLH39-pBI300 | Dicots i.e. *Arabidopsis*(At), *Brassica*(Bn) | |

TABLE 2-continued

Transformation of Constructs

| CONSTRUCT | TARGET SPECIES | Transformed |
|---|---|---|
| HSP81.1-AtbHLH39-pBI500 | Monocots, i.e. Brachypodium | |
| BdBS-AtbHLH39-pBI500 | Monocots, i.e. Brachypodium | |
| HSP81.1-AtbHLH39-pBI500 | Monocots, i.e. Brachypodium | |
| BdUCC-AtbHLH39-pBI500 | Monocots, i.e. Brachypodium | |
| HSP81.1-BdbHLH39H1-pBI500 | Monocots, i.e. Brachypodium | |
| BdBS-BdbHLH39-BI500 | Monocots, i.e. Brachypodium | |
| BdUCC-BdbHLH39H1-pBI500 | Monocots, i.e. Brachypodium | |

Example 6

Methods of Transformation

*Arabidopsis* transgenic plants were made by the method of dipping flowering plants into an *Agrobacterium* culture, based on the method of Andrew Bent in, Clough S J and Bent A F, 1998. Floral dipping: a simplified method for *Agrobacterium*-mediated transformation of *Arabidopsis thaliana*. Wild type plants were grown under standard conditions with a 16 hour, 8 hour light to dark day cycle, until the plant has both developing flowers and open flowers. The plant was inverted for 2 minutes into a solution of *Agrobacterium* culture carrying the appropriate gene construct. Plants were then left horizontal in a tray and kept covered for two days to maintain humidity and then righted and bagged to continue growth and seed development. Mature seed was bulk harvested.

Transformed T1 plants were selected by germination and growth on MS plates containing 50 µg/ml kanamycin or an appropriate selection medium. Green, kanamycin resistant (Kan$^R$) seedlings were identified after 2 weeks growth and transplanted to soil. Plants were bagged to ensure self fertilization and the T2 seed of each plant harvested separately. During growth of T1 plants leaf samples were harvested, DNA extracted and Southern blot and PCR analysis performed.

T2 seeds were analyzed for Kan$^R$ segregation. From those lines that showed a 3:1 resistant phenotype, surviving T2 plants were grown, bagged during seed set, and T3 seed harvested from each line. T3 seed was again used for Kan$^R$ segregation analysis and those lines showing 100% Kan$^R$ phenotype were selected as homozygous lines. Further molecular and physiological analysis was done using T3 seedlings.

Transgenic *Brassica napus*, *Glycine max* and *Zea maize* plants are produced using *Agrobacterium* mediated transformation of cotyledon petiole tissue. Seeds are sterilized as follows. Seeds are wetted with 95% ethanol for a short period of time such as 15 seconds. Approximately 30 ml of sterilizing solution I is added (70% Javex, 100 µl Tween20) and left for approximately 15 minutes. Solution I is removed and replaced with 30 ml of solution II (0.25% mecuric chloride, 100 µl Tween20) and incubated for about 10 minutes. Seeds are rinsed with at least 500 ml double distilled sterile water and stored in a sterile dish. Seeds are germinated on plates of ½ MS medium, pH 5.8, supplemented with 1% sucrose and 0.7% agar. Fully expanded cotyledons are harvested and placed on Medium I (Murashige minimal organics (MMO), 3% sucrose, 4.5 mg/L benzyl adenine (BA), 0.7% phytoagar, pH5.8). An *Agrobacterium* culture containing the nucleic acid construct of interest is grown for 2 days in AB Minimal media. The cotyledon explants are dipped such that only the cut portion of the petiole is contacted by the *Agrobacterium* solution. The explants are then embedded in Medium I and maintained for 5 days at 24° C., with 16, 8 hr light dark cycles. Explants are transferred to Medium II (Medium 1,300 mg/L timentin,) for a further 7 days and then to Medium III (Medium II, 20 mg/L kanamycin). Any root or shoot tissue which has developed at this time is dissected away. Transfer explants to fresh plates of Medium III after 14-21 days. When regenerated shoot tissue develops the regenerated tissue is transferred to Medium IV (MMO, 3% sucrose, 1.0% phytoagar, 300 mg/L timentin, 20 mg/L 20 mg/L kanamycin). Once healthy shoot tissue develops shoot tissue dissected from any callus tissue are dipped in 10×IBA and transferred to Medium V (Murashige and Skooge (MS), 3% sucrose, 0.2 mg/L indole butyric acid (IBA), 0.7% agar, 300 mg/L timentin, 20 mg/L 20 mg/L kanamycin) for rooting. Healthy plantlets are transferred to soil. The above method, with or without modifications, is suitable for the transformation of numerous plant species including *Glycine max*, *Zea maize* and cotton.

Transgenic *Glycine max*, *Zea maize* and cotton are produced using *Agrobacterium*-based methods which are known to one of skill in the art. Alternatively one can use a particle or non-particle biolistic bombardment transformation method. An example of non-particle biolistic transformation is given in U.S. Patent Application 20010026941. This method has been used to produce transgenic *Glycine max* and *Zea maize* plants. Viable plants are propagated and homozygous lines are generated. Plants are tested for the presence of drought tolerance, physiological and biochemical phenotypes as described elsewhere.

Transformation of plant tissue such as *Zea maize*, for example, are achieved by sonication of callus tissue culture. Callus tissue was produced as follows. Ears of corn were harvested 18 days after silking and surface sterilized in 50% v/v bleach for 20 minutes followed by three washing with sterile distilled water. Immature embryos ranging in size from 2 to 4 mm were harvested from the kernels. Embryos were placed on MSD$_{1.5}$ medium (2% sucrose, 1×MS macronutrient and micronutrient salts, 1×MS vitamins, 1.5 mg/L 2,4-D, 0.8% agar, pH 5.8) scutellum side up. Embryos were incubated at 26-28° C. in the dark. Friable callus from 2 week old cultures were transferred to fresh MSD$_{1.5}$ medium and further incubated at 26-28° C. in the dark. Friable callus was subcultured to fresh $MSD_{1.5}$ medium every 21 days.

Transformation of callus tissue was performed as described below. The construct was introduced into GV3101 *Agrobacterium* by inoculation of a single colony of GV3101 *Agrobacterium* containing the HPR-GUS plasmid into 10 mL of LB amended with 150 μg/mL rifampicin, 100 μg/mL gentamycin sulfate, and 50 μg/mL kanamycin. The culture was allowed to grow overnight at 28° C. with 200 rpm shaking Corn callus was cut into pieces approximately 3-5 mm in size. The *Agrobacterium* culture was centrifuged at 1500×g for 10 minutes and washed twice with 10 mL liquid $MSD_{1.5}$ liquid (2% sucrose, 1×MS macronutrient and micronutrient salts, 1×MS vitamins, 1.5 mg/L 2,4-D, pH 5.8). The bacteria was resuspended in liquid $MSD_{1.5}$ to an $OD_{600nm}$ of 0.25 and 1 mL of diluted *Agrobacterium* or liquid $MSD_{1.5}$, for negative controls, was placed in 1.5 mL microfuge tubes containing four pieces of callus added to each tube. Callus and *Agrobacterium* culture was sonicated in a Branson 200 Ultrasonic Cleaner for 0, 3, 10, 30, 100, or 300 seconds with bacteria or 0 or 300 seconds without bacteria (in $MSD_{1.5}$ liquid alone). After sonication, the callus was blotted on sterile filter paper and placed on $MSD_{1.5}A$ medium ($MSD_{1.5}$ solid medium amended with 100 μM acetosyringone). The co-cultivation period was 4 days in the dark at 28° C. Callus was rinsed in liquid $MSD_{1.5}$, blotted on sterile filter paper, and placed on $MSD_{1.5}T$ medium ($MSD_{1.5}$ solid medium amended with 400 μg/mL Timentin) for 3 days in the dark at 28° C. Seven days after sonication, callus was added to 1 mL GUS staining solution (50 mM $NaPO_4$, pH 7.0, 0.1% Triton X-100, 1 mM EDTA, 2 mM DTT, 0.5 mg/mL X-GlcA) and left to incubate overnight at 37° C. The staining solution was replaced with 1 mL fixation buffer (10% formaldehyde, 50% ethanol) and incubated for 30 minutes at room temperature. The fixation buffer was replaced with 80% ethanol and incubated for 1 hour at room temperature. The 80% ethanol was replaced with 100% ethanol and incubated for 1 hour at room temperature. The callus was assessed for blue staining, indicating GUS activity.

Other methods of plant transformation are used when appropriate and are commonly described and known in the art.

Example 7

Expression Analysis

Total RNA was isolated from 22 transgenic 35S-AtbHLH39 lines and wild type *Arabidopsis* lines. Approximately 10 μμg of total RNA was loaded into each lane. The Northern was probed with radiolabeled HPR cDNA in ExpressHyb hybridization solution (Clontech) and exposed using a phosphoimaging screen. For quantification blots were reprobed with tubulin, a constitutively expressed gene, for a comparative standard.

The expression level of AtbHLH39 was elevated 4 fold to 126 fold higher than that of the WT Columbia control. The best performing lines (line-34 and line-97) based on heat and drought tolerance, had 50 and 40 fold increase in expression of AtbHLH39 respectively.

Example 8

Microarray and Expression Analysis bHLH subgroup 1b includes AtbHLH38, AtbHLH39, AtbHLH100 and AtbHLH101. Microarray data of lines transformed with an overexpression construct to increase MYB68 expression or activity (35S-AtMYB68) showed that the RNA expression of AtbHLH39 and AtbHLH101 was increased 32 fold and 15 fold, respectively when AtMYB68 was over-expressed 37 fold. The AtbHLH38 and AtbHLH100 genes were not present on the microarray chip, so the expression of these closely related genes is yet to be determined. The four AtbHLH38, AtbHLH39, AtbHLH100, AtbHLH101 members have high sequence homology in group 1b, and may be at least partially functionally redundant.

AtbHLH39 expression is mainly co-localized with AtMYB68 in the pericycle of the root as is that of Myb68 (Birnbaum et al. 2003; Schmid et al. 2005). Analysis of the endogenous MYB68 promoter and the AtbHLH39 promoter demonstrates that these promoters express predominantly in root tissue.

Further microarray analysis, the gene expression of IRT1 is not significantly affected in the transgenic plants over-expressing AtbHLH39 (35S-AtbHLH39 construct) suggesting that the heat tolerance phenotype conferred by AtbHLH39 overexpression does not regulate IRT1 gene expression and that the reported involvement of bHLH39 in iron deprivation responses occurs through a separate pathway.

Transcription characteristics of members of the bHLH subgroup 1b transcription factor gene family AtbHLH39, AtbHLH38, AtbHLH100, and AtbHLH101 were analyzed. The AtbHLH39 expresses predominantly in the root, whereas AtbHLH38, AtbHLH100, and AtbHLH101 have low expression in leaf, bud, flower and root tissues. The AtbHLH38 transcription is barely detectable in root and leaf, AtbHLH100 expresses in very low level in the bud and flower and AtbHLH101 also expresses at very low level in root and leaf.

Example 9

MYB68 Binds to the bHLH39 Promoter

Electrophoretic mobility shift assays (EMSA) were performed to determine whether MYB68 protein could bind to the promoter sequence of AtbHLH39. Four different segments of the promoter were labeled and tested: P1 (−1 to −224, with respect to the ATG start codon), P2 (−204 to −419), P3 (−401 to −623) and P4 (−601 to −788). The labeled probe DNA was incubated with purified MYB68 fusion protein. A DNA-protein complex was detected with probe P1 while other regions of the promoter showed no binding with MYB68. Formation of the complex P1/Myb68 was eliminated by the addition of cold competitor DNA with the same sequence as the probe, but not affected by cold competitors of P3. Moreover, no DNA-protein complex was formed when probe P1 was incubated with a truncated MYB68 protein (MYB68CD) in which the R2R3DNA-binding domains was deleted. The data demonstrated that MYB68 protein bind specifically to the AtbHLH39 promoter in the region −1 to −224.

To further localize the MYB68 binding site, four double-stranded oligonucleotides covering the promoter region −1 to −232 were tested as competitors in binding assays: P11 (−1 to −61), P12 (−52 to −118), P13 (−109 to −178) and P14 (−169- to −232). Binding of MYB68 to the probe P1 was abolished by the competitor P12, but not affected by other fragments, indicating that the MYB68 binding site is within the sequence −52 to −118.

Example 10

Constitutive Expression of At-bHLH39 in *Arabidopsis* Results in Reduced Flower Abortion Following Heat Stress An experiment was set up with 14 transgenic 35S-AtbHLH39 lines and a wild type (WT) control. Plants were grown in 2.25 inch pots under optimal conditions (22 C, 18 hr light of 200 uE, 60% RH) in a growth chamber until three days post-appearance of the first flower. A heat stress treatment was applied by placing plants at 42 C for 2 hours. One week following the stress period the plants were assessed for number of aborted flowers. The results are shown in Table 3. Ten of the transgenic lines had reduced flower abortion relative to WT controls. One of the lines (34-1) had statistically significantly less aborted flowers than the WT.

TABLE 3

Average flower abortion following 2 hr at 42 C. (n = 6 to 11) ± SE

| Entry | # of aborted flowers | Flower abortion as % of WT |
|---|---|---|
| 97-7 | 2.5 ± 0.5 | 44% |
| 34-1 | 2.9 ± 0.3 | 51% |
| 46-10 | 3.2 ± 0.3 | 56% |
| 57-2 | 3.6 ± 0.4 | 64% |
| 1-7 | 3.8 ± 0.2 | 67% |
| 41-2 | 4.1 ± 0.3 | 72% |
| 38-10 | 4.5 ± 0.7 | 79% |
| 96-4 | 4.5 ± 0.5 | 79% |
| 12-4 | 4.7 ± 0.5 | 82% |
| 30-2 | 4.8 ± 0.5 | 85% |
| 94-10 | 5.1 ± 0.9 | 90% |
| 10-1 | 5.7 ± 0.5 | 100% |
| 52-4 | 6.2 ± 0.7 | 108% |
| 103-1 | 6.2 ± 0.6 | 109% |
| WT | 5.7 ± 0.6 | 100% |

Example 11

Constitutive Expression of AtbHLH39 in *Arabidopsis* Results in Drought Tolerance of the Plants Drought tolerance was assessed in six transgenic At-bHLH39 lines that also showed reduced flower abortion following heat stress. Plants were grown (5 per 3 inch pot, n=8) under optimal conditions in a growth chamber (22 C, 18 hr light of 200 uE, 60% RH) until the first open flower. Drought treatment was applied by watering up all plants to the same saturated level. Further water was withheld. Plants were weighed daily to determine the daily water loss and all plants were harvested on day four of treatment, at which time all plants were visibly wilting. The water loss relative to final shoot biomass was calculated and is a representative indicator of drought tolerance. Data was normalized to WT which was set as 100% (Table 4). All six of the lines showed reduced water loss relative to shoot biomass, 3 of which were significant statistically. This is indicative of drought tolerant phenotype. Two of the best performing drought tolerant lines were also the best performing heat tolerant lines thereby indicating a close link between the two traits: drought tolerance and heat tolerance as a result of constitutive expression of AtbHLH39 in *Arabidopsis*.

TABLE 4

Water loss relative to shoot dry weight and drought tolerance in 35S-bHLH39 transgenic lines

| Entry | Water lost in 3d/shoot DW d4 | Drought tolerance (% of WT) | Shoot DW d4 (g) |
|---|---|---|---|
| 34-1 | 125 ± 3 | 128% | 0.56 ± 0.01 |
| 97-7 | 140 ± 5 | 119% | 0.51 ± 0.02 |
| 94-10 | 150 ± 5 | 113% | 0.46 ± 0.02 |
| 65-1 | 153 ± 6 | 112% | 0.47 ± 0.02 |
| 30-2 | 162 ± 4 | 106% | 0.43 ± 0.01 |

TABLE 4-continued

Water loss relative to shoot dry weight and drought tolerance in 35S-bHLH39 transgenic lines

| Entry | Water lost in 3d/shoot DW d4 | Drought tolerance (% of WT) | Shoot DW d4 (g) |
|---|---|---|---|
| 1-7 | 166 ± 3 | 104% | 0.43 ± 0.01 |
| WT | 173 ± 5 | 100% | 0.40 ± 0.01 |

Example 12

Constitutive Expression of At-bHLH101 in *Arabidopsis* Results in Reduced Flower Abortion Following Heat Stress An experiment was set up with 17 transgenic 35S-AtbHLH101 lines and a WT control. Plants were grown in 2.25 inch pots under optimal conditions (22 C, 18 hr light of 200 uE, 60% RH) in a growth chamber until three days post-appearance of the first flower. A heat stress treatment was applied by placing plants at 42 C for 1.75 hours. One week following the stress period the plants were assessed for number of aborted flowers. The results are shown in Table 5 and show ten of the transgenic lines had at least 10% reduced flower abortion relative to WT controls and two lines had over 50% reduced flower abortion relative to WT controls.

TABLE 5

Flower abortion following heat stress (n = 12)

| Entry | # of aborted flowers | Flower abortion (% of WT) |
|---|---|---|
| 61-1 | 1.3 ± 0.3 | 41% |
| 88-3 | 1.3 ± 0.4 | 43% |
| 18-1 | 2.0 ± 0.5 | 65% |
| 90-1 | 2.3 ± 0.5 | 73% |
| 15-2 | 2.5 ± 0.5 | 81% |
| 49-5 | 2.5 ± 0.5 | 81% |
| 19-4 | 2.7 ± 0.4 | 86% |
| 70-8 | 2.7 ± 0.3 | 86% |
| 75-2 | 2.7 ± 0.5 | 86% |
| 16-2 | 2.8 ± 0.4 | 89% |
| 39-11 | 2.8 ± 0.4 | 92% |
| 11-1 | 2.9 ± 0.4 | 95% |
| 81-3 | 3.0 ± 0.4 | 97% |
| 79-6 | 3.1 ± 0.4 | 100% |
| 97-2 | 3.1 ± 0.4 | 100% |
| 45-2 | 3.2 ± 0.5 | 103% |
| 9-1 | 3.2 ± 0.4 | 103% |
| WT | 3.1 ± 0.3 | 100% |

Example 13

Constitutive Expression of AtbHLH101 in *Arabidopsis* Results in Drought Tolerance of the Plants Drought tolerance was assessed in ten transgenic At-bHLH101 lines that also showed reduced flower abortion following heat stress. Plants were grown (5 per 3 inch pot) under optimal conditions in a growth chamber (22 C, 18 hr light of 200 uE, 60% RH) until the first open flower. Drought treatment was applied then by watering up all plants to the same saturated level. Further water was withheld. Plants were weighed daily to determine the daily water loss and all plants were harvested on day four of treatment, at which time all plants were visibly wilting. The water loss relative to final shoot biomass was calculated and is a representative indicator of drought tolerance. Data was normalized to WT which was set as 100% (Table 6). Eight of the ten lines examined showed some degree of drought tolerance and one line had a statistically significant 27% greater drought tolerance relative to WT. This line was also one of the best four performing heat tolerant lines as seen by reduced flower abortion.

TABLE 6

Water loss relative to shoot dry weight and drought tolerance in 35S-bHLH101 transgenic lines

| entry | Water lost in 3d/shoot DW d4 | Drought tolerance (% WT) | Shoot DW d4 (g) |
|---|---|---|---|
| 90-1 | 147 ± 5 | 127% | 0.48 ± 0.02 |
| 16-2 | 174 ± 6 | 114% | 0.41 ± 0.02 |
| 61-1 | 176 ± 5 | 113% | 0.40 ± 0.01 |
| 70-8 | 177 ± 7 | 112% | 0.41 ± 0.02 |
| 6-5 | 181 ± 3 | 110% | 0.39 ± 0.01 |
| 11-1 | 187 ± 7 | 107% | 0.38 ± 0.02 |
| 45-2 | 189 ± 8 | 106% | 0.37 ± 0.02 |
| 19-4 | 191 ± 5 | 105% | 0.37 ± 0.01 |
| 79-6 | 203 ± 7 | 100% | 0.35 ± 0.01 |
| 82-4 | 203 ± 3 | 99% | 0.34 ± 0.01 |
| WT | 202 ± 6 | 100% | 0.34 ± 0.01 |

Example 14

Constitutive Expression of At-bHLH39 in *Arabidopsis* Results in Increased Seed Yield Relative to a Wild Type Control Following Heat Stress Plants are grown (3 per 3" pot) under optimal conditions in a growth chamber (22 C, 18 hr light of 200 uE, 60% RH) until flowering. At flowering plants are split into two groups where the first group is exposed to heat stress (all plants flowered within a couple of days) and the second group is maintained under optimal conditions until maturity. The heat stress treatment consists of a daily exposure to 45 C. Temperatures are ramped from 22 to 45 C over a one hour period and maintained at 45 C for a time period of 2 hr to 3 hr. Daily heat stress treatments are applied for a period of 10 days. Following the heat stress treatments plants are returned to optimal conditions and grown to maturity. All plants are harvested at maturity and final seed yield per pot is determined. By comparing the yield (as % of optimal) of transgenic plants to that of WT the degree of yield protection is calculated.

TABLE 7

SEQUENCE ID REFERENCE CHART

| SPECIES | SEQ ID NO: | bHLH | Reference | Seq. type | Length |
|---|---|---|---|---|---|
| ARABIDOPSIS THALIANA | 1 | bHLH39 | AT3G56980 | nucleotide | 777 |
| AVENA SATIVA | 2 | bHLH39 | CN817002 | nucleotide | 222 |
| BRACHYPODIUM DISTACHYON | 3 | bHLH39 | super_13.506_gen | nucleotide | 2091 |
| BRACHYPODIUM DISTACHYON | 4 | bHLH39 | super_13.506_cds | nucleotide | 729 |
| BRASSICA NAPUS | 5 | bHLH39 | EE515575 | nucleotide | 587 |
| BRASSICA NAPUS | 6 | bHLH39 | TC84782 | nucleotide | 595 |
| BRASSICA NAPUS | 7 | bHLH39 | TC88840 | nucleotide | 631 |
| BRASSICA RAPA | 8 | bHLH39 | Contig2 | nucleotide | 693 |
| GLYCINE MAX | 9 | bHLH39 | TC269627 | nucleotide | 723 |
| HORDEUM VULGARE | 10 | bHLH39 | AK251746 | nucleotide | 738 |
| PANICUM VIRGATUM | 11 | bHLH39 | Contig2 | nucleotide | 723 |
| SOLANUM LYCOPERSICUM | 12 | bHLH39 | DV105842 | nucleotide | 351 |
| TRITICUM AESTIVUM | 13 | bHLH39 | TC358765 | nucleotide | 714 |
| TRITICUM AESTIVUM | 14 | bHLH39 | TC343683 | nucleotide | 617 |
| TRITICUM AESTIVUM | 15 | bHLH39 | TC300244 | nucleotide | 434 |
| TRITICUM AESTIVUM | 16 | bHLH39 | CA618726 | nucleotide | 261 |
| ZEA MAYS | 17 | bHLH39 | TC429418 | nucleotide | 228 |
| ARABIDOPSIS THALIANA | 18 | bHLH39 | AT3G56980 | protein | 258 |
| AVENA SATIVA | 19 | bHLH39 | CN817002 | protein | 158 |
| BRACHYPODIUM DISTACHYON | 20 | bHLH39 | super_13.506_ORF | protein | 242 |

TABLE 7-continued

SEQUENCE ID REFERENCE CHART

| SPECIES | SEQ ID NO: | bHLH | Reference | Seq. type | Length |
|---|---|---|---|---|---|
| GLYCINE MAX | 21 | bHLH39 | TC269627 | protein | 241 |
| HORDEUM VULGARE | 22 | bHLH39 | AK251746 | protein | 246 |
| PANICUM VIRGATUM | 23 | bHLH39 | Contig2 | protein | 241 |
| SOLANUM LYCOPERSICUM | 24 | bHLH39 | DV105842 | protein | 117 |
| TRITICUM AESTIVUM | 25 | bHLH39 | TC358765 | protein | 238 |
| TRITICUM AESTIVUM | 26 | bHLH39 | TC343683 | protein | 206 |
| TRITICUM AESTIVUM | 27 | bHLH39 | TC300244 | protein | 144 |
| TRITICUM AESTIVUM | 28 | bHLH39 | CA618726 | protein | 87 |
| ARABIDOPSIS THALIANA | 29 | bHLH38 | AT3G56970 | nucleotide | 762 |
| BRASSICA NAPUS | 30 | bHLH38 | TC95626 | nucleotide | 753 |
| BRASSICA OLERACEA | 31 | bHLH38 | AM061155 | nucleotide | 765 |
| BRASSICA RAPA | 32 | bHLH38 | EX134222 | nucleotide | 435 |
| CICER ARIETINUM | 33 | bHLH38 | FE670123 | nucleotide | 300 |
| HORDEUM VULGARE | 34 | bHLH38 | TC164142 | nucleotide | 501 |
| HORDEUM VULGARE | 35 | bHLH38 | BAF30424.1 | nucleotide | 759 |
| MEDICAGO TRUNCATULA | 36 | bHLH38 | TC127269 | nucleotide | 767 |
| MEDICAGO TRUNCATULA | 37 | bHLH38 | TC115041 | nucleotide | 780 |
| MEDICAGO TRUNCATULA | 38 | bHLH38 | AJ496888 | nucleotide | 300 |
| PANICUM VIRGATUM | 39 | bHLH38 | Contig1 | nucleotide | 690 |
| POPULUS | 40 | bHLH38 | TC89850 | nucleotide | 549 |
| POPULUS | 41 | bHLH38 | EEF05011.1 | nucleotide | 795 |
| POPULUS | 42 | bHLH38 | EEE91492.1 | nucleotide | 474 |
| RICINUS COMMUNIS | 43 | bHLH38 | EEF30834 | nucleotide | 774 |
| RICINUS COMMUNIS | 44 | bHLH38 | EEF30835 | nucleotide | 555 |
| SOLANUM LYCOPERSICUM | 45 | bHLH38 | TC194645 | nucleotide | 717 |
| SORGHUM BICOLOR | 46 | bHLH38 | TC117663 | nucleotide | 642 |
| TRITICUM AESTIVUM | 47 | bHLH38 | TC337566 | nucleotide | 672 |
| TRITICUM AESTIVUM | 48 | bHLH38 | CA650144 | nucleotide | 390 |
| TRITICUM AESTIVUM | 49 | bHLH38 | CA502657 | nucleotide | 459 |
| VIGNA UNGUICULATA | 50 | bHLH38 | FF388259 | nucleotide | 732 |
| VITIS VINIFERA | 51 | bHLH38 | CAO17950.1 | nucleotide | 1563 |
| VITIS VINIFERA | 52 | bHLH38 | CAN79614 | nucleotide | 735 |
| ARABIDOPSIS THALIANA | 53 | bHLH38 | AT3G56970 | protein | 253 |
| BRASSICA NAPUS | 54 | bHLH38 | TC95626 | protein | 251 |
| BRASSICA OLERACEA | 55 | bHLH38 | AM061155 | protein | 255 |
| BRASSICA RAPA | 56 | bHLH38 | EX134222 | protein | 145 |
| CICER ARIETINUM | 57 | bHLH38 | FE670123 | protein | 100 |
| HORDEUM VULGARE | 58 | bHLH38 | TC164142 | protein | 167 |

TABLE 7-continued

SEQUENCE ID REFERENCE CHART

| SPECIES | SEQ ID NO: | bHLH | Reference | Seq. type | Length |
|---|---|---|---|---|---|
| HORDEUM VULGARE | 59 | bHLH38 | BAF30424.1 | protein | 252 |
| MEDICAGO TRUNCATULA | 60 | bHLH38 | TC127269 | protein | 246 |
| MEDICAGO TRUNCATULA | 61 | bHLH38 | TC115041 | protein | 260 |
| MEDICAGO TRUNCATULA | 62 | bHLH38 | AJ496888 | protein | 100 |
| ORYZA SATIVA | 63 | bHLH38 | NP_001045424.1 | protein | 247 |
| PANICUM VIRGATUM | 64 | bHLH38 | Contig1 | protein | 230 |
| POPULUS | 65 | bHLH38 | TC89850 | protein | 183 |
| POPULUS | 66 | bHLH38 | EEF05011.1 | protein | 264 |
| POPULUS | 67 | bHLH38 | EEE91492.1 | protein | 158 |
| RICINUS COMMUNIS | 68 | bHLH38 | EEF30834.1 | protein | 257 |
| RICINUS COMMUNIS | 69 | bHLH38 | EEF30835.1 | protein | 184 |
| SOLANUM LYCOPERSICUM | 70 | bHLH38 | TC194645 | protein | 239 |
| SORGHUM BICOLOR | 71 | bHLH38 | TC117663 | protein | 214 |
| TRITICUM AESTIVUM | 72 | bHLH38 | TC337566 | protein | 224 |
| TRITICUM AESTIVUM | 73 | bHLH38 | CA650144 | protein | 130 |
| TRITICUM AESTIVUM | 74 | bHLH38 | CA502657 | protein | 153 |
| VIGNA UNGUICULATA | 75 | bHLH38 | FF388259 | protein | 244 |
| VITIS VINIFERA | 76 | bHLH38 | CAN64266.1 | protein | 245 |
| VITIS VINIFERA | 77 | bHLH38 | CAO17950.1 | protein | 520 |
| VITIS VINIFERA | 78 | bHLH38 | CAN79614.1 | protein | 244 |
| ARABIDOPSIS THALIANA | 79 | bHLH101 | AT5G04150 | nucleotide | 723 |
| BRASSICA OLERACEA | 80 | bHLH101 | AM060621 | nucleotide | 546 |
| BRASSICA RAPA | 81 | bHLH101 | Contig1 | nucleotide | 678 |
| ORYZA SATIVA | 82 | bHLH101 | CI296230 | nucleotide | 261 |
| ORYZA SATIVA | 83 | bHLH101 | TC345105 | nucleotide | 450 |
| ARABIDOPSIS THALIANA | 84 | bHLH101 | AT5G04150 | protein | 240 |
| BRASSICA OLERACEA | 85 | bHLH101 | AM060621 | protein | 182 |
| BRASSICA RAPA | 86 | bHLH101 | Contig1 | protein | 226 |
| ORYZA SATIVA | 87 | bHLH101 | CI296230 | protein | 87 |
| ORYZA SATIVA | 88 | bHLH101 | TC345105 | protein | 150 |
| ARABIDOPSIS THALIANA | 89 | bHLH100_2 | AT2G41240.2 | nucleotide | 726 |
| ARABIDOPSIS THALIANA | 90 | bHLH100_1 | AT2G41240.1 | nucleotide | 729 |
| ORYZA SATIVA | 91 | bHLH100_1 | TC340917 | nucleotide | 621 |
| PANICUM VIRGATUM | 92 | bHLH100_1 | FL920216 | nucleotide | 711 |
| SORGHUM BICOLOR | 93 | bHLH100_1 | TC113263 | nucleotide | 732 |
| TRITICUM AESTIVUM | 94 | bHLH100_2 | TC317240 | nucleotide | 417 |
| TRITICUM AESTIVUM | 95 | bHLH100_1 | TC303529 | nucleotide | 705 |
| TRITICUM AESTIVUM | 96 | bHLH100_1 | CD865039 | nucleotide | 691 |

TABLE 7-continued

SEQUENCE ID REFERENCE CHART

| SPECIES | SEQ ID NO: | bHLH | Reference | Seq. type | Length |
|---|---|---|---|---|---|
| ZEA MAYS | 97 | bHLH100_1 | TC409749 | nucleotide | 465 |
| ARABIDOPSIS THALIANA | 98 | bHLH100_2 | AT2G41240.2 | protein | 241 |
| ARABIDOPSIS THALIANA | 99 | bHLH100_1 | AT2G41240.1 | protein | 242 |
| ORYZA SATIVA | 100 | bHLH100_1 | TC340917 | protein | 207 |
| PANICUM VIRGATUM | 101 | bHLH100_1 | FL920216 | protein | 237 |
| SORGHUM BICOLOR | 102 | bHLH100_1 | TC113263 | protein | 244 |
| TRITICUM AESTIVUM | 103 | bHLH100_2 | TC317240 | protein | 139 |
| TRITICUM AESTIVUM | 104 | bHLH100_1 | TC303529 | protein | 235 |
| ZEA MAYS | 105 | bHLH100_1 | TC409749 | protein | 155 |

Sequences

```
>SEQ ID NO: 1
ATGTGTGCATTAGTACCTCCATTGTTTCCAAACTTTGGGTGGCCATCAACGGGAGAGTACGACAGCTACTACCTCGC
CGGAGATATCCTCAACAACGGCGGGTTTCTTGATTTTCCGGTACCGGAGGAGACTTATGGAGCTGTTACAGCGGTGA
CTCAACATCAGAATAGCTTTGGTGTTTCTGTTTCGTCGGAGGGAAATGAAATAGACAACAATCCGGTGGTCGTCAAG
AAGCTTAATCACAATGCTAGTGAGCGTGACCGTCGCAGGAAAATTAACTCTTTGTTCTCATCTCTCCGTTCATGTCT
TCCTGCCTCTGGCCAATCGAAGAAGCTAAGCATTCCTGCGACGGTTTCTCGAAGCTTGAAGTACATACCAGAGCTGC
AAGAGCAAGTGAAGAAGCTAATAAAAAGAAGGAAGAGCTCTTGGTGCAAATTTCAGGTCAAAGAAACACTGAATGT
TACGTTAAGCAGCCACCAAAGGCCGTCGCGAATTATATCTCGACCGTTTCTGCGACTAGGCTTGGTGACAACGAAGT
GATGGTCCAAATCTCATCGTCCAAGATTCATAACTTTTCAATGTTTTAAGTGGGTTAGAAGAAGATAGGT
TTGTTCTTGTGGACATGTCATCTTCAAGGTCTCAAGGAGAAAGGCTTTTCTACACTTTGCATTTACAAGTGGAGAAG
ATTGAAAATTACAAGCTGAATTGCAAGAGTTAAGTCAGAGGATGTTGTACTTGTATGAGGAATGTGGAAACTCATA
TATATGA

>SEQ ID NO: 2
GCACGAGGCCTCCCTCCGCTCCCTCCTCCCCGACACCGATCACAGCAAGAAGCTGAGCATCCCCATCACTGTGACGC
GGGTGCTCAAGTACATCCCGGAGCTGCAGAAGCAGGTGGACACGCTGGAGAAGAAGAAGGAAGAGCTGACCCAGGCG
AACTGCAAACCAGGAGTTGTGGCCATGAAGGAGAACACGGCTCCGATCGTGTCCGCCACCTGCCTCGA

>SEQ ID NO: 3
ATGGGGCACAAGCAGCTGTTCGTGGACGACCCGTTCGCGAGCAGCATCTCGTCTCTGGAGGCGGAGGCCATCTTCTC
CGGCGCCGGCGGGCAGTGGCGCGCCGGCGGCGGCCTCGACGACCGTGACCTCTCCGCCATGCCGGCGGCGGCCAACA
CCTCGTCGGGCGGCTCCGGCTCTCCCGGCGGCGGCGGCAGGAAGATGAGCCACAACGCGTACGAGCGCGACCGCCGC
AAGCAGCTCAACGAGCTCTACTCCTCCCTCCGCTCCCTCCTCCCCGACGCCGACCACACCGTATGCAAATCAAATTG
AAGCCATAGATCATAATTTGATCCTGAATCCTGATGGATCTGGTGATGATTTGACTAATTGCAGAAGAAGCTGAGCA
TCCCGATCACAGTGTCGCGGGTGCTAAAGTACATCCCGGAGCTGCAGAAGGAAGTGGACGGGCTGGAGAGGAAGAAG
GAGGAGCTGACGCGCGCCAACTGCAAGCCCGGGGTGATCGCCATGAAGGACCAGAAGTTGCTCCCGTCGTCTCCGC
GACCTGCCTCGACGACAAGGACATCATGGTTCAGGTCAGCTTGCTCAGCGGCATGGCGGCGGCGGCTCTGCCGATGT
CCACGTGCATAAAGATTCTGGAGAACGAAGGTCTTCGCCTCGTCAGCTCGTCCACTTCTGCCTTTGGGAACAGGACG
TTCTATAACCTCCATCTTCAGGTAATTGGTACATCTGTCTGCATGAAGCCTTAATTTCCTATTGGTAATTATCAATG
TCATCGATCCATGCTTGCTCGATTCATTTTGGCAAATTTGCCTCATACTTACTCGACATCGTAGTAGAAGAGAAGGA
AAAAAAAAAGCCCAGCATTTTTCTTTGAGAAACAAAGCACAACATTTTCTGCTCCCAAGATCCATTCCGAAAGCCGG
GTGCACAACACTACGAGTAAAAATCGTTTCCTCTTAGTTATATAACGTGTGGTACCTTCAACTTAAATGAGCATCAG
TTGATGCAGAGTGGTACCCCTGTTCGGAAAAGACTTCAACATGGCACCATCTTCACTAGAGGTCCCCCAGCCCCTAA
TTCAGACGAAGGCATCATTTTAGTCCATTAACCCCGGTAGGTTGAGATTACAAAGGCTAGATTTATATAACGGTTTT
GCTATTTCTAAGGCGACTGAGAAATAAGTATTTCTAACAACCATTTGATCCAATCACTGAGATTCGTCAAGATCCA
TACATATACAAAGTATTAGAAAACCTTAATCGGATGGATATGATCGTTGACTGAGAATAGACACTTCTTTTATGTA
AAGGGTGTTTACTATATATATGTGGGTTTTGATATACTCATATTGAATAGATTTGAAGATCATGTCAGGCCCTACTT
AGGGTAATCTGTTGTGAAATTAAACTGTGTTCATAGGGCAAAAACATTGTCTTATAAATCAGCACAAAATCAACGAA
TTGGGAGTTTTTACGTAACAAATATAAATTGTAGCAACACAAATTAATTGGCTACAATACAATCCAAGAACAACAAG
ACGAGTATACACGGCAAACGATCATGCATATGGTGAGTTGGTGACCAGATCACCCGCTCTACTAGATGCTCCTAGAT
GCATATGGTGCCATAATTTTAGGAAAACCGAACTGGAAGAAGCACCTAAAAAACGAGTATGAAATCATCAATCGACC
AAGATTAGAGGTCGGTCTCATCATCGACAACATGAACAATTAAGATGCATGCTGGAGAACAGATAATCTAACACAGC
CACAGGTTTATTACAAAAAGCTTAACAGAAACTTCGCTAAAGCAACCAAAGAATGAGAACAAAAAATATATCTTCT
AATAACATGTGTGTGCTGTTGTATAGCATCTGAAGGCGTAATGCGAAACTCTAATTTATCTGAAGTATGTAGTGCTT
ATATGCTTATATAACATGTAAATAAGCAATATATATTCATTAATTTCATTTAATTTGTATACTGAAACAGAGAAACC
AGCGAACGATGAGCAAGGAGTGCCCAGCGTTCTGTGACGAGCTGGAGAAAGCCATCAAGAAAAGGCAGGACTGCAT
ATGCATCAGTGA

>SEQ ID NO: 4
ATGGGGCACAAGCAGCTGTTCGTGGACGACCCGTTCGCGAGCAGCATCTCGTCTCTGGAGGCGGAGGCCATCTTCTC
CGGCGCCGGCGGGCAGTGGCGCGCCGGCGGCGGCCTCGACGACCGTGACCTCTCCGCCATGCCGGCGGCGGCCAACA
```

```
CCTCGTCGGGCGGCTCCGGCTCTCCCGGCGGCGGCGGCAGGAAGATGAGCCACAACGCGTACGAGCGCGACCGCCGC
AAGCAGCTCAACGAGCTCTACTCCTCCCTCCGCTCCCTCCTCCCCGACGCCGACCACACCAAGAAGCTGAGCATCCC
GATCACAGTGTCGCGGGTGCTAAAGTACATCCCGGAGCTGCAGAAGGAAGTGGACGGGCTGGAGAGGAAGAAGGAGG
AGCTGACGCGCGCCAACTGCAAGCCCGGGGTGATCGCCATGAAGGACCAGAACGTTGCTCCCGTCGTCTCCGCGACC
TGCCTCGACGACAAGGACATCATGGTTCAGGTCAGCTTGCTCAGCGGCATGGCGGCGGCGGCTCTGCCGATGTCCAC
GTGCATAAAGATTCTGGAGAACGAAGGTCTTCGCCTCGTCAGCTCGTCCACTTCTGCCTTTGGGAACAGGACGTTCT
ATAACCTCCATCTTCAGAGAAACCAGCGAACGATGAGCAAGGAGTGCCCAGCGTTCTGTGACGAGCTGGAGAAAGCC
ATCAAGAAAAAGGCAGGACTGCATATGCATCAGTGA

>SEQ ID NO: 5
AAAAAAAAAATTAGAAAAGAAGAAAAGAGTTTATCGGGTCTCTCTCACGAGTCACGGCGTCGACGAAACTGGAGGTGA
AGCCATCTCCGATCGAGAGTCGCCGTCATCCCTATCCCACTCCTGCAATATCTACTCCGACGCTGTCGTCGTTAATT
TCGGCACCTCCTCGCCAAGTCGCCATCGTCCCTGTCGTGTGCGAGCTGTCACTGTCCATGCAACGAATAAATACTCT
GTGTCTGCATCGCTTTGACAGTGCTTGGTGCTTCTATGATATGTCCTCCGGTTTATGCTTTGCCCAGATTCGGAAGA
AGATGGGTTTGTTCTTGTTGATGTTTCATCTTCTAGGTCTCATGGAGAAAGGCTCGTCTACAGTTTGCATCTTCAAA
TGGGAAACATAAATAATCACGAGCTGACGTGCGAAGAGCTAAGCCAGAGAATGTATACTTGTATGAGGAATGCGGAA
ACTCGTTTAGATGATAATCTGTTCTTGTTTCTTTTAGTTATGTCATCTGTTTCTCAACATGTAACATTCATGTAGCC
GAGTTGTTTCGTTTATTTTTCTTGTCGAAATCAATGATCGATTATCGC

>SEQ ID NO: 6
GACGGCGTCGACGAAACTGGAGGTGAAGCCATCTCCGATCGAGAGTCGCCGTCATCCCTATCCCACTCCTGCAATAT
CTACTCCGACGCTGTCGTCGTTAATTTCGGCACCTCCTCGCCAAGTCGCCATCGTCCCTGTCGTGTAAGCCCTAGGT
CTGATTTGTCTTTCCTTTTAAATCGACGAAATTGAAATTGTGCGAGCTGTCACTGTCCATGCAACGAATAAATACTC
TGTGTCTGCATCGCTTTGACAGTGCTTGGTGCTTCTATGATATGTCCTCCGGTTTATGCTTTGCCCAGATTCGGAAG
AAGATGGGTTTGTTCTTGTTGATGTTTCATCTTCTAGGTCTCATGGAGAAAGGCTCGTCTACAGTTTGCATCTTCAA
ATGGGAAACATAAATAATCACGAGCTGACGTGCGAAGAGCTAAGCCAGAGAATGTATACTTGTATGAGGAATGCGGA
AACTCGTTTAGATGATAATCTGTTCTTGTTTCTTTTAGGTTATGTCATCTGTTTCTCAACATGTAACATTCATGTAG
CCGAGTTGTTTCGTTTATTTTCTTGTCGAAATTCAATGATCGATTATCACATTTAC

>SEQ ID NO: 7
GACGACAAAAAAAAAAATTAGAAAAGAAGAAAAGAGTTTATCGGGTCTCTCTCACGAGTCACGGCGTCGACGAAACT
GGAGGTGAAGCCATCTCCGATCGAGAGTCGCCGTCATCCCTATCCCACTCCTGCAATATCTACTCCGACGCTGTCGT
CGTTAATTTCGGCACCTCCTCGCCAAGTCGCCATCGTCCCTGTCGTAAGCCCTAGGTGCGAGCTGTCACTGTCCA
TGCAACGAATAAATACTCTGTGTCTGCATCGCTTTGACAGTGCTTGGTGCTTCTATGATATGTCCTCCGGTTTATGC
TTTGCCCAGATTCGGAAGAAGATGGGTTTGTTCTTGTTGATGTTTCATCTTCTAGGTCTCATGGAGAAAGGCTCGTC
TACAGTTTGCATCTTCAAATGGGAAACATAAATAATCACGAGCTGACGTGCGAAGAGCTAAGCCAGAGAATGTATAC
TTGTATGAGGAATGCGGAAACTCGTTTAGATGATAATCTGTTCTTGTTTCTTTTAGTTATGTCATCTGTTTCTCAAC
ATGTAACATTCATGTAGCCGAGTTGTTTCGTTTATTTTTCTTGTCGAAATCAATGATCGATTATCACATTTACATGCT
ACTGAATATTGACTG

>SEQ ID NO: 8
ACGACAAAAAAAAAATTAGAAAAGAAGAAAAGAGTTTATCGGGTCTCTCTCACGAGTCACGGCGTCGACGAAACTGGA
GGTGAAGCCATCTCCGATCGAGAGTCGCCGTCATCCCTATCCCACTCCTGCAATATCTACTCTGACGCTGTCGTCGT
TAATTTCGGCACCTCCTCGCCAAGTCGCCATCGTCCCTGTCGTAAGCCCTAGGTCTGATTTGTCTTTCCTTTTAA
ATCGACGAAATTGAAATTGTGCGAGCTGTCACTGTCCATGCAACGAATAAATACTCTGTGTCTGCATCGCTTTGACA
GTGCGTGGTGCTTCTATGATATGTCCTCTGGTTTATGCTTTGCCCAGATTCGGAAGAAGATGGGTTTGTTCTTTGTT
GATGTTTCATCTTCTAGGTCTCATGGAGAAAGGCTCGTCTACAGTTTGCATCTTCAAATGGGAAACATAAATAATCA
CGAGCTGACGTGCGAAGAGCTAAGCCAGAGAATGTATACCTGTATGAGGAATGCGGAAACTCGTTTAGATGATAATC
TGTTCTTGTTTCTTTTTGTTATGTCGTCTGTTTCTCAACATGTAACATTCATGTAGCCGAGTTGTTTCGTTTATTTT
CTTGTCGAAATCAATGATCGATTATCACATTTACATGCTACTGAATATTGACTGATTACTATGAAATTCACTAATAT

>SEQ ID NO: 9
ATGGTTGCTTTGTTTTCCCCTCCGGTGTTCTCAACCAAGGGATGGTTCTTAGAAGAAGAGCCATTAAGCTATGATGT
GTCTTCAGATTACTCATTTCCCTATCAATTTTTTGCACCACAGACACAGATTGAACTTGAAATAGAAAGGTCCTCTG
CACCATCCCCTGAAGACCCTGCCATGGTCAAAAAGCTTAGCCACAACGCTAGTGAACGTGATCGCCGCAAGAAGGTT
AATGACTTGGTTTCTTCACTTCGTTCACTTCTTCCTGGGCCAGATCAAACGAAAAAAATGAGCATTCCAGCTACAGT
TTCGCGAGTTTTAAAATACATACCTGAGTTACAACATCAAGTGCAAGCACTAACTAAGAAAAAGAGGAGCTTCTGT
GCAGAATTTCAAAAAATCTCAAAGGAGATTCGGTGAACAAAGAATCTCAAAGGAGAATTTCCCATCACAATTCTGAT
TTTGCTGTTTCAACTAGTAGGCTCAACGATTGTGAAGCTGTTGTTCACATTTCCTCTTATGAGGCTTCACAAGGCTCC
ACTATCCGACATCTTGCAATGTTTAGAAAATAATGGCCTTTATTTGCTAAATGCTTCTTCCTCTGAAACTTTTGGAG
GAAGGGTCTTCTACAACTTGCATTTCCAGGTGGAAAAAACTCATAGATTAGAGTCCGAAATTCTAACTGAGAAGCTT
TTGTCAATATATGAGAAGCAAAGGATTTTC

>SEQ ID NO: 10
ATGGGGCACCAGACCCAGATGTTCGACGACCCGTTCGCGAGCAGTATGTCGTCCCTGGACGCAGACATCTTCTCCGT
CGCCGGCGGCCTCCACCCATCGCAGTGGCCGGGACTCGACCACGACGTCTCGCTGGCGCCGGCTGCCAACAACGGCA
CCTCCTCCGGCGGCTACGGCTCCCCCGGGGGCGGCGATGGCTCGGGCTCCCACCGCAAGATCAGCCACAACGCGTAC
GAGCGCGACCGCCGCAAGCAGCTCAACGAGCTCTACTCCGACCTCCGCTCCCTCCTCCCCGACTCCGATCACACCAA
GAAGCTGAGCATTCCGATCACGGTGTCGCGGGTGCTCAAGTACATCCCGGAGCTGCAGAAGCAGGTGGACGGACTGG
AGAAGAAGAAGGAGGAGCTTACGAGGGCCAGCTGCAAGCCAGGCGTATTGACCATGAAGGAGAACACGGTCCCGATC
GTGTCCGCCACCTGCCTCGACGAAAGGGAGATCATGGTCAGGTTAGCTTGGTGAGCACCATGGCCGGAGCTCTGCC
CATGTCCAAGTGCATCAAAGTGCTGGAGAACGAAGGCCTCCGCCTCATCAGCTCGTCCACTTCTGCTTTCCAGAACA
GGACGTTCTATAGCCTCCATCTTCAGAGAACCCAACGGACGATGAGCAAAGAGTGTCCGGCATTTTGTGAAGAACTG
GAGAATGCCCTGACGCAGAAGGCGGGACTACGTCTACATCACCAG
```

Sequences

>SEQ ID NO: 11
ATGACCCCTTCTCGAGCAGCATCTCGTCGCTGGAGGCGGACATCTTCTCCGCCGGCGGCCAGCGGCGCGTCGCCGCC
GTGGCCGGACCTCGAACTCGACCTCGACCTCGACGACGACGACATCCACGACCTCTCCGCGCCGGCGGCCAACGCCA
CCTCCTCAGGAGGCTATGGCTCGGGCGGAGGCTCCGGCGGCTCCCACAGGAAGCTCAGCCACAACGCGTACGAGCGC
GACCGCCGGAAGCAGCTCAACGAGCTCTACTCCTCGCTCCGCTCCCTCCTCCCCGACGCTGACCACACTAAGAAGCT
GAGCATCCCCACCACGGTCTCCCGAGTTCTCAAGTACATCCCCGAGCTGCAGAAGCAGGTGGACAACCTGGAGAGGA
GGAAGAAGGAGCTGACGAACGCCAACTGCAAACCAGGAGTTCTGAAGACGAGCCAGATTGTAACTCCCATTGTTTCT
GCTACCTGCCTCAACGATACGGAGATCATGGTTCAGGTCAGCCTGCAGAGCAATGTGGCTGCCACAAGTCTTCCTCT
GTCCAAGTGCATAAAAGTGCTGGAGAACGAAGGCCTTCACCTGATTAGTTCATCAACTTACTCCACCTTCGACAACA
GGACATTCTATAGCCTCCATCTTCAGAGAAGTCAAAGAACGATGAAGGAGGAGTGCCCAGCATTCTGCGATGAACTG
GAGAGGATTATCAAGAAGAAAGCAGGGGCG

>SEQ ID NO: 12
ATGTTAGCCATTTCTTCTTCTTCTCCTCCTTTATTTTCTACTACTACTAATAATTTTGGTTGGCTTTTGGAAGATCT
TATAAGCCATGAATTAACAAATAGTGGAGAAACTTCAAATTCATCTCAAAAAAGCCTTCAACATTGTGATTCAAATA
AATTTGATCAAATTATTATCAACAGTGGTGATCAGTATCAACCTGATCAGACGGTTAAGAAGCTTAATCATAACGCA
AGTGAACGTGACCGTAGAAAGAAAATCAACAGCTTATATTCTTCTCTTCGTTCTTTACTACCTCCTTCTGATCATAC
GAAAAAGCTAAGCATTCCATCAACAGTATCAAGAATTCTAAAG

>SEQ ID NO: 13
ATGGGGCACCAGCACCAGATGTTCAACGACCCCTTCGCGAGCAGCATGTCGTCACTGGAGGAAGACATGTTCTCCGG
TGCCGGAGGCTACCACCACCTCACGCCGTCCATGCAGTGGCCGGGCTTGGATAACGACATACCGTCGGCGCCGGCTG
CCAACAACGCCACCTCCTCCGGTGGCTCTGGATCACACCGCAAGATGAGTCACAACGCGTACGAACGTGACCGCCGC
AAGCAGCTCAACGAGCAATATTCCTCCCTCCGCTCCCTCCTCCCCGACGATGATCACACCAAGAAGATGAGCATTCC
GACCACGGTGTCGCGGGTGATCAACTACATCCCGGAGCTGCAGAAGGAGGTAGACCGCCTGGAGAAGAAGAAGGAGG
AGCTGAGGCGGGCAGCTGCGAGCAAGGCGCCATGAGGCAGAACACGGCCCCGATCGTGTCCGCCACCTGCCTCGAC
GACAGGGAGATCATGGTCCAGGTCAGCCTGGTGAGCACCATGGCGGGAGCTCTGCCCATGTCCAAGTGCATCAAGGT
GCTGGAGAACCAAGGCCTTCGCCTCATAAATTCCTCGACTTCCGCGTTTCAGAACAGGACGTTCTACAGCCTCCATC
TTCAGAGAACCCAACGGACAATGAGCAAGGAGGGCCAAACATTTTGTAACGAATTGGAGAACGCTGTGAAGCAAAAG
GCGGGACTACATCTACATCAT

>SEQ ID NO: 14
ATGGGGCACCAGCACCAGATGTTCGAAGACCCGTTCGCGAGCAGCATATCGTCGCTGGAGGCCGAGATATTCTCCGT
CGCCGGCGGCCACCACCATACGCAGTGGCCGGGCCTCGACCACGACATCCCGCTGGCCCCGGCTGCCAATAACGGCA
CCTCCTCCGGCGGCTACGGCTCCCCGGGGGCGGCGATGGCTCGGGCTCCCATCGCAAGATCAGCCACAACGCCTAC
GAGCGCGACCGCCGCAAGCAGCTCAACGAGCTCTACTCCGACCTCCGCTCCCTCCTCCCCGACACCGATCACACGAA
GAAGCTTAGCATTCCGATCACGGTGTCGCGGGTGCTCAAGTACATCCCGGAGCTGCAGAAGCAGGTGGACGGCCTGG
AGAAGAAGAAGGAGGAGCTGACGCGCGCCAGCTGCAAGCCCGGCGTGCTGACCATGAAGGGGGACACGGCTCCGATC
GTGTCCGCCACTGCCTCGACGACAGGGAGATCATGGTCANNGTCAGCTGGTGAGCACCATGGGCGGAGTCTGCCA
TGTCAAGTGCTCAGGTGCTGAGACGAAGGCTCGGCTCATAGTCGTCACTCCGGTTCAGACAGACTCTATATTCATCT
C

>SEQ ID NO: 15
ATGGGGCACCAGCACCAGATGTTCGAAGACCCGTTCGCGAGCAGCATATCGTCGCTGGAGGCGGACATCTTCTCCGT
CGCCGCCGGCCACCACCATCCGCAGTGGCCGGGCCTCGACCACGACGTCCCGTTGGCGCCCGGCTGCCAACAACGGCA
CATCCTCCGGCGGCTACGGCTCCCCCGGTGGCGGCGACGGCTCGGGCTCCACCGCAAGATCAGCCACAACGCGTAC
GAGCGCGACCGCCGCAAGCAGCTCAACGAGCTCTACTCCGACCTCCGCTCCCTCCTCCCCGACACCGATCACACGAA
GAAACTGAGCATTCCGATCACGGTGTCGCGGGTGCTCAAGTACATCCCGGAGCTGCAGAAGCAGGTGGACGACTGG
AGAAGAAGAAGGAGGAGCTGACGCGCGCCAACTGCAGCCCGGCGTGCTG

>SEQ ID NO: 16
AACAACGCCACCTCCTCCGGCGGCTCTGGATCACACCGAAAGATGAGTCACAACGCGTACGAGCGTGACCGCCGCAA
GCAGCTCAACGAGCAATATTCCTCCCTCCGCTCCCTCCTCCCCGATGACGACCACAATAAGAAGATGAGCATTCCGA
CCACGGTGTCGCGGGTGATCAAGTACATCCCGGAGCTGCAGAAGGAGGTAGACGGCCTGGAGAAGAAGAAGGAGGAG
CTGAGGCGGGCCAGCTACGAGCAAGCGCCA

>SEQ ID NO: 17
CGTGTCCCGAGTTCTCAAGTACATCCCGGAGCTGCAGAAGCAGGTGGACAACCTGGAGAGGAGGAAGAAGGAGCTGA
CCAACGCCAACTGCAAGCCGGGAGTTCTGAAAACCACCAAGGCCGTAACTCCCATTGTTTCTGCTACCTGCCTCAAC
GACACGGAGATCATGGTTCAGGTCAGCCTGCACAGCGATGTGGCCGCACAGCTCTCCCTCTCTCCAAGTGCAT

>SEQ ID NO: 18
MCALVPPLFPNFGWPSTGEYDSYYLAGDILNNGGFLDFPVPEETYGAVTAVTQHQNSFGVSVSSEGNEIDNNPVVVK
KLNHNASERDRRRKINSLFSSLRSCLPASGQSKKLSIPATVSRSLKYIPELQEQVKKLIKKEELLVQISGQRNTEC
YVKQPPKAVANYISTVSATRLGDNEVMVQISSSKIHNFSISNVLSGLEEDRFVLVDMSSSRSQGERLFYTLHLQVEK
IENYKLNCEELSQRMLYLYEECGNSYI

>SEQ ID NO: 19
RHEASLRSLLPDTDHSKKLSIPITVTRVLKYIPELQKQVDTLEKKKEELTQANCKPGVVAMKENTAPIVSATCLDDR
DIMVQVSLLSNMAGALPVSKCIKVLENEGLRLVSSSTSAFQNKTFYSLHVQRTQRTISKVCPAFCDELENAIKRAGM
RLQQ

>SEQ ID NO: 20
MGHKQLFVDDPFASSISSLEAEAIFSGAGGQWRAGGGLDDRDLSAMPAAANTSSGGSGSPGGGGRKMSHNAYERDRR
KQLNELYSSLRSLLPDADHTKKLSIPITVSRVLKYIPELQKEVDGLERKKEELTRANCKPGVIAMKDQNVAPVVSAT
CLDDKDIMVQVSLLSGMAAAALPMSTCIKILENEGLRLVSSSTSAFGNRTFYNLHLQRNQRTMSKECPAFCDELEKA
IKKKAGLHMHQ

-continued

Sequences

>SEQ ID NO: 21
MVALFSPPVFSTKGWFLEEEPLSYDVSSDYSFPYQFFAPQTQIELEIERSSAPSPEDPAMVKKLSHNASERDRRKKV
NDLVSSLRSLLPGPDQTKKMSIPATVSRVLKYIPELQHQVQALTKKKEELLCRISKNLKGDSVNKESQRRISHHNSD
FAVSTSRLNDCEAVVHISSYEAHKAPLSDILQCLENNGLYLLNASSSETFGGRVFYNLHFQVEKTHRLESEILTEKL
LSIYEKQRIF

>SEQ ID NO: 22
MGHQTQMFDDPFASSMSSLDADIFSVAGGLHPSQWPGLDHDVSLAPAANNGTSSGGYGSPGGGDGSGSHRKISHNAY
ERDRRKQLNELYSDLRSLLPDSDHTKKLSIPITVSRVLKYIPELQKQVDGLEKKKEELTRASCKPGVLTMKENTVPI
VSATCLDEREIMVQVSLVSTMAGALPMSKCIKVLENEGLRLISSSTSAFQNRTFYSLHLQRTQRTMSKECPAFCEEL
ENALTQKAGLRLHHQ

>SEQ ID NO: 23
MTPSRAASRRWRRTSSPPAASGASPPWPDLELDLDLDDDDIHDLSAPAANATSSGGYGSGGGSGGSHRKLSHNAYER
DRRKQLNELYSSLRSLLPDADHTKKLSIPTTVSRVLKYIPELQKQVDNLERRKKELTNANCKPGVLKTSQIVTPIVS
ATCLNDTEIMVQVSLQSNVAATSLPLSKCIKVLENEGLHLISSSTYSTFDNRTFYSLHLQRSQRTMKEECPAFCDEL
ERIIKKKAGA

>SEQ ID NO: 24
MLAISSSSPPLFSTTTNNFGWLLEDLISHELTNSGETSNSSQKSLQHCDSNKFDQIIINSGDQYQPDQTVKKLNHNA
SERDRRKKINSLYSSLRSLLPPSDHTKKLSIPSTVSRILK

>SEQ ID NO: 25
MGHQHQMFNDPFASSMSSLEEDMFSGAGGYHHLTPSMQWPGLDNDIPSAPAANNATSSGGSGSHRKMSHNAYERDRR
KQLNEQYSSLRSLLPDDDHTKKMSIPTTVSRVINYIPELQKEVDRLEKKKEELRRGSCEQGAMRQNTAPIVSATCLD
DREIMVQVSLVSTMAGALPMSKCIKVLENQGLRLINSSTSAFQNRTFYSLHLQRTQRTMSKEGQTFCNELENAVKQK
AGLHLHH

>SEQ ID NO: 26
MGHQHQMFEDPFASSISSLEAEIFSVAGGHHHTQWPGLDHDIPLAPAANNGTSSGGYGSPGGGDGSGSHRKISHNAY
ERDRRKQLNELYSDLRSLLPDTDHTKKLSIPITVSRVLKYIPELQKQVDGLEKKKEELTRASCKPGVLTMKGDTAPI
VSXHCLDDREIMVXXQLVSTMGGVCHVKCSGAETKARLIVVTPVQTDSIFIS

>SEQ ID NO: 27
MGHQHQMFEDPFASSISSLEADIFSVAAGHHHPQWPGLDHDVPLAPAANNGTSSGGYGSPGGGDGSGSHRKISHNAY
ERDRRKQLNELYSDLRSLLPDTDHTKKLSIPITVSRVLKYIPELQKQVDGLEKKKEELTRANCSPAC

>SEQ ID NO: 28
NNATSSGGSGSHRKMSHNAYERDRRKQLNEQYSSLRSLLPDDDHNKKMSIPTTVSRVIKYIPELQKEVDGLEKKKEE
LRRASYEQAP

>SEQ ID NO: 29
ATGTGTGCATTAGTCCCTTCATTTTTCACAAACTTCGGTTGGCCGTCAACGAATCAATACGAAAGCTATTACGGTGC
CGGAGATAACCTAAATAACGGCACATTTCTTGAATTGACGGTACCACAGACTTATGAAGTGACTCATCATCAGAATA
GCTTGGGAGTATCTGTTTCGTCAGAAGGAAATGAGATAGACAACAATCCGGTTGTGGTCAAGAAGCTTAATCACAAT
GCTAGTGAACGTGACCGACGCAAGAAGATCAACACTTTGTTCTCATCTCTCCGTTCATGTCTTCCAGCTTCTGATCA
ATCGAAGAAGCTAAGTATTCCTGAAACGGTTTCAAAGAGCTTAAAGTACATACCAGAGCTGCAACAGCAAGTGAAGA
GGCTAATACAAAAGAAGGAAGAATTTTGGTACGAGTATCGGGTCAAAGAGACTTTGAGCTTTACGATAAGCAGCAA
CCAAAGGCGGTCGCGAGTTATCTCTCAACGGTTTCTGCCACTAGGCTTGGTGACAACGAAGTGATGGTCCAAGTCTC
ATCGTCCAAGATTCATAACTTTTCGATATCAAATGTGTTGGGTGGGATAGAAGAAGATGGGTTTGTTCTTGTGGATG
TTTCATCATCAAGATCTCAAGGAGAGAGGCTCTTCTACACTTTGCATCTTCAAGTGGAGAATATGGATGATTACAAG
ATTAATTGCGAAGAATTAAGTGAAAGGATGTTGTACTTGTACGAGAAATGTGAAAACTCGTTTAACTAG

>SEQ ID NO: 30
ATGTGTGCATTAGTCCCTCCATTGTTCCCAAACTTTGGGTGGCCGTCGACAGGAGAGTACGAGAGTAACTACCTGGC
CGGAGTGAACCTCGAGGACTTTACGTTTCTTGATTTTCCGGCACCAGAGACATATGGAGTGGAACATCATCAGGAGA
TTCAGGAAATGTTGGGGGTCTCTGTTCCGTCCGAGGGGAATGGAGTTGTAACCAAGAAGCTTAATCACAATGCTAGT
GAGCGTGACCGTCGCAAGAAGATCAACTCTTTGTTCTCGTCTCTCCGTTCATGTCTCCCAGCTTCTGATCAAACGAA
GAAGCTAAGTATTCCTCAGACGGTTTCTCGGAGCTTGAAGTACATTCCAGAGCTGCAAGAGCAAGTGAAGAAGCTAA
TACAAAAGAAGGAAGAACTCTTGGTGCGAGTATCAGGTCAAAGAGCCATTGAACATTATGTTGAGCCGCAGCCAAAG
GCCGTTGCACGTTACGTCTCGACCATTTCTGCGACTAAGCTTGGAGACAACGAAGTGCTGGTCCAAATCTCATCGTC
CAAGAATCATAACTTTTCGATATCTAATGTGTTGAGTGGGTTAGAAGAAGATGGGTTGTTCTTGTTGATGTTTCAT
CTTCCAGGTATCATGGAAAATGGCTCTTCTACTCTTTGCATCTTCAAATGGGAAATAAAGATAATCACAAACTGAAG
TGCGAAGAGCTAAGCCAGAGAATTTTGTACTTGTATGAGGAATGTGAAAACTCATTTAGA

>SEQ ID NO: 31
ATGTGTGCATTAGTCCCTCCACTGTTCCCCGACTTTGGGTGGCCGTCGACGGCAGGTTACGAGAGCTACTACCTCGG
CGGAGAAAACCTCAACAACGACATGTTTCTTGATTTTCCGGTTGTGGAAACTTATGGAGTATTGGCTCATCATCAGA
ACAGCTTAGGAGTTTCTGTTTCGTCGGAGGGAAATGGAATAGACAACAACCCGGTTGTTAAAAAGAAGCTTAATCAC
AATGCTAGTGAGCGTGACCGTCGCAAGAAGATCAACTCTTTGTTTTGCATCTCTCCGCTCATGTCTTCCAACCTCAGA
TCAATCGAAAAGCTAAGCATTTCAGCCACCGTTTCACGAAGCTTGAAGTACATACCAGAGTTGCAAGAGCAAGTGA
AGAAGTTATTACAAAAGAAGGAAGAACTCTTGGTTCGAGTATCAGGTCAACGAGACATTGAACTTTACGTTAAGCCA
CAACCAAAGGCAATTGCAAGTTATGTCTCCACTGTTTCCGCGACTAGGCTTGGAGACAACGAAGTGATGGTCCAAAT
CTCATCATCCAAGATTCATAACTTCTCGATATCTAAAGTGTTAACTGGGTTAGAAGAAGATGGTTTTGTTCTTGTGG
ATGTTTCATCTTCAAGGTTTCAAGGGGAAAGGCTTTTCTACACTTTGCATCTTCAAGTAGAAATATGGATGATCAT
TACAAAAATGAATTGCGAAGAGTTAAGTGAAAGGATGTTGTACTTGTACGAGGAATGTGAAAATTNNNTTAGG

| Sequences |
|---|
| >SEQ ID NO: 32<br>ATTCCTCAGACGGTTTCTCGGAGCTTGAAGTACATACCAGAGCTACAAGAGCAAGTGAAGAAGCTAATACAAAAGAA<br>GGAAGAACTCTTGGTGCGAGTATCAGGTCAAAGAGACATTGAACATTACGTTGGTGCCGCCACCCAAAGGCCGTTGCAC<br>GTTACGTCTCGACCATTTCTGCGACTAAGCTTGGAGACAACGAAGTGATGGTCCAAATCTCATCGTCCAAGAATCAT<br>AACTTTTCGATATCTAATGTGTTGAGTGGGTTAGAAGAAGATGGGTTTGTTCTTGTTGATGTTTCATCTTCAAGGTC<br>TCATGGAGAAAGGCTCTTCTACACTTTGCATCTTCAAATGGGAAATAAAGATGATTACAAACTGACATGCGAAGAGC<br>TACGCCAGAGAATGTTATACTTGTATGAGGAATGTGGAAACTCGTTTAGA<br><br>>SEQ ID NO: 33<br>ATTCCAACTCCCTCACAAGCCACAAGCAGCGACCTTAGCATGGTCAAGAAACTTATCCGCAATGCTAGTGAACGAGA<br>TCGCCGCAAGAAAATCAATACTTTGTATTCTTCACTTCGTTCACTTCTTCCTGTGGCAGAACAGATGAAGAAGTTGA<br>GCAATCCGGCAACAATTTCACGAGTCCTAAAGTACATACGTGAGTTACAGAAGCAGGTAGAAGGACTACTTACGAGA<br>AAGGAGGCGATTTTATTGAAACTATCTCCAGAAGTAGATGAGGTGAAGAGTAAAGAATCTGAGAGGAAG<br><br>>SEQ ID NO: 34<br>AGCGACCGCCGCAAGCAGCTCAACGAGCAATATTCCTCCCTCCGCTCCCTCCTCCCCGATGACGATCACAATAAGAA<br>GATGAGCATTCCGACCACGGTGTCGCGGGTGATCAAGTACATCCCGGAGCTACAGAAGGAGGTCGACGGTCTGGAGA<br>AGAAGAAGGAGGAGCTCAGGCGAGCTAGCAGCGAGCAAGGCGTGCTGACTATGAGGCAGAACACGGCTCCTGTCGTC<br>TCCGCCACCTGCCTCGACGACAGGGAAATCATGGTCCAGGTCAGTCTGGTGAGCACCATGGCCGCAGCTCTGCCCAT<br>GTCCAAGTGCATCAAGGTGCTGGAGAACGAAGGCCTTCGCCTCCATAAATTCCTCGACTTCCGCGTTCAGAACAGGA<br>CCTTCTATAGCCTCCATCTTCAGAGAACCCAACGAACAATGAGCAAGGAGGGCCAAACATTTTGTAACGAACTGGAG<br>AACGCCGTGAAGCAAAAGGCAGGACTGCATCTGCATCAT<br><br>>SEQ ID NO: 35<br>ATGGGGCACCAGACCCAGATGTTCGACGACCCGTTCGCGAGCAGTATGTCGTCCCTGGACGCAGACATCTTCTCCGT<br>CGCCGGCGGCCTCCACCCATCGCAGTGGCCGGGACTCGACCACGACGTCTCGCTGGCGCCGGCTGCCAACAACGGCA<br>CCTCCTCCGGCGGCTACGGCTCCCCCGGGGGCGGCGATGGCTCGGGCTCCCACCGCAAGATCAGCCACAACGCGTAC<br>GAGCGCGACCGCCGCAAGCAGCTCAACGAGCTCTACTCCGACGCTCCGCTCCCTCCTCCCCGACTCCGATCACACCAA<br>GAAGCTGAGCATTCCGATCACGGTGTCGCGCGTGCTCAAGTACATCCCGGAGCTGCAGAAGCAGGTCGGACGGACTGG<br>AGAAGAAGAAGGAGGAGCTTACGCGGGCCAGCTGCAAGCCAGGCGTATTGACCATGAAGGAGAACACGGTCCCGATC<br>GTGTCCGCCACCTGCCTCGACGAAAGGGAGATCATGGTCCAGGTTAGCTTGGTGAGCACCATGGCCGGAGCTCTGCC<br>CATGTCCAAGCGCATCAAAGTGCTGGAGAACGAAGGCCTCCGCCTCATCAGCTCGTCCACTTCTGCTTTCCAGAACA<br>GGACGTTCTATAGCCTCCATCTTCAGAGAACCCAACGGACGATGAGCAAAGAGTGTCCGGCATTTTGTGAAGAACTG<br>GAGAATGCCCTGACGCAGAAGGCGGGGTACGTCTACATCACCAGTAGATTATATGTAGCAGAATAA<br><br>>SEQ ID NO: 36<br>ATGTTAGCGATATCTCCTCCTATGTTTTCAACAATTGGATGGCCCTTTGAGGAGCCTTTAAGCCATAACCAGCATCA<br>GAATTCATTCTACAAAGACACTGTTGATCAATTATTTAATTTTCATGATCAAGTTGAGGCAGAAATTAATTCAACAG<br>ATCCCTCACAATCCACAAGCAGTGACCTTAGCATGGTCAAGAAGCTTGTTCATAATGCCAGTGAACGCGATCGCCGC<br>AAGAAGATCAATAATTTGTATTCATCACTTCGATCACTCCTTCCTGTTTCTGATCAAATGAAATTAAGCATTCCGGG<br>AACAATTTCTAGAGTCCTGAAATACATACCTGAATTACAGAATCAAGTAGAGGGACTAATTAAGAGAAAGGATGAGA<br>TCTTATTGGGACTTTCTCCACAAGTAGAAGAGTTTATTCTAAGCAAAGAATCTCAAAGGAAGAAGCATAGTTACAAC<br>TCTGGTTTTGTAGTTTCAAGTAGTAGGCTCAATGATAGTGAAATTACCATTCAGATTTCATGTTACACTGTCCAAAA<br>GATTCCACTTTCTGAGATCTTGATTTGTTTGGAAAATGATGGCCTTTTGCTGCTTAATGTTTCTTCATCAAAGACCT<br>TTGGAGGGAGGGTCTTCTATAATTTGCATTTCCAGGTGGATAAAACACAGATATTAGAATCTCATATTCTAAATGAG<br>AAGCTCTTATCAATAATGGAGAAGGAAGGAGAGTTTTTAAAACAATAATTAAAGTTTAGGATTTGGCTCTTTAA<br><br>>SEQ ID NO: 37<br>ATGGTTGCATTCTGCCCACCTCAGTTCTCATACTCAAACATGGGATGGCTCTTAGAGGAGTTAGAGCCAGAGTCCTT<br>AATTAGTCATAAAGAGAAGAACTATGCATCTTTAGAGTACTCGTTACCGTATCATCAATTCTCTTCACCAAAGGAAC<br>ATGTTGAAATTGAAAGGCCACCATCCCCTAAACTTATGGCCAAGAAACTTAACCACAATGCTAGTGAACGTGATCGC<br>CGCAAGAAGATTAATAGCTTGATTTCTTCACTTCGTTCACTTCTTCCCGGTGAAGATCAAACGAAAAAAATGAGCAT<br>TCCGGTAACAATTTCACGTGTCTTAAAATACATCCCTGATTTACAAAAGCAGGTGCAAGGACTTACCAAGAAAAAG<br>AAGAGCTTCTATCAAGAATTTCTCATCGACAAGAATATGCAGTTAACAAAGAATCACAAAGGAAGAAAATTCCAAAT<br>TACAATTCTGCTTTTGTAGTTTCAACAAGTAGGCTTAATGATACTGAGCTTGTTATTCATATTTCGTCTTATGAGGC<br>CAACAAGATTCCTCTATCTGAGATCTTGATGTGTTTAGAAAATAATGGTCTTCTTCTACTTAACTCTTCTTCTTCTA<br>AAACCTTTGGAGGGAGGCTCTTCTATAACTTGCATTTTCAGGTGGATAAAACTCAAAGATATGAGTGTGATGATCTG<br>ATTCAAAAGCTTTCTTCAATATATGAGAAGCAGCAAAATAATCATTTGGGCACTATGGATCAAACGATCAATAGTGG<br>TCTGATATAT<br><br>>SEQ ID NO: 38<br>ATGTTAGCGATATCTCCTCCTATGTTTTCAACAATTGGATGGCCCTTTGAGGAGCCTTTAAGCCATAACCAGCATCA<br>GAATTCATTCTACAAAGACACTGTTGATCAATTATTTAATTTTCATGATCAAGTTGAGGCAGAAATTAATTCAACAG<br>ATCCCTCACAATCCACAAGCAGTGACCTTAGCATGGTCAAGAAGCTTGTTCATTATGCCAGTGAACGCGATCGCCGC<br>AAGAAGATCAATAATTTGTATTCACACTTCGATCACTCCTTCCTGTTTCTGATCAAATGGTACTTAAT<br><br>>SEQ ID NO: 39<br>ATGGAGCACCAGCTGTTCGATGACCCCTTCTCTAGCAGCATCTCGTCGCTGGAGGCGGACATCTTCTCCGCCGGCGG<br>CCAGCTGCCGTCGCCGCCGTGGCCGGACCTCGACCTCGACCTCGACGACGACGACATCCACGACCTCTCCGCGCCGA<br>CCGGCAACCCCACCTCCTCAGGAGGCTATGGCTCGGGCGGAGGCTCCGGAGGCTCCGAGGAAGCACAGCCACAAC<br>GCGTACGAGCGCGACCGCCGGAAGCAGCTCAACGAGCTCTACTCCTCGCTCCGCTCCCTCCTCCCCGACGCTGACCA<br>CACTAAGAAGCTGAGCATCCCCACCACGTGTCTCCCGAGTTCTCAAGTACATCCCCGAGCTGCAGAAGCAGGTGGACA<br>ACCTGGAGAGGAGGAAGAAAGAGCTGACGAACGCCAACTGCAAACCAGGAGTTCTGAACACGAGCCAGATTGTAACT<br>CCCATTGTTTCTGCTACTTGCCTCAACGATACGGAGATCATGGTTCAGGTCAGCCTGCACAGCAACGTGGCTGCCAC<br>AAGTCTTCCTCTGTCCAAGTGCATAAAAGTGATGGAGAATGAAGGCCTTCACCTAATTAGTTCATCAACTTACTCCA<br>CCTTCGACAACAGGACATTCTATAGCCTCCATGTTCAGAGAAGTCAAAGAACGATGAAAGAGGAGTGCCCAGCA |

Sequences

>SEQ ID NO: 40
ATGGTCAAGAAACTTAGCCACAACGCTAATGAACGTGACCGTCGCAAGAAGATTAAAAGTTTGTATTCTTCACTTCG
TTCACTTCTCCCAGCAGCAGATCAAATGAAGAAATTAAGCGTGCCGGCCACTGTTTCACGTGCGCTTAAGTACCTAC
CAGAGCTTCAACAGCAAGTGGAGAGACTGGTTCAAAGAAAGGAGGAGCTTTTATCAAAGTTATCAAAGCAAGGTGGT
ATAATTCATCAAGAAATCAAAGAAATGACACCGTGTATAGCTCTTTATCATCGGTATCGGCAAGCCAGCTTAGTGA
TAGAGAAGTTGTCGTTCATATTTCCACTTACAAGAACCATAAAAGTCCATTATCAGAAATCTTGCTCACCTTAGAGG
AAGATGGACTTGTTCTAAAAAACTCTTCTTCCTTTGAGTCATTTGGGGACAGGGTCTTCTATAATTTACATCTTCAG
GTCATGGAAGGAACTTACACATTGGATAGTGAGGCCATGAGGGCGAAGCTTGTGTCTTTATCTGTAAAGAGGGAATC
ATCGTCTCTA

>SEQ ID NO: 41
ATGTTAGAAGAATTATCTCCCATCAGTTTGTTCTCAACATTTGGATGGCCCTTGGAGGAAGCCATAAGCCATGAACA
GCACTACAGCTTTAGAGATGGTGAAACTCCAGAGTCATTTACTCACTTCCCTCCATCTCAGCCAGATGTAAGACAGC
TTGATCGCTCCACATCATTCACGGCCCACAGTGGAAGCGGTGACCCTAGCATGGCTAAGAAGCTTAACCACAACGCT
AGCGAACGTGACCGTCGCAAAAAGATCAACAGTTTGTATTCTTCACTCCGTTCACTACTTCCTGCAGCCGATCAAAG
GAAGAAATTAAGCATACCGTATACAGTTTCACGTGTGCTTGTATACATACCAAAACTTCAACAACAAGTGGAGAGAC
TGATTCAAAGGAAGGAGGAGCTTCTATCGAAGTTATCTAGGCAAGCTGACGATTTAACTCATCAAGAAAATCAAAGA
AAAGGCACCATGTATAGCTCTTTATCATCGGTATCGGCGAGCCGGCTCAGTGACAGGGAAGTTGTCATTCATATCTC
AACTAACAAGCTCCATAGAAGTTCATTATCAGAAATCTTGGTTAATTTAGAGGAGGCTGGACTTCTTCTACTAAATT
CTTCTTCCTTCGAGTCCTTTGGAGGCAGAGTCTTCTATAATTTACACCTTCAGGCCATGGAAGGAACTTACACAGTA
GAGTGCGAGGCCTTGAATGAGAGGCTTGTGTCCTTGTGCGAGAAGAGGGAGTCATTGTTTCCATTAAATTCAAGTTC
TCCATATTCTAACTGTGTATTCTAG

>SEQ ID NO: 42
GATCCTAACATGGTTAAGAAGCTTAACCACAACGCTAGCGAACGTGATCGTCGCAAGAAGATCAACAGTTTGTATTC
TTCACTCCGTTCACTTCTTCCAGCTTCCGATGGAATGAAGAAATTAAGCATACCGTCCACAATTTCACGTGTGCTTA
AGTACATACCAGAACTTCAACAGCAAGTGGAGAGACAGATCCAAAGGAAGGAGGAGCTTCTATCAAATCTATCTCGG
CAAGATGATTTAATTCATCAAGAAAATCAAAGAAAAGACACCGTGTATAGCTCTTTATCATCGGTATCGGCAAGCCG
GCTTGGTGATAGAGAAGTTGTCGTTCAAATTTCCACTTGCAAGGTCCTTAAAAAGCCCAATATCAGAAATCTTGCTTA
ATTTAGAGGAAAATGGACTTGTTCTAATAAATTCTTCTTCCTTTGAGTCCTTTGGAGGCAACGTCTTCTACCATTTA
CATCTTCAGGTA

>SEQ ID NO: 43
ATGTTAGCATTATCTCCTCCTGTATTTCCAACACCTGAATGGCCCTTAGAGGACCCCTTAGGCATTGACCAAATCTC
CTACTTCTGTAGAGAAACTCAGCCTGCTACTGCTGCTTTTCTTCCATCTTATCAGCAAGAGTTATTATTATTAGAGC
TTGATCATCAACAATCCACATCTTTCACAGCCTATAATAGCAGTGGTGGTGACGCTAACGATATGGTGAAGAAGCTT
AATCATAATGCAAGCGAACGTGATCGTCGCAAGAAGATGAACACCCTCTATTCTTCCCTCCGATCACTATTTCCGGC
CGCCGATGAAATGAAGAAGCTGAGTATACCTGCCACAATTTCGAGGGTGTTGAAGTACATACCAGAACTACAAGAAC
AGTTAGAGAGATTGGTCCAAAGGAAGGAAGAGATTTTGCTAAGAATATCTAAGCAAAATCATATTGTTAATCCCCAA
ATAAACCAAAGAAAAGGCACTTCTCACAGCAGTTTATCAGTAGTATCAGCTAATCAAATTAGTGACAAAGAAGCCAT
TATTCAAATTTCTACGTACAGTAATACTATCCATACAAGTCCACTATCAGAAATCTTGCTTCTTTTGGAGGAGGAAG
GCCTTCTTTTGATTAATTCTTCTTCCGCTGAATCCTTTGGTGGCAGGGTCTTCAACAATTTACATGTTCAGGTTGAT
GATACTTATACATTGGAATGTGATGCTTTAAGTGAGAAGCTTGCATCTCTGTATGCCAAGAGGGACGGGCTGTTCCC
ATGA

>SEQ ID NO: 44
ATGGTCAAGAAGCTTAATCATAATGCAAGCGAAAGGGATCGCCGCAAGAAGATGAACACTCTCTATTCTTCCCTCCG
ATCACTTCTTCCGGCCTCCGATCAAATGAAGAAGCTGAGCATACCTGCCACAATTTCCAGGGTGTTGAAGTACATAC
CAGAACTACAACAACAATTGGAGAGATTCGTCCAAAGGAAAGAAGATATTACTGAGAATATCTAAGCAGAATCAT
ATTATTAATCCCCAAATAAACCAAAGAAAAGGCACTACTCACAGCACCTTATCAGTAGTATCAGCTAATCAAATTAG
TGACAAAGAAGTTGTTATTCAAGTTTCTACTTACAATAATACTATCCATACAAGTCCATTATCAGAAATCTTGCTTC
TTCTGGAGGAGGAAGGCCTTCTTCTGATTAATTCTTCCTCCTTTGAGTCCTTTGGAGGCAGGGTCTTCTACAATTTA
CATCTTCAGGTTGATGGAACTTATATATTGGAGTGTGATGCTTTAAGCGAGAAGCTTGCAGCTTTATATGAGAGAGA
CGGGTTATTTCCATGA

>SEQ ID NO: 45
ACAACGATAATAACTACGCCTCAATTTCAAACTGATCAGAATAACAAGTTGTTTGAAGGTTTACGTGCCGATAATAC
TATTGATTTACCTTCATCTCATCATTATCAACAACAATGTTTGAAAGGAAGTGAGTTTGATGTTGATGAGTTAGGGG
TAGAAAGGTCATTAATGGAGAAGAAGCTAAATCATAATGCAAGTGAACGTAATAGAAGGAAGAAGATGAATTTTCTT
TATTCAACTCTTCGTTCTTTGCTTCCTCCTCCTACTAATAAACATCAAAAGAAAAAATTAAGCTTTCCAGCAACAGT
ATCATATGTACAAGAATACATCCCAGAGTTGAAGAAGAAATAGAGGGCTAAGCAAAACAAAAGATTTGCTTTTAT
CAAAGAAATCAAATTATTCATTACTCAAAATTGATGATAATAATAAGAGAAAATTAATTATTGGTGGAACTTCTTGT
AATTCTTCAACAACATCAATTTGTGCAAGTCAACTAAGTAATTCACAAGTTTTGGTACAAATTTCAACAACTCAAGA
AAATAATTTTCCAATTTCACAAGTATTTGCAAGTGTAGAGGAAGATGGATTAATTTTGCTAAATGCATCATCCTTTA
AATCTTTTGGAGACAAGATTTTTCACAGCTTGCATTTTCAGATGCAAGGACCAATTGAAATGGACATTCAGGTTTTG
AAGACTAAGCTTTTAGTAATGTGT

>SEQ ID NO: 46
ATGGACCATCAGCTGTTCGACGACCCCTTCGGGAGCAGCATCTCGTCGCTGGAGGCGGACATCTTCTCCGCCGGCGG
CGGCGGACAGCTGCCGTCGCCGCCGTGGCCGGACCTCGACCTCGACGACGACTACGACATACACGACCTCTCCGCGC
CGGCCGCCAACGCCGCCACCTCCTCGGGAGGAGGCTATGGCTCCGGCGGCTCCGGCCAGGAAGCTCAGCCACAACGCA
TACGAGCGCGACCGCCGGAAGCAGCTCAACGAGCTCTACTCCTCGCTCCGATCCCTCCTCCCGGACGCTGATCACAC
TAAGAAGCTGAGCATCCCCACCACCGTGTCCCGAGTTCTCAACACCAAAGAGATCGTAACTCCCATTGTTTCTGCTA
CTTGCCTTAACGACACGGAGATCATGGTTCAGGTCAGCCTGCACAGCAATGTGGCCGCCACAGCTCTCCCTCTCTCC
AAGTGCATAAAGGTGCTAGAAAACGAAGGCCTTCCTCGTCAGCTCATCAACCTACTCCACCTTCGAGAACAAGAC
ATTCTATAGCCTCCATCTTCAGAGAAGTCAAAGAACGATGAAGGAGCAGTGCCCAGGATTCTGCGACGAACTGGAGA
AGATCGTCAGGAAGAAAGCAGGGGCG

Sequences

>SEQ ID NO: 47
ATGGAGCATCAACTATTCGACGACGCCGTCCCGAGCAGCATGATCTGGCCGTTAGAGGCAGAAAACGGTTTCACCGA
CGAGCTGCCGTCTTTGCAGTTACCGGACGTGGACCTTGACTTCGACATCCACGAGTTCTCCGCACCGGCAACGGCAC
CGGCGAAAGCGGCCTCCTCGGGTGGCTCCGGATTGGTTGGTTCCGGTTCAGGATCGCATAAGAAGCTCAACCACAAC
GCGTACGAGCGCGACCGGCGGACGCAGCTCAATCAGCTCTACTCGACTCTCCGTTCTCTCATCCCCAACGCAGATCA
CACAAAGAAGCTGAGCATTCCGACGACGGTGTGTCAGGTCCTCGACTACATACCCAAGCTGCAGAAGCAGGTCGAGG
ATCTCAAGAAGAAGAAACAGGAGCTCAGTACAGCCAAATGCAGAGAAAGACTGCAGCGCGTCAAGGACAACACATGC
CGTATTGTTTCTGCCACTCCTCTCGATGGCAACGAAATCATGGTCCAGGTTAGCCTGCTGAGCAACATGGCTGCAAG
TCTTCCTCTATCCAAGTGCATAAACGTATTTGAGAACAAAGGGCTTCACCTCATCAGTTCATCGACTTTCTCCACCG
AGGTCAATAGAACATTTTACAGCTTCCACTTTGAGGTACGTTTTTACATGCGCCCT

>SEQ ID NO: 48
GGCGATGGCTCGGGCTCCCATCGCAAGATCAGCCACAACGCCTACGAGCGCGACCGCCGCAAGCAGCTCAACGAGCT
CTACTCCGACCTCCGCTCCCTCCTCCCCGACACCGATCACACGAAGAAGCTTAGCATTCCGATCACGGTGTCGCGGG
TGCTCAAGTACATCCCGGAGCTGCAGAAGCAGTGGGCTTGNAGAAANAAAGAAGGAGGAGNTGACGCGCGCCAACTG
CAACCCGGNGTGNTGACCATGAAGGGGAACACGGTCCGATTGTTCCGCCACCTGCCTCGACGACAGGGANATTATGG
TCCAAGTCAACCTGGTGAGCACATGGCCGGANTNTGCCCATTTCAAATGCATCAAAGTGCTGGAAAACAANNGCTCC
GGTCA

>SEQ ID NO: 49
ATGGAGCAGCTGTTCGTCGACGACCCAGCCTTCGCGAGCAGCATGTCGTCGCTTGAGGCGGACATCTTCTCCGGCGC
CGGCCAGCTGCCGTCCTCGCCGTGGCTGGACCTAGACCTCGACGACGATGTCCAAGACCTCTCCATGGCGCCGACGA
CGGCGAACGCGGTGTCCTCCGGCTACGGCTCCGGCGGATCCGGCTCCCACAGGAAGCTCAGCCACAACGCCTACGAG
CGCGACCGCCGGAAGCAGCTCAACGAGCTCTACTCCTCCCTCCGCAGCTCTCCTCCCCGACGCCGATCACACTAAGAA
GCTGAGCATCCCGACGACGGTGTCTCGCGTGCTCAAATACATACCCGAGCTGCAGAAGCAGGTGGAGAATCTGGACA
GGAAGAAGAAGGAGCTGACGACGACGAGCACCACCAACTGCCAACCAAGAGTGTTGGGGAGCCAGCTGATGAGC

>SEQ ID NO: 50
ATGGTCGCATTGTTCTCTCCTCCTCTCTTCTCAACCAAAGGGTGGCTCTTAGAGGAGGAGCCATTCGGCTATAATAA
TACCCATAATCTCTCCTACAAAGATGATGCGTCTTCTCAGTACTCCTTTCCCTATCAATTTTATTCACCACAGACAC
AGATTGAGGTTGAAATTGAAAGGTCCACTGCACCATCCTCTGACCCTGCCATGGTCAAGAAACTTAGCCACAATGCT
AGCGAACGTGATCGCCGCAAGAAGGTCAACAACTTGGTTTCTTCACTTCGTCTCACTTCTTCCAATGGCAGATCAAAC
GAAAAAAATGAGCATTCCTGCAACAGTTTCCAGAGTGTTGAAATACATACCTGAACTACAACAGCAAGTGCAAGCAC
TAACAAAGAGAAAGAGGAGCTTCTGTGCAGAATTTCTCGGCAATTGCAAGGAGAAGCAGTGAACAAGAATCTCAG
AGAAAAATTTCCCATCACAACTCTTCTTTTGTTGTCTCAACGACTAGGCTTAACGATTGTGAAGCTGTAGTTCACAT
TTCATCTCATGAGACACAAGGCTCCACTATCAGAGATTCTGCAGTGCTTAGAAAATGATGGCCTTTTTCTGCTAC
ATGCTTCTTCCTCAGAAACCTTTGGAGGAAGGTTCTTCTACAATTTGCATTTTCACGTGGAGAAAACTGATAGATTA
GAGACCGAGATTTTAACTGAGAAGCTTTTACCAATATAT

>SEQ ID NO: 51
ATGTTAGCATTCTCCCCTCCATTGTTTCCAACCCTTGGATGGCCCTTGGAGGATCCCATAAGCCATGCACAGAACTA
CATATATGGAGAAACAGAAACTTCAGAATCGTTTCTTCACTTGCCCTCATCTCAGCCACAAGTGGAACTCAATTGCT
CCACCCCATATGCAGCAGTTAGTGGTAATCCCACGATGGTTAAGAAACTTAACCACAACGTCAGTGTGCGGGATCGT
CGGAAGAAGATCAACAGCTTGTACTCCTCTCTGCGTTCACTACTTCCATCAGCTGATCAAGTGAAGAAATTAAGCAT
TCCTTCGACAGTTTCATGTGTGCTAAAATACATACCAGAGCTGCAACGGCTGCAACGGCAGATGGAGAGACTGATCCAAAAGAAAG
AAGAGTTTTTATCAAAGATTTCTAGGGAAGGAGATCTAATTCACCTAGAAAATCAAAGAAATGGCACACTTGGAAGC
TCTTTATCTGCTGTTTCAGCAAGAAGGCTTAGTGACAGGGAAATTGTGGTTCAGATATCCACATTTAAGGTCCATGA
GAGTCCACTTTCTGAGGTTTTGTTAAATTTGGAGGAGGATGGGCTTCTTGTAATCAATGCATCATCTTTTGAGTCCT
TTGGAGGGAGGGTCTTCTACAACTTACATCTTCAGGTTGAAGGAACTCAAGGAATGGAGTCGACCGCCCACTTGGAG
ATGACAAGAACTCTAAAAAACAAACACATGAATATATTGGTGATTCATATGGACTTTCCTCCTTTTTTCTTAAGAT
GTTCCTGATCTTTACAAGAGTATTTACCAATCATATATCAACTTCCTACCAATGCTATGTTGGTAAATTAATTATCA
TTTCTACTGCTACATGTAATTAAGAAAGAAAATTTTGAAACTTCTAAACATCAATTGGCCAGCGCCGAACCAATAATT
GTAGCAGGTCAAGCTGCCAAAAAATTGGATGATGAGCTTCTCTTGGAAACCAAGATGAAAACTGAAGGGATGGGAGT
ACTGGAAACACCAATATTGATTAAAGCAAAGAATGGTACCAAAGAAATGGTGGAGAGAATCCTTGATCTTTACCCCA
TGCAATTCATGACATAGACTCCAACAAGAAGAATATAGTGCTATTGGCGGTGGAGAATAGGCACCCCCATGTGTAT
GAGCTCTTCCTGAAGAGAAATATTGTGAAAGATAGTGTATTTGGTGCAGTTGATAATAAAGGCAACAGTGCATTGCA
TCTGGCTGCCATGTTTGCAGATTATCGGCCTTGGGTCACTCCTGGTTGCAAATGCAATGGGAAGTCAAAT
GGTATGAGTATGTGAAGAAGTCCATGCCACCCAAATTTCTTCCGTTTCCACAACAATGAAAACAAGTCTACAAAGCAG
ATTTTCACCCGTGAACACAGAGATCTGGTGCAAAAGGGTGGGCAATGGCTAAATAACACAGCCACCTCATGCTCGTT
GGTAGTAACACTCATTGCAACAGTTGCCTTCGCCACATCAACTGCTGTACCGGGCGGCACCAAGGAGGGGACTGATT
CATGTCCTCTCAATGGTCCCTAA

>SEQ ID NO: 52
ATGTTAGCATTCTCCCCTCCATTGTTTCCAACCCTTGGATGGCCCTTGGAGGATCCCATAAGCCATGCACAGAACTA
CATATATGGAGAAACAGAAACTTCAGAATCGTTTCTTCACTTGTCCTCATCTCAGCCACAAGTGGAACTCAATTGCT
CCACCCCATCTGCAGCAGTTAGTGGTAATCCCACGATGGTTAAGAAACTTAACCACAACGTCAGTGCGCGGGATCGT
CGGAAGAAGATCAACAGCTTGTACTCCTCTATGCGTTCACTACTTCCATCAGCTGATCAAGNGAAGAAATTAAGCAT
TCCTTCGACAGTTTCACGTGTGCTAAAATACATACCAGAACTGCAACGACAAGTGGAGAGATTGATTCAAAAGAAAG
AAGAGTTTTTATCAAAGATTTGTAGGGAAGGAGATCCAATTCACCTAGAAAATCAAAGAAATGGCACACTTGGAAGC
TCTTTATCTGCTGTTTCAGCAAGAAGGCTTAGTGACAGGGAAATTGTGGTTCAGATATCCACATTTAATGTCCATGA
GAGTCCTCTTTCTGAGGTTTTGTTAAATTTGGAGGAGGATGGGCTTCTTGTAATCAATGCATCATCTTTTGAGTCCT
TTGGAGGGAGGGTCTTCTACAAACTTACATCTTCAGGTTGAAGGAACTCAAGGAATGGAGTGTGAGTTGTTGAGCGAG
AAGCTACTTTCATTGTGTGAAAGGAGAGAGGCTTTTCCATGA

>SEQ ID NO: 53
MCALVPSFFTNFGWPSTNQYESYYGAGDNLNNGTFLELTVPQTYEVTHHQNSLGVSVSSEGNEIDNNPVVVKKLNHN
ASERDRRKKINTLFSSLRSCLPASDQSKKLSIPETVSKSLKYIPELQQQVKRLIQKKEEILVRVSGQRDFELYDKQQ

| Sequences |
| --- |
| PKAVASYLSTVSATRLGDNEVMVQVSSSKIHNFSISNVLGGIEEDGFVLVDVSSSRSQGERLFYTLHLQVENMDDYK<br>INCEELSERMLYLYEKCENSFN<br><br>>SEQ ID NO: 54<br>MCALVPPLFPNFGWPSTGEYESNYLAGVNLEDFTFLDFPAPETYGVEHHQEIQEMLGVSVPSEGNGVVTKKLNHNAS<br>ERDRRKKINSLFSSLRSCLPASDQTKKLSIPQTVSRSLKYIPELQEQVKKLIQKKEELLVRVSGQRAIEHYVEPQPK<br>AVARYVSTISATKLGDNEVLVQISSSKNHNFSISNVLSGLEEDGFVLVDVSSSRYHGKWLFYSLHLQMGNKDNHKLK<br>CEELSQRILYLYEECENSFR<br><br>>SEQ ID NO: 55<br>MCALVPPLFPDFGWPSTAGYESYYLGGENLNNDMFLDFPVVETYGVLAHHQNSLGVSVSSEGNGIDNNPVVKKKLNH<br>NASERDRRKKINSLFASLRSCLPTSDQSKKLSISATVSRSLKYIPELQEQVKKLLQKKEELLVRVSGQRDIELYVKP<br>QPKAIASYVSTVSATRLGDNEVMVQISSSKIHNFSISKVLTGLEEDGFVLVDVSSSRFQGERLFYTLHLQVENMDDH<br>YKMNCEELSERMLYLYEECENXXR<br><br>>SEQ ID NO: 56<br>IPQTVSRSLKYIPELQEQVKKLIQKKEELLVRVSGQRDIEHYVEPHPKAVARYVSTISATKLGDNEVMVQISSSKNH<br>NFSISNVLSGLEEDGFVLVDVSSSRHGERLFYTLHLQMGNKDDYKLTCEELRQRMLYLYEECGNSFR<br><br>>SEQ ID NO: 57<br>IPTPSQATSSDLSMVKKLIRNASERDRRKKINTLYSSLRSLLPVAEQMKKLSNPATISRVLKYIRELQKQVEGLLTR<br>KEAILLKLSPEVDEVKSKESERK<br><br>>SEQ ID NO: 58<br>SDRRKQLNEQYSSLRSLLPDDDHNKKMSIPTTVSRVIKYIPELQKEVDGLEKKKEELRRASSEQGVLTMRQNTAPVV<br>SATCLDDREIMVQVSLVSTMAAALPMSKCIKVLENEGLRLINSSTSAFQNRTFYSLHLQRTQRTMSKEGQTFCNELE<br>NAVKQKAGLHLHH<br><br>>SEQ ID NO: 59<br>MGHQTQMFDDPFASSMSSLDADIFSVAGGLHPSQWPGLDHDVSLAPAANNGTSSGGYGSPGGGDGSGSHRKISHNAY<br>ERDRRKQLNELYSDLRSLLPDSDHTKKLSIPITVSRVLKYIPELQKQVDGLEKKKEELTRASCKPGVLTMKENTVPI<br>VSATCLDEREIMVQVSLVSTMAGALPMSKRIKVLENEGLRLISSSTSAFQNRTFYSLHLQRTQRTMSKECPAFCEEL<br>ENALTQKAGYVYITSRLYVAE<br><br>>SEQ ID NO: 60<br>MLAISPPMFSTIGWPFEEPLSHNQHQNSFYKDTVDQLFNFHDQVEAEINSTDPSQSTSSDLSMVKKLVHNASERDRR<br>KKINNLYSSLRSLLPVSDQMKLSIPGTISRVLKYIPELQNQVEGLIKRKDEILLGLSPQVEEFILSKESQRKKHSYN<br>SGFVVSSSRLNDSEITIQISCYTVQKIPLSEILICLENDGLLLLNVSSSKTFGGRVFYNLHFQVDKTQILESHILNE<br>KLLSIMEKEGEFLKQ<br><br>>SEQ ID NO: 61<br>MVAFCPPQFSYSNMGWLLEELEPESLISHKEKNYASLEYSLPYHQFSSPKEHVEIERPPSPKLMAKKLNHNASERDR<br>RKKINSLISSLRSLLPGEDQTKKMSIPVTISRVLKYIPDLQKQVQGLTKKKEELLSRISHRQEYAVNKESQRKKIPN<br>YNSAFVVSTSRLNDTELVIHISSYEANKIPLSEILMCLENNGLLLLNSSSSKTFGGRLFYNLHFQVDKTQRYECDDL<br>IQKLSSIYEKQQNNHLGTMDQTINSGLIY<br><br>>SEQ ID NO: 62<br>MLAISPPMFSTIGWPFEEPLSHNQHQNSFYKDTVDQLFNFHDQVEAEINSTDPSQSTSSDLSMVKKLVHYASERDRR<br>KKINNLYSSLRSLLPVSDQMVLN<br><br>>SEQ ID NO: 63<br>MEQLFVDDPAFASSMSSLEADIFSGAGQLPSSPWLDLDLDDDVQDLSMAPTTANAVSSGYGSGGSGSHRKLSHNAYE<br>RDRRKQLNELYSSLRALLPDADHTKLSIPTTVSRVLKYIPELQKQVENLERKKKELTTTSTTNCKPGVLGSQLMSEG<br>MAPIVSATCINDMEIMVQVSLLSNVAGSVLPLSKCIKVLENEGLHFISSSTSSGFGNRTFYSIHLQRSEGTINEECP<br>AFCERLEKVVRNKAKL<br><br>>SEQ ID NO: 64<br>MEHQLFDDPFSSSISSLEADIFSAGGQLPSPPWPDLDLDLDDDDIHDLSAPTGNPTSSGGYGSGGGSGGSHRKHSHN<br>AYERDRRKQLNELYSSLRSLLPDADHTKKLSIPTTVSRVLKYIPELQKQVDNLERRKKELTNANCKPGVLNTSQIVT<br>PIVSATCLNDTEIMVQVSLHSNVAATSLPLSKCIKVMENEGLHLISSSTYSTFDNRTFYSLHVQRSQRTMKEECPA<br><br>>SEQ ID NO: 65<br>MVKKLSHNANERDRRKKIKSLYSSLRSLLPAADQMKKLSVPATVSRALKYLPELQQQVERLVQRKEELLSKLSKQGG<br>IIHQENQRNDTVYSSLSSVSASQLSDREVVVHISTYKNHKSPLSEILLTLEEDGLVLKNSSSFESFGDRVFYNLHLQ<br>VMEGTYTLDSEAMRAKLVSLSVKRESSSL<br><br>>SEQ ID NO: 66<br>MLEELSPISLFSTFGWPLEEAISHEQHYSFRDGETPESFTHFPPSQPDVRQLDRSTSFTAHSGSGDPSMAKKLNHNA<br>SERDRRKKINSLYSSLRSLLPAADQRKKLSIPYTVSRVLVYIPKLQQQVERLIQRKEELLSKLSRQADDLTHQENQR<br>KGTMYSSLSSVSASRLSDREVVIHISTNKLHRSSLSEILVNLEEAGLLLLNSSSFESFGGRVFYNLHLQAMEGTYTV<br>ECEALNERLVSLCEKRESLFPLNSSSPYSNCVF<br><br>>SEQ ID NO: 67<br>DPNMVKKLNHNASERDRRKKINSLYSSLRSLLPASDGMKKLSIPSTISRVLKYIPELQQQVERQIQRKEELLSNLSR<br>QDDLIHQENQRKDTMYSSLSSVSASRLGDREVVVQISTCKVLKSPISEILLNLEENGLVLINSSSFESFGGNVFYHL<br>HLQV |

| Sequences |
| --- |
| >SEQ ID NO: 68<br>MLALSPPVFPTPEWPLEDPLGIDQISYFCRETQPATAAFLPSYQQELLLLELDHQQSTSFTAYNSSGGDANDMVKKL<br>NHNASERDRRKKMNTLYSSLRSLFPAADEMKKLSIPATISRVLKYIPELQEQLERLVQRKEEILLRISKQNHIVNPQ<br>INQRKGTSHSSLSVVSANQISDKEAIIQISTYSNTIHTSPLSEILLLLEEEGLLLINSSSAESFGGRVFNNLHVQVD<br>DTYTLECDALSEKLASLYAKRDGLFP<br><br>>SEQ ID NO: 69<br>MVKKLNHNASERDRRKKMNTLYSSLRSLLPASDQMKKLSIPATISRVLKYIPELQQQLERFVQRKEELLLRISKQNH<br>IINPQINQRKGTTHSTLSVVSANQISDKEVVIQVSTYNNTIHTSPLSEILLLLEEEGLLLINSSSFESFGGRVFYNL<br>HLQVDGTYILECDALSEKLAALYERDGLFP<br><br>>SEQ ID NO: 70<br>TTIITTPQFQTDQNNKLFEGLRADNTIDLPSSHHYQQQCLKGSEFDVDELGVERSLMEKKLNHNASERNRRKKMNFL<br>YSTLRSLLPPPTNKHQKKKLSFPATVSYVQEYIPELKKEIERLSKTKDLLLSKKSNYSLLKIDDNNKRKLIIGGTSC<br>NSSTTSICASQLSNSQVLVQISTTQENNFPISQVFASVEEDGLILLNASSFKSFGDKIFHSLHFQMQGPIEMDIQVL<br>KTKLLVMC<br><br>>SEQ ID NO: 71<br>MDHQLFDDPFGSSISSLEADIFSAGGGGQLPSPPWPDLDLDDDYDIHDLSAPAANAATSSGGGYGSGGSGRKLSHNA<br>YERDRRKQLNELYSSLRSLLPDADHTKKLSIPTTVSRVLNTKEIVTPIVSATCLNDTEIMVQVSLHSNVAATALPLS<br>KCIKVLENEGLLLVSSSTYSTFENKTFYSLHLQRSQRTMKEQCPGFCDELEKIVRKKAGA<br><br>>SEQ ID NO: 72<br>MEHQLFDDAVPSSMIWPLEAENGFTDELPSLQLPDVDLDFDIHEFSAPATAPAKAASSGGSGLVGSGSGSHKKLNHN<br>AYERDRRTQLNQLYSTLRSLIPNADHTKKLSIPTTVCQVLDYIPKLQKQVEDLKKKKQELSTAKCRERLQRVKDNTC<br>RIVSATPLDGNEIMVQVSLLSNMAASLPLSKCINVFENKGLHLISSSTFSTEVNRTFYSFHFEVRFYMRP<br><br>>SEQ ID NO: 73<br>GDGSGSHRKISHNAYERDRRKQLNELYSDLRSLLPDTDHTKKLSIPITVSRVLKYIPELQKQWAXRXKEGGXDARQL<br>QPGVXTMKGNTVRLFRHLPRRQGXYGPSQPGEHMAGXCPFQMHQSAGKQXLRS<br><br>>SEQ ID NO: 74<br>MEQLFVDDPAFASSMSSLEADIFSGAGQLPSSPWLDLDLDDDVQDLSMAPTTANAVSSGYGSGGSGSHRKLSHNAYE<br>RDRRKQLNELYSSLRALLPDADHTKKLSIPTTVSRVLKYIPELQKQVENLERKKKELTTTSTTNCQPRVLGSQLMS<br><br>>SEQ ID NO: 75<br>MVALFSPPLFSTKGWLLEEEPFGYNNTHNLSYKDDASSQYSFPYQFYSPQTQIEVEIERSTAPSSDPAMVKKLSHNA<br>SERDRRKKVNNLVSSLRSLLPMADQTKKMSIPATVSRVLKYIPELQQQVQALTKRKEELLCRISRQLQGEAVNKESQ<br>RKISHHNSSFVVSTTRLNDCEAVVHISSHETHKAPLSEILQCLENDGLFLLHASSSETFGGRFFYNLHFHVEKTDRL<br>ETEILTEKLLPIY<br><br>>SEQ ID NO: 76<br>MLAFSPPLFSTFGWPWEDPXSHEQNYIYQETEASESFLHLPSSEPQAELNYSTPSAAVSGNPTMVKKLNHNASERDR<br>RKKINSLYSSLRSLLPAADQAKKLSIPSTVSRVLKYIPELQKQVERLIQKKEELLSKISRQGDIIHQEKQRKATLAS<br>SLSAVSANRLSDREIVVQISTFKVHESPLSEVLLNLEEDGLLVINASSFESFGGRVFYNLHLQVEGTHRMECEVLSE<br>KLLSLCEKRRDAFP<br><br>>SEQ ID NO: 77<br>MLAFSPPLFPTLGWPLEDPISHAQNYIYGETETSESFLHLPSSQPQVELNCSTPYAAVSGNPTMVKKLNHNVSRDR<br>RKKINSLYSSLRSLLPSADQVKKLSIPSTVSCVLKYIPELQRQVERLIQKKEEFLSKISREGDLIHLENQRNGTLGS<br>SLSAVSARRLSDREIVVQISTFKVHESPLSEVLLNLEEDGLLVINASSFESFGGRVFYNLHLQVEGTQGMESTAHLE<br>MTRTLKNKHMNILVIHMDFPPPFLKMFLIFTRVFTNHISTSYQCYVGKLIIILLLHVIKKENFETSKHQLASAEPII<br>VAGQAAKKLDDELLLETKMKTEGMGVLETPILIKAKNGTKEMVERILDLYPMAIHDIDSNKKNIVLLAVENRHPVY<br>ELFLKRNIVKDSVFGAVDNKGNSALHLAAMFADYRPWVTPGVALQMQWEVKWYEYVKKSMPPNFFRFHNNENKSTKQ<br>IFTREHRDLVQKGGQWLNNTATSCSLVVTLIATVAFATSTAVPGGTKEGTDSCPLNGP<br><br>>SEQ ID NO: 78<br>MLAFSPPLFPTLGWPLEDPISHAQNYIYGETETSESFLHLSSSQPQVELNCSTPSAAVSGNPTMVKKLNHNASERDR<br>RKKINSLYSSMRSLLPSADQXKKLSIPSTVSRVLKYIPELQRQVERLIQKKEEFLSKICREGDPIHLENQRNGTLGS<br>SLSAVSARRLSDREIVVQISTFNVHESPLSEVLLNLEEDGLLVINASSFESFGGRVFYNLHLQVEGTQGMECELLSE<br>KLLSLCERREAFP<br><br>>SEQ ID NO: 79<br>ATGGAGTATCCATGGCTGCAGTCTCAAGTTCATTCCTTTTCACCTACTCTCCATTTTCCTTCCTTCCTTCATCCTTT<br>AGATGATTCCAAGAGCCATAACATCAATCTTCATCATATGAGTCTTAGTCACAGCAATAATACTAACAGTAACAATA<br>ACAATTATCAAGAAGAAGATCGAGGAGCGGTGGTTTTGGAGAAGAAACTGAATCACAACGCAAGCGAACGAGACCGC<br>CGTAGAAAACTTAACGCCTTGTACTCTTCACTTCGTGCTCTCTTGCCTCTTTCTGATCAAAAGAGGAAGCTGAGCAT<br>TCCTATGACGGTAGCGAGAGTAGTGAAATACATACCAGAGCAGAAGCAAGAACTTCAACGTTTGTCTCGGAGAAAAG<br>AAGAGCTCTTGAAGAGGATCTGAGAAAAACTCACCAAGAGCAGCTGAGAAACAAAGCAATGATGGACTCAATAGAT<br>TCTTCTTCCTCTCAACGGATCGCAGCAAATTGGCTCACTGACACAGAGATTGCTGTCCAGATTGCTACGTCGAAATG<br>GACATCTGTTTCAGACATGTTGCTTAGGTTAGAAGAAAACGGGCTTAATGTCATAAGCGTCTCTTCTTCCGTTTCTT<br>CCACCGCAAGGATCTTCTACACTCTACATCTTCAGATGAGAGGAGATTGCAAAGTGAGACTGGAGGAACTCATCAAT<br>GGTATGCTCTTGGGATTACGCCAATCATAA<br><br>>SEQ ID NO: 80<br>ATGTGTGCCTTAACACCAATGTTTCCAAGTAACCAACAAGAATGGTACTCTACTTCAACAATGGAGTATCCATGGCT<br>TGATTCCTTCTCTCCTACTCTCCCTTCTTCTCTTTATCCTTCTTTCGACCAACTAGATGAATTCAAGAGCTATAACA |

-continued

Sequences

TCAATCTTCTTCCTCATCATATGAATCTTGCTGACATAAATGGTACTAACAATGATCAAGAAGAACATCAAGGATCG
GTTTTGGAAAAGAAACTGAATCACAACGCAAGTGAACGCGACCGCCGTAGAAAGCTAAACGCCTTATACGCTTCACT
TCGTGCTCTCTTGCCTCCTTCTGATCAAAAGAGAAAGTTGAGCATTCCAAAGACCATAGCGGGAGTGGTGAAGTATA
TACCAGAGCAGAAGCAAGAACTTCAACGTTTGTCTAGGAGGAAAGAAGAGCTTATGAAGAGAATCTCCAATAAGACA
GAGACTTTGAATCATCAACAAGAACAGCTGAGAAATAGAGCATTAATGATGGAGTCAATAGATTCTTCTTCACAAAA
GATCGCT

>SEQ ID NO: 81
ATGGAGTATCCATGGCTTGATTCCTTCTCTCCTACTCTCCCTTCTTCTCTTTATCCTTCTTTCGACCAACTAGATGA
ATTCAAGAACTATAACATCAATCTTCTTCCTCATCATATGAATCTTGCCGACATAAATGGTACTAACAATACCAGTA
ACAATGATCAAGAAGAACATCAAGGATCGGTTTTGGAAAAGAAAACTGAATCACAACGCAAGTGAACGCGACCGCGT
AGAAAGCTAAACGCCTTATACGCTTCACTTCGTGCTCTCTTGCCTCCTTCTGATCAAAAGTCGGCGAATCAGAGAAA
GTTGAGCATTCCAAAGACCGTAGCGGGAGTGGTGAAGTATATACCAGAGCAGAAGCAAGAACTTCAACGTTTGTATA
GGAGGAAAGAAGAGCTTATGAAGAGGATCTCCAATAAGATAGAGACTTTGAATCATCAACAAGAACAGCTGAGAAAT
AGAGCATTAATGATGGAGTCAATAGATTCTTCTTCACAAAAGATCGCTGCAAATTGGATCACCAACACAGAAATAGC
TGTCCAGATTGCTACATGGAAATGGACATCTATCTCAGACATGTTGCTTAGGTTAGAAGAAAACGGGCTTAATGTCA
TAAGCGTCTCTTCTTCGGTTTCTTCCACCGCAAGGATCTTCTACACACTGCATCTTCAGATG

>SEQ ID NO: 82
GCTTTCTCTTTCAGCTCGATCGATCCACAGCTCAACGAGCTCTACTCCTCCCTCCGCGCTCTCCTCCCCGACGCCGA
TCACACTAAGAAGCTGAGCATCCCGACGACGGTGTCTCGCGTGCTCAAGTACATACCCGAGCTGCAGAAGCAGGTGG
AGAATCTGGAGAGGAAGAAGAAGGAGCTGACGACGAGCACCACCAACTGCAAACCAGGAGTGTTGGGGAGCCAG
CTGATGAGCGAGGGCATGGCTCCCATCGTT

>SEQ ID NO: 83
ATGGAGCAGCTGTTCGTCGACGACCCAGCCTTCGCGAGCAGCATGTCGTCGCTTGAGGCGGACATCTTCTCCGGCGC
CGGCCAGCTGCCGTCCTCGCCGTGGCTGGACCTAGACCTCGACGACGATGTCCAAGACCTCTCCATGGCGCCGACGA
CGGCGAACGCCGGTGTCCTCCGGCTACGGCTTCGGCGGATCCGGCTCCCACAGGAAGCTCAGCCACAACGCCTACGAG
CGCGACCGCCGGAAGCAGCTCAACGAGCTCTACTCCTCCCTCCGCGCTCTCCTCCCCGACGCCGATCACACTAAGAA
ACTGAGCATTTCGACGAACGTGTCCTGCGTGGTTCAGTACATAACCGAACCTGCAGAAACAAGTGGAGAATATGGAG
AAGAAAAAAAAGAGCTGACGACGACGAGCACCACCAACTGTCAACCCAAGATGTGGGTAGAAGC

>SEQ ID NO: 84
MEYPWLQSQVHSFSPTLHFPSFLHPLDDSKSHNINLHHMSLSHSNNTNSNNNNYQEEDRGAVVLEKKLNHNASERDR
RRKLNALYSSLRALLPLSDQKRKLSIPMTVARVVKYIPEQKQELQRLSRRKEELLKRISRKTHQEQLRNKAMMDSID
SSSSQRIAANWLTDTEIAVQIATSKWTSVSDMLLRLEENGLNVISVSSSVSSTARIFYTLHLQMRGDCKVRLEELIN
GMLLGLRQS

>SEQ ID NO: 85
MCALTPMFPSNQQEWYSTSTMEYPWLDSFSPTLPSSLYPSFDQLDEFKSYNINLLPHHMNLADINGTNNDQEEHQGS
VLEKKLNHNASERDRRRKLNALYASLRALLPPSDQKRKLSIPKTIAGVVKYIPEQKQELQRLSRRKEELMKRISNKT
ETLNHQQEQLRNRALMMESIDSSSQKIA

>SEQ ID NO: 86
MEYPWLDSFSPTLPSSLYPSFDQLDEFKNYNINLLPHHMNLADINGTNNTSNNDQEEHQGSVLEKKLNHNASERDRR
RKLNALYASLRALLPPSDQKSANQRKLSIPKTVAGVVKYIPEQKQELQRLYRRKEELMKRISNKIETLNHQQEQLRN
RALMMESIDSSSQKIAANWITNTEIAVQIATWKWTSISDMLLRLEENGLNVISVSSSVSSTARIFYTLHLQM

>SEQ ID NO: 87
AFSFSSIDPQLNELYSSLRALLPDADHTKKLSIPTTVSRVLKYIPELQKQVENLERKKKELTTTSTTNCKPGVLGSQ
LMSEGMAPIV

>SEQ ID NO: 88
MEQLFVDDPAFASSMSSLEADIFSGAGQLPSSPWLDLDLDDDVQDLSMAPTTANAVSSGYGFGGSGSHRKLSHNAYE
RDRRKQLNELYSSLRALLPDADHTKKLSISTNVSCVVQYITEPAETSGEYGEEKKELTTTSTTNCQPQDVGRS

>SEQ ID NO: 89
ATGTGTGCACTTGTCCCTCCATTATATCCCAATTTCGGCTGGCCTTGCGGAGATCATAGCTTCTATGAAACCGACGA
CGTATCCAACACGTTTCTTGATTTTCCGTTGCCGGACTTGACGGTGACTCATGAGAATGTGTCGTCTGAGAATAACA
GAACATTACTAGACAATCCCGTGGTGATGAAGAAGCTTAATCACAACGCGAGTGAACGTGAGCGTCGCAAGAAGATC
AACACAATGTTCTCATCTCTTCGTTCTTGTCTTCCTCCCACCAATCAAACGAAGTTAAGTGTTTCGGCAACAGTTTC
ACAAGCATTGAAGTACATACCAGAGCTGCAAGAGCAAGTTAAAAAGCTCATGAAGAAGAAAGAAGAGCTCTCGTTTC
AAATTTCGGGTCAAAGAGATCTCGTTTACACCGACCAAAACAGTAAGTCAGAGGAAGGGGTTACAAGCTATGCGTCG
ACAGTTTCTTCGACTAGGCTCAGTGAGACTGAAGTGATGGTCCAAATTTCATCGTTACAGACTGAAAAATGTTCGTT
TGGGAATGTCTTGAGTGGTGTAGAAGAAGATGGGTTGGTTCTTGTGGGTGCTTCATCTTCAAGGTCTCATGGAGAGC
GACTCTTTTACTCTATGCATCTTCAGATAAAAAATGGCCAGGTGAATTCCGAAGAATTAGGTGATAGATTGTTGTAC
TTGTACGAGAAATGTGGACACTCGTTTACATGA

>SEQ ID NO: 90
ATGTGTGCACTTGTCCCTCCATTATATCCCAATTTCGGCTGGCCTTGCGGAGATCATAGCTTCTATGAAACCGACGA
CGTATCCAACACGTTTCTTGATTTTCCGTTGCCGGACTTGACGGTGACTCATGAGAATGTGTCGTCTGAGAATAACA
GAACATTACTAGACAATCCCGTGGTGATGAAGAAGCTTAATCACAACGCGAGTGAACGTGAGCGTCGCAAGAAGATC
AACACAATGTTCTCATCTCTTCGTTCTTGTCTTCCTCCCACCAATCAAACGAAGAAGTTAAGTGTTTCGGCAACAGT
TTCACAAGCATTGAAGTACATACCAGAGCTGCAAGAGCAAGTTAAAAAGCTCATGAAGAAGAAAGAAGAGCTCTCGT
TTCAAATTTCGGGTCAAAGAGATCTCGTTTACACCGACCAAAACAGTAAGTCAGAGGAAGGGGTTACAAGCTATGCG
TCGACAGTTTCTTCGACTAGGCTCAGTGAGACTGAAGTGATGGTCCAAATTTCATCGTTACAGACTGAAAAATGTTC
GTTTGGGAATGTCTTGAGTGGTGTAGAAGAAGATGGGTTGGTTCTTGTGGGTGCTTCATCTTCAAGGTCTCATGGAG

AGCGACTCTTTTACTCTATGCATCTTCAGATAAAAAATGGCCAGGTGAATTCCGAAGAATTAGGTGATAGATTGTTG
TACTTGTACGAGAAATGTGGACACTCGTTTACATGA

>SEQ ID NO: 91
CCACGTCGTCTGCGCGGCCGACTCCTTCTACGTCGGCCTCCCGATCCCGGTGGTGTCCGCCGGCGAGGAGCTGATGG
CGGGGCGAACCTCATCCACAACGCCTACGAGCGCGACCGCCGGAAGCAGCGCAACGAGCTCTACTCCTCCCTCCGCG
CTCTCCTCCCCGACGCCGATCACACTAAGAAGCTGAGCATCCCGACGACGGTGTCTCGCGTGCTCAAGTACATACCC
GAGCTGCAGAAGCAGGTGGAGAATCTGGAGAGGAAGAAGAAGGAGCTGACGACGACGAGCACCACCAACTGCAAACC
AGGAGTGTTGGGGAGCCAGCTGATGAGCGAGGGCATGGCTCCCATCGTTTCGGCTACCTGCATCAATGACATGGAGA
TCATGGTTCAGGTCAGCTTGTTGAGCAATGTGGCGGGTTCAGTTCTTCCTCTCTCCAAGTGTATCAAAGTACTGGAG
AACGAAGGTCTTCACTTCATCAGTTCATCGACTTCCTCCGGATTTGGGAACAGGACATTCTACAGTATCCATCTTCA
GAGAAGTGAAGGAACGATCAACGAGGAGTGCCCAGCATTTTGTGAAAGGTTGGAGAAAGTCGTCAGGAACAAAGCAA
AGCTT

>SEQ ID NO: 92
ATGGAGCACCAGCTGTTCGATGACCCCTTCTCTAGCAGCATCTCGTCGCTGGAGGCGGACATCTTCTCCGCCGGCGG
CCAGCTGCCGTCGCCGCCGTGGCCGGACCTCGACCTCGACCTCGACGACGACGACGGCATCCACGACCTCTCCGCGC
CGGCCGGCAACCCCACCTCTTCAGGAGGCTATGGCTCGGGCGGAGGCTCCCACAGGAAGATCAGCCACAACGCGTAC
GAGCGTGACCGCCGGAAGCAGCTCAACGAGCTCTACTCCTCGCTCCGCTCCCTCCTCCCCGACGCTGACCACACTAA
GAAGCTGAGCATCCCCACCACGGTCTCCCGAGTTCTCAAGTACATCCCCGAGCTGCAGAAGCAGGTGGACAACCTGG
AGAGGAGGAAGAAGGAGCTGACGAACGCCAACTGCAAACCAGGAGTTCTGAACACGAGCCAGATTGTAACTCCCATT
GTTTCTGCTACTTGCCTCAACGATACGGAGATCATGGTTCAGGTCAGCCTGCACAGCAACGTGGCTGCCACAAGTCT
TCCTCTGTCCAAGTGCATAAAAGTGATGGAGAACGAAGGCCTTCACCTAATTAGTTCATCAACTTACTCCACCTTCG
ACAACAGGACATTCTATAGCCTCCATGTTCAGAGAAGTCAAAGAACGATGAAGGAGGAGTGCCCAGCATTCTGCGAT
GAACTGGAGAGGATTATC

>SEQ ID NO: 93
ATGGACCATCAGCTGTTCGACGACCCCTTCGGGAGCAGCATCTCGTCGCTGGAGGCGGACATCTTCTCCGCCGGCGG
CGGCGGACAGCTGCCGTCGCCGCCGTGGCCGGACCTCGACCTCGACGACGACTACGACATACACGACCTCTCCGCGC
CGGCCGCCAACGCCGCCACCTCCTCGGGCGGCGGCTATGGCTCCGCGGCTCCGGCAGGAAGCTCAGCCACAACGCA
TACGAGCGCGACCGCCGGAAGCAGCTCAACGAGCTCTACTCCTCGCTCCGATCCCTCCTCCCGGACGCTGATCACAC
TAAGAAGCTGAGCATCCCCACCACCGTGTCCCGAGTTCTCAAGTACATCCCGGAGCTGCAGAAGCAGGTGGATAACC
TGGAGAGGAGGAAGAAGGAGCTGACCAACGCCAACTGCAAGCGGGAGTTCTCAACACCAAAGAGATCGTAACTCCC
ATTGTTTCTGCTACTTGCCTTAACGACACGGAGATCATGGTTCAGGTCAGCCTGCACAGCAATGTGGCCGCCACAGC
TCTCCCTCTCTCCAAGTGCATAAAGGTGCTAGAAAACGAAGGCCTTCTCCTCGTCAGCTCATCAACCTACTCCACCT
TCGAGAACAAGACATTCTATAGCCTCCATCTTCAGAGAAGTCAAAGAACGATGAAGGAGCAGTGCCCAGGATTCTGC
GACGAACTGGAGAAGATCGTCAGGAAGAAAGCAGGGGCG

>SEQ ID NO: 94
GCCTCGTGCCGGCGGGTGCTCAAGTACATCCCCGGAGCTGCAGAAGCAGGTGGACGGACTGGAGAAGAAGAAGGAGGA
GCTGACGCGCGCCAACTGCAAGCCCGGCGTGCTGACCATGAAGGAGAACATGGCTCCGATCGTGTCCGCCACCTGCC
TCGATGACAGAGAAATCATGGTCCAGGTCAGCCTGGTGAGCACCATGGCCGGAGTTCTGCCCATGTCCAAGTGCATC
AAGGTGCTGGAGAACGAAGGCCTACGCCTCATCAGCTCGTCCACTTCCGCGTTTCACAACAGGACGTTCTATAGCCT
CCATCTTCAGAGAACCCAACGACGATGAGCAAGGAGTGTCCGGCATTTTGTGAAGAACTGGAGAACGCCCTGACGC
AAAAGGCAGGACTACGTCTACATCACCACCAG

>SEQ ID NO: 95
ATGGATCACCAGCTGTACGGCGACCCCTCCGCGAGCAGCTTCTCTCCGCTGGAGGCACAGATCTTCTCCGGCCAGCT
GCCGCCGTCGTCAACGCCATGGCCAAATCTCGACGTTGACCTCGCCCTGGACCTCGACGTTCTCGAGGATGACATCG
TCCGGGAGCTCTCTGCTGGCACAGTGGCAAACGCGGCATCGTCAGGTTCCGGCTCCGGCGCCCACAAGAAGCTCAGC
CACAACGCGTACGAGCGCGACCGCCGGAAGCAGCTCAACGAGCTATACCTCTCGCTCCGTTCTCTCCTCCCGGACGC
CGACCACACCAAGAAGCTGAGTATTCCGACGACGGTGTGTCGAGCGCTCAAGTACATCCCCGAGCTGCAGAAACAGG
TCGAGAATCTGGAGAAGAAGAAGAGAAACTGGCTAGTGCCAACTGCAAACCAGGGGTACTGAGCGTGACCGGCAGC
ATAGCTCCAACTGTGTCCGCTACTTGCCTCAACCACAAGGAAATCATGGTTCAGATTAGCTTGCTGAGAGATACAGA
TGCTTCTACAGCTCTACCTCTTTCCAAGTGTATAAATGTACTGGAGAACGAAGGACTTCAGCTCATCAGTTCATCGA
CTTCCTCCACCTTTGGGAACAAAACGTTCTATAACCTCCATCTTCAGAGAAGTCAAGGAGCCACTAAACATGGAGTG
CCCATCGTTTTG

>SEQ ID NO: 96
CGCAGATCTTCTCCAGCCAGCTGCCGCCGTCACCGCCGTGGCCGAATCTCGATGTTGACGTTGACCTGGACCTCGAC
GTTCTTGAGGACGACGTCGTCGGCGAACTCTCAGGGAGGCCGGCAACGCGCATCGTCAGGCTCTCAGGCTCCGGCGG
CCCCGGCTCCCACAAGAAGCTCAGTCACAACGCGTACGAGCGCGACCGCCGGAAGCAGCTCAACGAGCTCTACCTCT
CACTCCGTTCTCTCCTGCCGGACGCCGACCACACTAAGAAGCTGAGTATTCCGACGATGGTGTGTCGAGCGCTCAAG
TACATCCCGAGCTGCAGAAACAGGTCGAGAATCTGGAGAAGAAGAAAGAGAAACTTGCTAGTTCCAACTGCAAACCA
GAGGTACTGAGCGCAAGCGGCAGCATAGCTCTAACTGTGTCCGCTACTTGCCTCAACGACAAGGAAATCATGGTTCA
GATTAGCTTGCTGAGACATACGGATGCTGCTACAGCTCTACCTCTTTCCAAGTGTATAAATGTACTGGAGAACGAAG
GACTTGAGCTCGTCAGTTCATCGACTTCCTGCACCTTTGGGAACAAAATGTTCTATAACCTCCATCTTCAGAGAAGT
CAAGGAGCGCTAACATGGGAGTGTCCATCCTTCTGTGACAAATTGGAACAAGCAATCAGGAAAACAGCAGGATTA

>SEQ ID NO: 97
CGACGGAAGCAGCTCAACGACCTTTACTCCTCGCTCCGCTCCCTCCTCCCGGACGCTGACCACACCAAGAAGCTGAG
CATCCCCACCACCGTGTCCCGAGTCCTCAAGTACATCCCGGAGCTGCAGAAGCAGGTGGACAACCTGGAGAGGAGGA
AGCGGGAGCTGACCAACGCCAACTGCAAGCCGGGAGTTCTCAACACCAGCGAGATCGTAACTACTCCCATTGTTTCT
GCTACTTGCCTCAACGACACGGAGATCATGGTTCAGGTCAGCCTGCACAGCAATGTGGCAGCCACGGCTCTCCCTCT
CTCCAAGTGCATAAAGGTGCTGGAGGACGCAGGCCTTCACCTCATCAGCTCATCAACCTACTCCACCTTTGGGAACA
AGACATTCTATAGCCTCCATCTTCAGGTGTGCATGCATGTTCATTCAATGGTTCCTGCCGTTTCCTTCAATTTTTTT
ATC

```
                              Sequences

>SEQ ID NO: 98
MCALVPPLYPNFGWPCGDHSFYETDDVSNTFLDFPLPDLTVTHENVSSENNRTLLDNPVVMKKLNHNASERERRKKI
NTMFSSLRSCLPPTNQTKLSVSATVSQALKYIPELQEQVKKLMKKKEELSFQISGQRDLVYTDQNSKSEEGVTSYAS
TVSSTRLSETEVMVQISSLQTEKCSFGNVLSGVEEDGLVLVGASSSRSHGERLFYSMHLQIKNGQVNSEELGDRLLY
LYEKCGHSFT

>SEQ ID NO: 99
MCALVPPLYPNFGWPCGDHSFYETDDVSNTFLDFPLPDLTVTHENVSSENNRTLLDNPVVMKKLNHNASERERRKKI
NTMFSSLRSCLPPTNQTKKLSVSATVSQALKYIPELQEQVKKLMKKKEELSPQISGQRDLVYTDQNSKSEEGVTSYA
STVSSTRLSETEVMVQISSLQTEKCSFGNVLSGVEEDGLVLVGASSSRSHGERLFYSMHLQIKNGQVNSEELGDRLL
YLYEKCGHSFT

>SEQ ID NO: 100
PRRLRGRLLLRRPPDPGGVRRRGADGGANLIHNAYERDRRKQRNELYSSLRALLPDADHTKKLSIPTTVSRVLKYIP
ELQKQVENLERKKKELTTTSTTNCKPGVLGSQLMSEGMAPIVSATCINDMEIMVQVSLLSNVAGSVLPLSKCIKVLE
NEGLHFISSSTSSGFGNRTFYSIHLQRSEGTINEECPAFCERLEKVVRNKAKL

>SEQ ID NO: 101
MEHQLFDDPFSSSISSLEADIFSAGGQLPSPPWPDLDLDLDDDDGIHDLSAPAGNPTSSGGYGSGGGSHRKISHNAY
ERDRRKQLNELYSSLRSLLPDADHTKKLSIPTTVSRVLKYIPELQKQVDNLERRKKELTNANCKPGVLNTSQIVTPI
VSATCLNDTEIMVQVSLHSNVAATSLPLSKCIKVMENEGLHLISSSTYSTFDNRTFYSLHVQRSQRTMKEECPAFCD
ELERII

>SEQ ID NO: 102
MDHQLFDDPFGSSISSLEADIFSAGGGGQLPSPPWPDLDLDDDYDIHDLSAPAANAATSSGGGYGSGGSGRKLSHNA
YERDRRKQLNELYSSLRSLLPDADHTKKLSIPTTVSRVLKYIPELQKQVDNLERRKKELTNANCKPGVLNTKEIVTP
IVSATCLNDTEIMVQVSLHSNVAATALPLSKCIKVLENEGLLLVSSSTYSTFENKTFYSLHLQRSQRTMKEQCPGFC
DELEKIVRKKAGA

>SEQ ID NO: 103
ASCRRVLKYIPELQKQVDGLEKKKEELTRANCKPGVLTMKENMAPIVSATCLDDREIMVQVSLVSTMAGVLPMSKCI
KVLENEGLRLISSSTSAFHNRTFYSLHLQRTQRTMSKECPAFCEELENALTQKAGLRLHHHQ

>SEQ ID NO: 104
MDHQLYGDPSASSFSPLEAQIFSGQLPPSSTPWPNLDVDLALDLDVLEDDIVRELSAGTVANAASSGSGSGAHKKLS
HNAYERDRRKQLNELYLSLRSLLPDADHTKKLSIPTTVCRALKYIPELQKQVENLEKKKEKLASANCKPGVLSVTGS
IAPTVSATCLNHKEIMVQISLLRDTDASTALPLSKCINVLENEGLQLISSSTSSTFGNKTFYNLHLQRSQGATKHGV
PIVL

>SEQ ID NO: 105
RRKQLNDLYSSLRSLLPDADHTKKLSIPTTVSRVLKYIPELQKQVDNLERRKRELTNANCKPGVLNTSEIVTTPIVS
ATCLNDTEIMVQVSLHSNVAATALPLSKCIKVLEDAGLHLISSSTYSTFGNKTFYSLHLQVCMHVHSMVPAVSFNFF
I
```

LITERATURE

1. Bailey, P. C., Martin C., Toledo-Ortiz, G., Quail, P. H., Huq, E., Heim, M. A., Jakoby, M., Weber, M., Weisshaar, B. (2003). Update on the Basic Helix-Loop-Helix Transcription Factor Gene Family in *Arabidopsis thaliana*. Plant Cell 15(11), 2497-2502.
2. Brownlie, P., Ceska, T. A., Lamers, M., Romier, C., Stier, G., Teo, H., Suck, D. (1997). The crystal structure of an intact human Max-DNA complex: new insights into mechanisms of transcriptional control. Structure 5, 509-520.
3. Heim, M. A., Jakoby, M., Werber, M., Martin, C., Weisshaar, B., and Bailey, P. C. (2003). The basic helix-loop-helix transcription factor family in plants: A genome-wide study of protein structure and functional diversity. Mol. Biol. Evol. 20, 735-747.
4. Kang, H.-G., Foley, R. C., Onate-Sanchez, L., Lin, C., Singh, K. B. (2003). Target genes for OBP3, a D of transcription factor, include novel basic helix-loop-helix domain proteins inducible by salicylic acid. Plant J 35, 362-372.
5. Ling H. Q., Bauer P., Bereczky Z., Keller B., Ganal M. (2002). The tomato fer gene encoding a bHLH protein controls iron-uptake responses in roots. Proc. Natl. Acad. Sci. USA 2002; 99:13938-13943
6. Martinez-Garcia, J. F., Huq, E., Quail, P. H. (2000). Direct Targeting of Light Signals to a Promoter Element-Bound Transcription Factor. Science 288, 859-863.
7. Ogo, Y., Itai, R. N., Nakanishi, H., Inoue, H., Kobayashi, T., Suzuki, M., Takhashi, M., Mori, S., Nishizawa, N. K. Isolation and characterization of IRO2, a novel iron-regulated bHLH transcription factor in graminaceous plants. J. Exp. Bot. 57, 2867-2878.
8. Ramsay, N. A., Walker, A. R., Mooney, M., Gray, J. C. (2003). Two basic-helix-loop-helix genes (MYC-146 and GL3) from *Arabidopsis* can activate anthocyanin biosynthesis in a white-flowered *Matthiola incana* mutant. Plant Mol. Biol. 52, 679-687.
9. Toledo-Ortiz, G., Huq, E., and Quail, P. H. (2003). The *Arabidopsis* basic/helix-loop-helix transcription factor family. Plant Cell 15(8), 1749-1770.
10. Tominaga, R., Iwata, M., Okada, K., Wada, T. (2007). Functional Analysis of the Epidermal-Specific MYB Genes CAPRICE and WEREWOLF in *Arabidopsis*. Plant Cell 19(7), 264-2277.
11. Vorwieger, A., Gryczka, C., Czihal, A., Douchkov, D., Tiedemann, J., Mock, H.-P., Jakoby, M., Weisshaar, B., Saalback, I., Baumlein, H. (2007). Iron assimilation and transcription factor controlled synthesis of riboflavin in plants. Planta 226, 147-158.

12. Wang H.-Y., Klatte, M., Jakoby, M., Baumlein, H., Weisshaar, B., Bauer, P. (2007) Iron deficiency-mediated stress regulation of four subgroup Ib BHLH genes in *Arabidopsis thaliana*. Planta 226, 897-908.
13. Yuan, Y., Wu, H., Wang, N., Li, J., Zhao, W., Du, J., Wang, D, Ling, H.-Q. (2008). FIT interacts with AtbHLH38 and AtbHLH39 in regulating iron uptake gene expression for iron homeostatis in *Arabidopsis*.
14. Zhang, F., Gonzalez, A., Zhao, M., Payne, T., Lloyd, A. (2003) A network of redundant bHLH proteins functions in all TTG1-dependent pathways of *Arabidopsis*. Development 130, 4859-4869.

We claim:

1. A method of producing a heat stress tolerant plant, comprising
   a) transforming a plant, a plant tissue culture, or a plant cell with a vector comprising a nucleic acid construct that comprises a nucleic acid sequence encoding a bHLH subgroup 1b polypeptide to obtain a transformed plant, a transformed plant tissue culture, or a transformed plant cell, wherein said bHLH subgroup 1b polypeptide is bHLH39,
   b) growing said transformed plant or regenerating a plant from said transformed plant tissue culture or transformed plant cell, and
   c) selecting a plant having increased heat stress tolerance relative to a wild type control from said transformed plant or regenerated plant from b) under a heat stress condition.

2. The method of claim 1, wherein said nucleic acid construct comprises a constitutive promoter, an inducible promoter or a tissue specific promoter.

3. The method of claim 2, wherein said tissue specific promoter is a root promoter.

4. The method of claim 1, wherein said nucleic acid construct comprises a nucleic acid sequence selected from SEQ ID NOs: 1-17.

5. The method of claim 4, wherein said nucleic acid construct comprises a nucleic acid sequence having SEQ ID NO: 2.

6. The method of claim 4, wherein said nucleic acid construct comprises a nucleic acid sequence having SEQ ID NO: 5, 6, or 7.

7. The method of claim 4, wherein said nucleic acid construct comprises a nucleic acid sequence having SEQ ID NO: 8.

8. The method of claim 4, wherein said nucleic acid construct comprises a nucleic acid sequence having SEQ ID NO: 9.

9. The method of claim 4, wherein said nucleic acid construct comprises a nucleic acid sequence having SEQ ID NO: 10.

10. The method of claim 4, wherein said nucleic acid construct comprises a nucleic acid sequence having SEQ ID NO: 12.

11. The method of claim 4, wherein said nucleic acid construct comprises a nucleic acid sequence having SEQ ID NO: 13, 14, 15, or 16.

12. The method of claim 4, wherein said nucleic acid construct comprises a nucleic acid sequence having SEQ ID NO: 17.

* * * * *

SEQUENCE LISTING

```
<160> NUMBER OF SEQ ID NOS: 125

<210> SEQ ID NO 1
<211> LENGTH: 777
<212> TYPE: DNA
<213> ORGANISM: Arabidopsis thaliana

<400> SEQUENCE: 1
atgtgtgcat tagtacctcc attgtttcca aactttgggt ggccatcaac gggagagtac      60
gacagctact acctcgccgg agatatcctc aacaacggcg ggtttcttga ttttccggta     120
ccggaggaga cttatggagc tgttacagcg gtgactcaac atcagaatag ctttggtgtt     180
tctgtttcgt cggagggaaa tgaaatagac aacaatccgg tggtcgtcaa gaagcttaat     240
cacaatgcta gtgagcgtga ccgtcgcagg aaaattaact ctttgttctc atctctccgt     300
tcatgtcttc ctgcctctgg ccaatcgaag aagctaagca ttcctgcgac ggtttctcga     360
agcttgaagt acataccaga gctgcaagag caagtgaaga agctaataaa aagaaggaa     420 gagctcttgg tgcaaatttc aggtcaaaga aacactgaat gttacgttaa gcagccacca     480
aaggccgtcg cgaattatat ctcgaccgtt tctgcgacta ggcttggtga caacgaagtg     540
atggtccaaa tctcatcgtc caagattcat aactttcga tatctaatgt tttaagtggg     600
ttagaagaag ataggtttgt tcttgtggac atgtcatctt caaggtctca aggagaaagg     660
cttttctaca ctttgcattt acaagtggag aagattgaaa attacaagct gaattgcgaa     720
gagttaagtc agaggatgtt gtacttgtat gaggaatgtg gaaactcata tatatga     777

<210> SEQ ID NO 2
<211> LENGTH: 222
<212> TYPE: DNA
<213> ORGANISM: Avena sativa

<400> SEQUENCE: 2
gcacgaggcc tccctccgct ccctcctccc cgacaccgat cacagcaaga agctgagcat      60
ccccatcact gtgacgcggg tgctcaagta catcccggag ctgcagaagc aggtggacac     120
gctggagaag aagaaggaag agctgaccca ggcgaactgc aaaccaggag ttgtggccat     180
gaaggagaac acggctccga tcgtgtccgc cacctgcctc ga                       222

<210> SEQ ID NO 3
<211> LENGTH: 2091
<212> TYPE: DNA
<213> ORGANISM: Brachypodium distachyon

<400> SEQUENCE: 3
atggggcaca agcagctgtt cgtggacgac ccgttcgcga gcagcatctc gtctctggag      60
gcggaggcca tcttctccgg cgccggcggg cagtggcgcg ccggcggcgg cctcgacgac     120
cgtgacctct ccgccatgcc ggcggcggcc aacacctcgt cgggcggctc cggctctccc     180
ggcggcggcg gcaggaagat gagccacaac gcgtacgagc gcgaccgccg caagcagctc     240
aacgagctct actcctcccc tcgctccctc tccccgacg ccgaccacac cgtatgcaaa      300
tcaaattgaa gccatagatc ataatttgat cctgaatcct gatggatctg gtgatgattt     360
```

| | |
|---|---|
| gactaattgc agaagaagct gagcatcccg atcacagtgt cgcgggtgct aaagtacatc | 420 |
| ccggagctgc agaaggaagt ggacgggctg gagaggaaga aggaggagct gacgcgcgcc | 480 |
| aactgcaagc ccggggtgat cgccatgaag gaccagaacg ttgctcccgt cgtctccgcg | 540 |
| acctgcctcg acgacaagga catcatggtt caggtcagct tgctcagcgg catggcggcg | 600 |
| gcggctctgc cgatgtccac gtgcataaag attctggaga acgaaggtct tcgcctcgtc | 660 |
| agctcgtcca cttctgcctt tgggaacagg acgttctata acctccatct tcaggtaatt | 720 |
| ggtacatctg tctgcatgaa gccttaattt cctattggta attatcaatg tcatcgatcc | 780 |
| atgcttgctc gattcatttt ggcaaatttg cctcatactt actcgacatc gtagtagaag | 840 |
| agaaggaaaa aaaaaagccc agcatttttc tttgagaaac aaagcacaac attttctgct | 900 |
| cccaagatcc attccgaaag ccgggtgcac aacactacga gtaaaaatcg tttcctctta | 960 |
| gttatataac gtgtggtacc ttcaacttaa atgagcatca gttgatgcag agtggtaccc | 1020 |
| ctgttcggaa aagacttcaa catggcacca tcttcactag aggtccccca gcccctaatt | 1080 |
| cagacgaagg catcattta gtccattaac cccggtaggt tgagattaca aaggctagat | 1140 |
| ttatataacg gttttgctat ttctaaggcg actgagaaat aagtatttct aacaaccatt | 1200 |
| tgatccaatc actgagattc gtgcaagatc catacatata caaagtatta gaaaacctta | 1260 |
| atcggatgga tatgatcgtt gactgagaaa tagacacttc ttttatgtaa agggtgttta | 1320 |
| ctatatatat gtgggttttg atatactcat attgaataga tttgaagatc atgtcaggcc | 1380 |
| ctacttaggg taatctgttg tgaaattaaa ctgtgttcat agggcaaaaa cattgtctta | 1440 |
| taaatcagca caaaatcaac gaattgggag tttttacgta acaaatataa attgtagcaa | 1500 |
| cacaaattaa ttggctacaa tacaatccaa gaacaacaag acgagtatac acggcaaacg | 1560 |
| atcatgcata tggtgagttg gtgaccagat cacccgctct actagatgct cctagatgca | 1620 |
| tatggtgcca taattttagg aaaaccgaac tggaagaagc acctaaaaaa cgagtatgaa | 1680 |
| atcatcaatc gaccaagatt agaggtcggt ctcatcatcg acaacatgaa caattaagat | 1740 |
| gcatgctgga gaacagataa tctaacacag ccacaggttt attacaaaaa gcttaacaga | 1800 |
| aacttcgcta aagcaaccaa agaatgagaa caaaaaaata tatcttctaa taacatgtgt | 1860 |
| gtgctgttgt atagcatctg aaggcgtaat gcgaaactct aatttatctg aagtatgtag | 1920 |
| tgcttatatg cttatataac atgtaaataa gcaatatata ttcattaatt tcatttaatt | 1980 |
| tgtatactga aacagagaaa ccagcgaacg atgagcaagg agtgcccagc gttctgtgac | 2040 |
| gagctggaga aagccatcaa gaaaaggca ggactgcata tgcatcagtg a | 2091 |

<210> SEQ ID NO 4
<211> LENGTH: 729
<212> TYPE: DNA
<213> ORGANISM: Brachypodium distachyon

<400> SEQUENCE: 4

| | |
|---|---|
| atggggcaca agcagctgtt cgtggacgac ccgttcgcga gcagcatctc gtctctggag | 60 |
| gcggaggcca tcttctccgg cgccggcggg cagtggcgcg ccggcggcgg cctcgacgac | 120 |
| cgtgacctct ccgccatgcc ggcggcggcc aacacctcgt cggcggctc cggctctccc | 180 |
| ggcggcggcg gcaggaagat gagccacaac gcgtacgagc gcgaccgccg caagcagctc | 240 |
| aacgagctct actcctcccct ccgctcccctc ctccccgacg ccgaccacac caagaagctg | 300 |
| agcatcccga tcacagtgtc gcgggtgcta aagtacatcc ggagctgca gaaggaagtg | 360 |
| gacgggctgg agaggaagaa ggaggagctg acgcgcgcca actgcaagcc cggggtgatc | 420 |

```
gccatgaagg accagaacgt tgctcccgtc gtctccgcga cctgcctcga cgacaaggac    480
atcatggttc aggtcagctt gctcagcggc atggcggcgg cggctctgcc gatgtccacg    540
tgcataaaga ttctggagaa cgaaggtctt cgcctcgtca gctcgtccac ttctgccttt    600
gggaacagga cgttctataa cctccatctt cagagaaacc agcgaacgat gagcaaggag    660
tgcccagcgt tctgtgacga gctggagaaa gccatcaaga aaaaggcagg actgcatatg    720
catcagtga                                                           729

<210> SEQ ID NO 5
<211> LENGTH: 587
<212> TYPE: DNA
<213> ORGANISM: Brassica napus

<400> SEQUENCE: 5
aaaaaaaaat tagaaaagaa gaaaagagtt tatcgggtct ctctcacgag tcacggcgtc     60
gacgaaactg gaggtgaagc catctccgat cgagagtcgc cgtcatccct atcccactcc    120
tgcaatatct actccgacgc tgtcgtcgtt aatttcggca cctcctcgcc aagtcgccat    180
cgtccctgtc gtgtgcgagc tgtcactgtc catgcaacga ataaatactc tgtgtctgca    240
tcgctttgac agtgcttggt gcttctatga tatgtcctcc ggtttatgct ttgcccagat    300
tcggaagaag atgggtttgt tcttgttgat gtttcatctt ctaggtctca tggagaaagg    360
ctcgtctaca gtttgcatct tcaaatggga acataaaata atcacgagct gacgtgcgaa    420
gagctaagcc agagaatgta tacttgtatg aggaatgcgg aaactcgttt agatgataat    480
ctgttcttgt ttcttttagt tatgtcatct gtttctcaac atgtaacatt catgtagccg    540
agttgtttcg tttatttttc ttgtcgaaat caatgatcga ttatcgc                 587

<210> SEQ ID NO 6
<211> LENGTH: 595
<212> TYPE: DNA
<213> ORGANISM: Brassica napus

<400> SEQUENCE: 6
gacggcgtcg acgaaactgg aggtgaagcc atctccgatc gagagtcgcc gtcatcccta     60
tcccactcct gcaatatcta ctccgacgct gtcgtcgtta atttcggcac ctcctcgcca    120
agtcgccatc gtccctgtcg tgtaagccct aggtctgatt tgtctttcct tttaaatcga    180
cgaaattgaa attgtgcgag ctgtcactgt ccatgcaacg aataaatact ctgtgtctgc    240
atcgctttga cagtgcttgg tgcttctatg atatgtcctc cggtttatgc tttgcccaga    300
ttcggaagaa gatgggtttg ttcttgttga tgtttcatct tctaggtctc atggagaaag    360
gctcgtctac agtttgcatc ttcaaatggg aacataaaat aatcacgagc tgacgtgcga    420
agagctaagc cagagaatgt atacttgtat gaggaatgcg gaaactcgtt tagatgataa    480
tctgttcttg tttcttttag ttatgtcatc tgtttctcaa catgtaacat tcatgtagc     540 cgagttgttt cgtttatttt cttgtcgaaa ttcaatgatc gattatcaca tttac         595

<210> SEQ ID NO 7
<211> LENGTH: 631
<212> TYPE: DNA
<213> ORGANISM: Brassica napus

<400> SEQUENCE: 7
gacgacaaaa aaaaaaatta gaaaagaaga aaagagttta tcgggtctct ctcacgagtc     60
acggcgtcga cgaaactgga ggtgaagcca tctccgatcg agagtcgccg tcatccctat    120
```

```
cccactcctg caatatctac tccgacgctg tcgtcgttaa tttcggcacc tcctcgccaa    180
gtcgccatcg tccctgtcgt gtaagcccta ggtgcgagct gtcactgtcc atgcaacgaa    240
taaatactct gtgtctgcat cgctttgaca gtgcttggtg cttctatgat atgtcctccg    300
gtttatgctt tgcccagatt cggaagaaga tgggtttgtt cttgttgatg tttcatcttc    360
taggtctcat ggagaaaggc tcgtctacag tttgcatctt caaatgggaa acataaataa    420
tcacgagctg acgtgcgaag agctaagcca gagaatgtat acttgtatga ggaatgcgga    480
aactcgttta gatgataatc tgttcttgtt tcttttagtt atgtcatctg tttctcaaca    540
tgtaacattc atgtagccga gttgtttcgt ttattttctt gtcgaaatca atgatcgatt    600
atcacattta catgctactg aatattgact g                                    631
```

<210> SEQ ID NO 8
<211> LENGTH: 693
<212> TYPE: DNA
<213> ORGANISM: Brassica rapa

<400> SEQUENCE: 8

```
acgacaaaaa aaaattagaa aagaagaaaa gagtttatcg ggtctctctc acgagtcacg     60
gcgtcgacga aactggaggt gaagccatct ccgatcgaga gtcgccgtca tccctatccc    120
actcctgcaa tatctactct gacgctgtcg tcgttaattt cggcacctcc tcgccaagtc    180
gccatcgtcc ctgtcgtgta agccctaggt ctgatttgtc tttccttta aatcgacgaa    240 attgaaattg tgcgagctgt cactgtccat gcaacgaata atactctgt gtctgcatcg    300 cttttgacagt gcgtggtgct tctatgatat gtcctctggt ttatgctttg cccagattcg    360
gaagaagatg ggtttgttct tgttgatgt ttcatcttct aggtctcatg gagaaaggct    420
cgtctacagt ttgcatcttc aaatgggaaa cataaataat cacgagctga cgtgcgaaga    480
gctaagccag agaatgtata cctgtatgag gaatgcggaa actcgtttag atgataatct    540
gttcttgttt cttttgtta tgtcgtctgt ttctcaacat gtaacattca tgtagccgag    600
ttgtttcgtt tattttcttg tcgaaatcaa tgatcgatta tcacatttac atgctactga    660
atattgactg attactatga aattcactaa tat                                  693
```

<210> SEQ ID NO 9
<211> LENGTH: 723
<212> TYPE: DNA
<213> ORGANISM: Glycine max

<400> SEQUENCE: 9

```
atggttgctt tgttttcccc tccggtgttc tcaaccaagg gatggttctt agaagaagag     60
ccattaagct atgatgtgtc ttcagattac tcatttccct atcaattttt tgcaccacag    120
acacagattg aacttgaaat agaaaggtcc tctgcaccat cccctgaaga ccctgccatg    180
gtcaaaaagc ttagccacaa cgctagtgaa cgtgatcgcc gcaagaaggt taatgacttg    240
gtttcttcac ttcgttcact tcttcctggg ccagatcaaa cgaaaaaaat gagcattcca    300
gctacagttt cgcgagtttt aaaatacata cctgagttac aacatcaagt gcaagcacta    360
actaagaaaa agaggagct tctgtgcaga atttcaaaaa atctcaaagg agattcggtg    420
aacaaagaat ctcaaaggag aatttcccat cacaattctg attttgctgt tcaactagt    480 aggctcaacg attgtgaagc tgttgttcac atttcctctt atgaggctca caaggctcca    540
ctatccgaca tcttgcaatg tttagaaaat aatggccttt atttgctaaa tgcttcttcc    600
tctgaaactt ttggaggaag ggtcttctac aacttgcatt tccaggtgga aaaaactcat    660
```

```
agattagagt ccgaaattct aactgagaag cttttgtcaa tatatgagaa gcaaaggatt    720
ttc                                                                 723
```

<210> SEQ ID NO 10
<211> LENGTH: 738
<212> TYPE: DNA
<213> ORGANISM: Hordeum vulgare

<400> SEQUENCE: 10

```
atggggcacc agacccagat gttcgacgac ccgttcgcga gcagtatgtc gtccctggac     60
gcagacatct tctccgtcgc cggcggcctc cacccatcgc agtggccggg actcgaccac    120
gacgtctcgc tggcgccggc tgccaacaac ggcacctcct ccggcggcta cggctccccc    180
gggggcggcg atggctcggg ctcccaccgc aagatcagcc acaacgcgta cgagcgcgac    240
cgccgcaagc agctcaacga gctctactcc gacctccgct ccctcctccc cgactccgat    300
cacaccaaga gctgagcat tccgatcacg gtgtcgcggg tgctcaagta catcccggag    360
ctgcagaagc aggtggacgg actggagaag aagaaggagg agcttacgag ggccagctgc    420
aagccaggcg tattgaccat gaaggagaac acggtcccga tcgtgtccgc cacctgcctc    480
gacgaaaggg agatcatggt ccaggttagc ttggtgagca ccatggccgg agctctgccc    540
atgtccaagt gcatcaaagt gctggagaac gaaggcctcc gcctcatcag ctcgtccact    600
tctgctttcc agaacaggac gttctatagc ctccatcttc agagaaccca acggacgatg    660
agcaaagagt gtccggcatt ttgtgaagaa ctggagaatg ccctgacgca gaaggcggga    720
ctacgtctac atcaccag                                                 738
```

<210> SEQ ID NO 11
<211> LENGTH: 723
<212> TYPE: DNA
<213> ORGANISM: Panicum virgatum

<400> SEQUENCE: 11

```
atgaccccctt ctcgagcagc atctcgtcgc tggaggcgga catcttctcc gccggcggcc     60
agcggcgcgt cgccgccgtg gccggacctc gaactcgacc tcgacctcga cgacgacgac    120
atccacgacc tctccgcgcc ggcggccaac gccacctcct caggaggcta tggctcgggc    180
ggaggctccg gcggctccca caggaagctc agccacaacg cgtacgagcg cgaccgccgg    240
aagcagctca cgagctcta ctcctcgctc cgctccctcc tccccgacgc tgaccacact    300
aagaagctga gcatccccac cacggtctcc cgagttctca agtacatccc cgagctgcag    360
aagcaggtgg acaacctgga gaggaggaag aaggagctga cgaacgccaa ctgcaaacca    420
ggagttctga agacgagcca gattgtaact cccattgttt ctgctacctg cctcaacgat    480
acggagatca tggttcaggt cagcctgcag agcaatgtgg ctgccacaag tcttcctctg    540
tccaagtgca taaaagtgct ggagaacgaa ggccttcacc tgattagttc atcaacttac    600
tccaccttcg acaacaggac attctatagc ctccatcttc agagaagtca agaacgatg    660 aaggaggagt gcccagcatt ctgcgatgaa ctggagagga ttatcaagaa gaaagcaggg    720
gcg                                                                 723
```

<210> SEQ ID NO 12
<211> LENGTH: 351
<212> TYPE: DNA
<213> ORGANISM: Solanum lycopersicum

<400> SEQUENCE: 12

```
atgttagcca tttcttcttc ttctcctcct ttattttcta ctactactaa taattttggt    60
tggcttttgg aagatcttat aagccatgaa ttaacaaata gtggagaaac ttcaaattca   120
tctcaaaaaa gccttcaaca ttgtgattca aataaatttg atcaaattat tatcaacagt   180
ggtgatcagt atcaacctga tcagacggtt aagaagctta atcataacgc aagtgaacgt   240
gaccgtagaa agaaaatcaa cagcttatat tcttctcttc gttctttact acctccttct   300
gatcatacga aaaagctaag cattccatca acagtatcaa gaattctaaa g            351
```

<210> SEQ ID NO 13
<211> LENGTH: 714
<212> TYPE: DNA
<213> ORGANISM: Triticum aestivum

<400> SEQUENCE: 13

```
atggggcacc agcaccagat gttcaacgac cccttcgcga gcagcatgtc gtcactggag    60
gaagacatgt tctccggtgc cggaggctac caccacctca cgccgtccat gcagtggccg   120
ggcttggata cgacatacc gtcggcgccg gctgccaaca cgccacctc ctccggtggc    180
tctggatcac accgcaagat gagtcacaac gcgtacgaac gtgaccgccg caagcagctc   240
aacgagcaat attcctccct ccgctccctc ctccccgacg atgatcacac caagaagatg   300
agcattccga ccacggtgtc gcgggtgatc aactacatcc cggagctgca gaaggaggta   360
gaccgcctgg agaagaagaa ggaggagctg aggcggggca gctgcgagca aggcgccatg   420
aggcagaaca cggcccccgat cgtgtccgcc acctgcctcg acgacaggga gatcatggtc   480
caggtcagcc tggtgagcac catggcggga gctctgccca tgtccaagtg catcaaggtg   540
ctggagaacc aaggccttcg cctcataaat tcctcgactt ccgcgtttca gaacaggacg   600
ttctacagcc tccatcttca gagaacccaa cggacaatga gcaaggaggg ccaaacattt   660
tgtaacgaat tggagaacgc tgtgaagcaa aaggcgggac tacatctaca tcat          714
```

<210> SEQ ID NO 14
<211> LENGTH: 617
<212> TYPE: DNA
<213> ORGANISM: Triticum aestivum
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (504)..(505)
<223> OTHER INFORMATION: n is a, c, g, or t

<400> SEQUENCE: 14

```
atggggcacc agcaccagat gttcgaagac ccgttcgcga gcagcatatc gtcgctggag    60
gccgagatat tctccgtcgc cggcggccac caccatacgc agtggccggg cctcgaccac   120
gacatcccgc tggccccggc tgccaataac ggcacctcct ccggcggcta cggctccccc   180
ggggggcggcg atggctcggg ctcccatcgc aagatcagcc acaacgccta cgagcgcgac   240
cgccgcaagc agctcaacga gctctactcc gacctccgct ccctcctccc cgacaccgat   300
cacacgaaga agcttagcat tccgatcacg gtgtcgcggg tgctcaagta catcccggag   360
ctgcagaagc aggtggacgg cctggagaag aagaaggagg agctgacgcg cgccagctgc   420
aagcccggcg tgctgaccat gaaggggggac acggctccga tcgtgtccng ccactgcctc   480
gacgacaggg agatcatggt ccanngtcag ctggtgagca ccatgggcgg agtctgccat   540
```

```
gtcaagtgct caggtgctga gacgaaggct cggctcatag tcgtcactcc ggttcagaca      600
gactctatat tcatctc                                                    617
```

<210> SEQ ID NO 15
<211> LENGTH: 434
<212> TYPE: DNA
<213> ORGANISM: Triticum aestivum

<400> SEQUENCE: 15

```
atggggcacc agcaccagat gttcgaagac ccgttcgcga gcagcatatc gtcgctggag       60
gcggacatct tctccgtcgc cgccggccac caccatccgc agtggccggg cctcgaccac      120
gacgtcccgt tggcgccggc tgccaacaac ggcacatcct ccggcggcta cggctccccc      180
ggtggcggcg acggctcggg ctcccaccgc aagatcagcc acaacgcgta cgagcgcgac      240
cgccgcaagc agctcaacga gctctactcc gacctccgct ccctcctccc cgacaccgat      300
cacacgaaga aactgagcat tccgatcacg gtgtcgcggg tgctcaagta catcccggag      360
ctgcagaagc aggtggacgg actggagaag aagaaggagg agctgacgcg cgccaactgc      420
agcccggcgt gctg                                                       434
```

<210> SEQ ID NO 16
<211> LENGTH: 261
<212> TYPE: DNA
<213> ORGANISM: Triticum aestivum

<400> SEQUENCE: 16

```
aacaacgcca cctcctccgg cggctctgga tcacaccgaa agatgagtca caacgcgtac       60
gagcgtgacc gccgcaagca gctcaacgag caatattcct ccctccgctc cctcctcccc      120
gatgacgacc acaataagaa gatgagcatt ccgaccacgg tgtcgcgggt gatcaagtac      180
atcccggagc tgcagaagga ggtagacggc ctggagaaga agaaggagga gctgaggcgg      240
gccagctacg agcaagcgcc a                                               261
```

<210> SEQ ID NO 17
<211> LENGTH: 228
<212> TYPE: DNA
<213> ORGANISM: Zea mays

<400> SEQUENCE: 17

```
cgtgtcccga gttctcaagt acatcccgga gctgcagaag caggtggaca acctggagag       60
gaggaagaag gagctgacca acgccaactg caagccggga gttctgaaaa ccaccaaggc      120
cgtaactccc attgtttctg ctacctgcct caacgacacg gagatcatgg ttcaggtcag      180
cctgcacagc gatgtggccg ccacagctct ccctctctcc aagtgcat                  228
```

<210> SEQ ID NO 18
<211> LENGTH: 258
<212> TYPE: PRT
<213> ORGANISM: Arabidopsis thaliana

<400> SEQUENCE: 18

Met Cys Ala Leu Val Pro Pro Leu Phe Pro Asn Phe Gly Trp Pro Ser
1               5                   10                  15

Thr Gly Glu Tyr Asp Ser Tyr Tyr Leu Ala Gly Asp Ile Leu Asn Asn
            20                  25                  30

Gly Gly Phe Leu Asp Phe Pro Val Pro Glu Glu Thr Tyr Gly Ala Val
        35                  40                  45

Thr Ala Val Thr Gln His Gln Asn Ser Phe Gly Val Ser Val Ser Ser
    50                  55                  60

Glu Gly Asn Glu Ile Asp Asn Pro Val Val Lys Lys Leu Asn
65                  70                  75                  80

His Asn Ala Ser Glu Arg Asp Arg Arg Lys Ile Asn Ser Leu Phe
                85                  90                  95

Ser Ser Leu Arg Ser Cys Leu Pro Ala Ser Gly Gln Ser Lys Lys Leu
                100                 105                 110

Ser Ile Pro Ala Thr Val Ser Arg Ser Leu Lys Tyr Ile Pro Glu Leu
                115                 120                 125

Gln Glu Gln Val Lys Lys Leu Ile Lys Lys Glu Glu Leu Leu Val
    130                 135                 140

Gln Ile Ser Gly Gln Arg Asn Thr Glu Cys Tyr Val Lys Gln Pro Pro
145                 150                 155                 160

Lys Ala Val Ala Asn Tyr Ile Ser Thr Val Ser Ala Thr Arg Leu Gly
                165                 170                 175

Asp Asn Glu Val Met Val Gln Ile Ser Ser Ser Lys Ile His Asn Phe
                180                 185                 190

Ser Ile Ser Asn Val Leu Ser Gly Leu Glu Glu Asp Arg Phe Val Leu
                195                 200                 205

Val Asp Met Ser Ser Ser Arg Ser Gln Gly Glu Arg Leu Phe Tyr Thr
                210                 215                 220

Leu His Leu Gln Val Glu Lys Ile Glu Asn Tyr Lys Leu Asn Cys Glu
225                 230                 235                 240

Glu Leu Ser Gln Arg Met Leu Tyr Leu Tyr Glu Cys Gly Asn Ser
                245                 250                 255

Tyr Ile

<210> SEQ ID NO 19
<211> LENGTH: 158
<212> TYPE: PRT
<213> ORGANISM: Avena sativa

<400> SEQUENCE: 19

Arg His Glu Ala Ser Leu Arg Ser Leu Leu Pro Asp Thr Asp His Ser
1               5                   10                  15

Lys Lys Leu Ser Ile Pro Ile Thr Val Thr Arg Val Leu Lys Tyr Ile
                20                  25                  30

Pro Glu Leu Gln Lys Gln Val Asp Thr Leu Glu Lys Lys Lys Glu Glu
                35                  40                  45

Leu Thr Gln Ala Asn Cys Lys Pro Gly Val Val Ala Met Lys Glu Asn
    50                  55                  60

Thr Ala Pro Ile Val Ser Ala Thr Cys Leu Asp Asp Arg Asp Ile Met
65                  70                  75                  80

Val Gln Val Ser Leu Leu Ser Asn Met Ala Gly Ala Leu Pro Val Ser
                85                  90                  95

Lys Cys Ile Lys Val Leu Glu Asn Glu Gly Leu Arg Leu Val Ser Ser
                100                 105                 110

Ser Thr Ser Ala Phe Gln Asn Lys Thr Phe Tyr Ser Leu His Val Gln
                115                 120                 125

```
Arg Thr Gln Arg Thr Ile Ser Lys Val Cys Pro Ala Phe Cys Asp Glu
        130                 135                 140

Leu Glu Asn Ala Ile Lys Arg Ala Gly Met Arg Leu Gln Gln
145                 150                 155
```

<210> SEQ ID NO 20
<211> LENGTH: 242
<212> TYPE: PRT
<213> ORGANISM: Brachypodium distachyon

<400> SEQUENCE: 20

```
Met Gly His Lys Gln Leu Phe Val Asp Asp Pro Phe Ala Ser Ser Ile
1               5                   10                  15

Ser Ser Leu Glu Ala Glu Ala Ile Phe Ser Gly Ala Gly Gly Gln Trp
            20                  25                  30

Arg Ala Gly Gly Gly Leu Asp Asp Arg Asp Leu Ser Ala Met Pro Ala
        35                  40                  45

Ala Ala Asn Thr Ser Ser Gly Gly Ser Gly Ser Pro Gly Gly Gly Gly
    50                  55                  60

Arg Lys Met Ser His Asn Ala Tyr Glu Arg Asp Arg Arg Lys Gln Leu
65                  70                  75                  80

Asn Glu Leu Tyr Ser Ser Leu Arg Ser Leu Leu Pro Asp Ala Asp His
                85                  90                  95

Thr Lys Lys Leu Ser Ile Pro Ile Thr Val Ser Arg Val Leu Lys Tyr
            100                 105                 110

Ile Pro Glu Leu Gln Lys Glu Val Asp Gly Leu Glu Arg Lys Lys Glu
        115                 120                 125

Glu Leu Thr Arg Ala Asn Cys Lys Pro Gly Val Ile Ala Met Lys Asp
    130                 135                 140

Gln Asn Val Ala Pro Val Val Ser Ala Thr Cys Leu Asp Asp Lys Asp
145                 150                 155                 160

Ile Met Val Gln Val Ser Leu Leu Ser Gly Met Ala Ala Ala Ala Leu
                165                 170                 175

Pro Met Ser Thr Cys Ile Lys Ile Leu Glu Asn Glu Gly Leu Arg Leu
            180                 185                 190

Val Ser Ser Ser Thr Ser Ala Phe Gly Asn Arg Thr Phe Tyr Asn Leu
        195                 200                 205

His Leu Gln Arg Asn Gln Arg Thr Met Ser Lys Glu Cys Pro Ala Phe
    210                 215                 220

Cys Asp Glu Leu Glu Lys Ala Ile Lys Lys Lys Ala Gly Leu His Met
225                 230                 235                 240

His Gln
```

<210> SEQ ID NO 21
<211> LENGTH: 241
<212> TYPE: PRT
<213> ORGANISM: Glycine max

<400> SEQUENCE: 21

```
Met Val Ala Leu Phe Ser Pro Val Phe Ser Thr Lys Gly Trp Phe
1               5                   10                  15

Leu Glu Glu Glu Pro Leu Ser Tyr Asp Val Ser Ser Asp Tyr Ser Phe
            20                  25                  30

Pro Tyr Gln Phe Phe Ala Pro Gln Thr Gln Ile Glu Leu Glu Ile Glu
        35                  40                  45
```

```
Arg Ser Ser Ala Pro Ser Pro Glu Asp Pro Ala Met Val Lys Lys Leu
 50                  55                  60

Ser His Asn Ala Ser Glu Arg Asp Arg Lys Lys Val Asn Asp Leu
 65                  70                  75                  80

Val Ser Ser Leu Arg Ser Leu Leu Pro Gly Pro Asp Gln Thr Lys Lys
                 85                  90                  95

Met Ser Ile Pro Ala Thr Val Ser Arg Val Leu Lys Tyr Ile Pro Glu
             100                 105                 110

Leu Gln His Gln Val Gln Ala Leu Thr Lys Lys Lys Glu Glu Leu Leu
         115                 120                 125

Cys Arg Ile Ser Lys Asn Leu Lys Gly Asp Ser Val Asn Lys Glu Ser
130                 135                 140

Gln Arg Arg Ile Ser His His Asn Ser Asp Phe Ala Val Ser Thr Ser
145                 150                 155                 160

Arg Leu Asn Asp Cys Glu Ala Val Val His Ile Ser Ser Tyr Glu Ala
                 165                 170                 175

His Lys Ala Pro Leu Ser Asp Ile Leu Gln Cys Leu Glu Asn Asn Gly
             180                 185                 190

Leu Tyr Leu Leu Asn Ala Ser Ser Glu Thr Phe Gly Gly Arg Val
         195                 200                 205

Phe Tyr Asn Leu His Phe Gln Val Glu Lys Thr His Arg Leu Glu Ser
210                 215                 220

Glu Ile Leu Thr Glu Lys Leu Leu Ser Ile Tyr Glu Lys Gln Arg Ile
225                 230                 235                 240

Phe

<210> SEQ ID NO 22
<211> LENGTH: 246
<212> TYPE: PRT
<213> ORGANISM: Hordeum vulgare

<400> SEQUENCE: 22

Met Gly His Gln Thr Gln Met Phe Asp Asp Pro Phe Ala Ser Ser Met
 1               5                  10                  15

Ser Ser Leu Asp Ala Asp Ile Phe Ser Val Ala Gly Leu His Pro
             20                  25                  30

Ser Gln Trp Pro Gly Leu Asp His Asp Val Ser Leu Ala Pro Ala Ala
         35                  40                  45

Asn Asn Gly Thr Ser Ser Gly Gly Tyr Gly Ser Pro Gly Gly Gly Asp
 50                  55                  60

Gly Ser Gly Ser His Arg Lys Ile Ser His Asn Ala Tyr Glu Arg Asp
 65                  70                  75                  80

Arg Arg Lys Gln Leu Asn Glu Leu Tyr Ser Asp Leu Arg Ser Leu Leu
                 85                  90                  95

Pro Asp Ser Asp His Thr Lys Lys Leu Ser Ile Pro Ile Thr Val Ser
             100                 105                 110

Arg Val Leu Lys Tyr Ile Pro Glu Leu Gln Lys Gln Val Asp Gly Leu
         115                 120                 125

Glu Lys Lys Lys Glu Glu Leu Thr Arg Ala Ser Cys Lys Pro Gly Val
130                 135                 140

Leu Thr Met Lys Glu Asn Thr Val Pro Ile Val Ser Ala Thr Cys Leu
145                 150                 155                 160

Asp Glu Arg Glu Ile Met Val Gln Val Ser Leu Val Ser Thr Met Ala
                 165                 170                 175
```

-continued

```
Gly Ala Leu Pro Met Ser Lys Cys Ile Lys Val Leu Glu Asn Glu Gly
            180                 185                 190

Leu Arg Leu Ile Ser Ser Thr Ser Ala Phe Gln Asn Arg Thr Phe
        195                 200                 205

Tyr Ser Leu His Leu Gln Arg Thr Gln Arg Thr Met Ser Lys Glu Cys
        210                 215                 220

Pro Ala Phe Cys Glu Glu Leu Glu Asn Ala Leu Thr Gln Lys Ala Gly
225                 230                 235                 240

Leu Arg Leu His His Gln
            245

<210> SEQ ID NO 23
<211> LENGTH: 241
<212> TYPE: PRT
<213> ORGANISM: Panicum virgatum

<400> SEQUENCE: 23

Met Thr Pro Ser Arg Ala Ala Ser Arg Arg Trp Arg Arg Thr Ser Ser
1               5                   10                  15

Pro Pro Ala Ala Ser Gly Ala Ser Pro Pro Trp Pro Asp Leu Glu Leu
            20                  25                  30

Asp Leu Asp Leu Asp Asp Asp Ile His Asp Leu Ser Ala Pro Ala
        35                  40                  45

Ala Asn Ala Thr Ser Ser Gly Gly Tyr Gly Ser Gly Gly Gly Ser Gly
    50                  55                  60

Gly Ser His Arg Lys Leu Ser His Asn Ala Tyr Glu Arg Asp Arg Arg
65                  70                  75                  80

Lys Gln Leu Asn Glu Leu Tyr Ser Ser Leu Arg Ser Leu Leu Pro Asp
                85                  90                  95

Ala Asp His Thr Lys Lys Leu Ser Ile Pro Thr Thr Val Ser Arg Val
            100                 105                 110

Leu Lys Tyr Ile Pro Glu Leu Gln Lys Gln Val Asp Asn Leu Glu Arg
        115                 120                 125

Arg Lys Lys Glu Leu Thr Asn Ala Asn Cys Lys Pro Gly Val Leu Lys
    130                 135                 140

Thr Ser Gln Ile Val Thr Pro Ile Val Ser Ala Thr Cys Leu Asn Asp
145                 150                 155                 160

Thr Glu Ile Met Val Gln Val Ser Leu Gln Ser Asn Val Ala Ala Thr
                165                 170                 175

Ser Leu Pro Leu Ser Lys Cys Ile Lys Val Leu Glu Asn Glu Gly Leu
            180                 185                 190

His Leu Ile Ser Ser Ser Thr Tyr Ser Thr Phe Asp Asn Arg Thr Phe
        195                 200                 205

Tyr Ser Leu His Leu Gln Arg Ser Gln Arg Thr Met Lys Glu Glu Cys
        210                 215                 220

Pro Ala Phe Cys Asp Glu Leu Glu Arg Ile Ile Lys Lys Lys Ala Gly
225                 230                 235                 240

Ala

<210> SEQ ID NO 24
<211> LENGTH: 117
<212> TYPE: PRT
<213> ORGANISM: Solanum lycopersicum
```

<400> SEQUENCE: 24

Met Leu Ala Ile Ser Ser Ser Pro Pro Leu Phe Ser Thr Thr Thr
1               5                   10                  15

Asn Asn Phe Gly Trp Leu Leu Glu Asp Leu Ile Ser His Glu Leu Thr
            20                  25                  30

Asn Ser Gly Glu Thr Ser Asn Ser Ser Gln Lys Ser Leu Gln His Cys
        35                  40                  45

Asp Ser Asn Lys Phe Asp Gln Ile Ile Ile Asn Ser Gly Asp Gln Tyr
    50                  55                  60

Gln Pro Asp Gln Thr Val Lys Lys Leu Asn His Asn Ala Ser Glu Arg
65                  70                  75                  80

Asp Arg Arg Lys Lys Ile Asn Ser Leu Tyr Ser Ser Leu Arg Ser Leu
                85                  90                  95

Leu Pro Pro Ser Asp His Thr Lys Lys Leu Ser Ile Pro Ser Thr Val
            100                 105                 110

Ser Arg Ile Leu Lys
            115

<210> SEQ ID NO 25
<211> LENGTH: 238
<212> TYPE: PRT
<213> ORGANISM: Triticum aestivum

<400> SEQUENCE: 25

Met Gly His Gln His Gln Met Phe Asn Asp Pro Phe Ala Ser Ser Met
1               5                   10                  15

Ser Ser Leu Glu Glu Asp Met Phe Ser Gly Ala Gly Tyr His His
            20                  25                  30

Leu Thr Pro Ser Met Gln Trp Pro Gly Leu Asp Asn Asp Ile Pro Ser
            35                  40                  45

Ala Pro Ala Ala Asn Asn Ala Thr Ser Ser Gly Gly Ser Gly Ser His
    50                  55                  60

Arg Lys Met Ser His Asn Ala Tyr Glu Arg Asp Arg Arg Lys Gln Leu
65                  70                  75                  80

Asn Glu Gln Tyr Ser Ser Leu Arg Ser Leu Leu Pro Asp Asp His
                85                  90                  95

Thr Lys Lys Met Ser Ile Pro Thr Thr Val Ser Arg Val Ile Asn Tyr
            100                 105                 110

Ile Pro Glu Leu Gln Lys Glu Val Asp Arg Leu Glu Lys Lys Lys Glu
            115                 120                 125

Glu Leu Arg Arg Gly Ser Cys Glu Gln Gly Ala Met Arg Gln Asn Thr
130                 135                 140

Ala Pro Ile Val Ser Ala Thr Cys Leu Asp Asp Arg Glu Ile Met Val
145                 150                 155                 160

Gln Val Ser Leu Val Ser Thr Met Ala Gly Ala Leu Pro Met Ser Lys
                165                 170                 175

Cys Ile Lys Val Leu Glu Asn Gln Gly Leu Arg Leu Ile Asn Ser Ser
            180                 185                 190

Thr Ser Ala Phe Gln Asn Arg Thr Phe Tyr Ser Leu His Leu Gln Arg
        195                 200                 205

Thr Gln Arg Thr Met Ser Lys Glu Gly Gln Thr Phe Cys Asn Glu Leu
    210                 215                 220

Glu Asn Ala Val Lys Gln Lys Ala Gly Leu His Leu His His
225                 230                 235

```
<210> SEQ ID NO 26
<211> LENGTH: 206
<212> TYPE: PRT
<213> ORGANISM: Triticum aestivum
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (168)..(169)
<223> OTHER INFORMATION: Xaa can be any naturally occurring amino acid

<400> SEQUENCE: 26

Met Gly His Gln His Gln Met Phe Glu Asp Pro Phe Ala Ser Ser Ile
1               5                   10                  15

Ser Ser Leu Glu Ala Glu Ile Phe Ser Val Ala Gly His His His
            20                  25                  30

Thr Gln Trp Pro Gly Leu Asp His Asp Ile Pro Leu Ala Pro Ala Ala
        35                  40                  45

Asn Asn Gly Thr Ser Ser Gly Gly Tyr Gly Ser Pro Gly Gly Gly Asp
50                  55                  60

Gly Ser Gly Ser His Arg Lys Ile Ser His Asn Ala Tyr Glu Arg Asp
65                  70                  75                  80

Arg Arg Lys Gln Leu Asn Glu Leu Tyr Ser Asp Leu Arg Ser Leu Leu
                85                  90                  95

Pro Asp Thr Asp His Thr Lys Lys Leu Ser Ile Pro Ile Thr Val Ser
            100                 105                 110

Arg Val Leu Lys Tyr Ile Pro Glu Leu Gln Lys Gln Val Asp Gly Leu
        115                 120                 125

Glu Lys Lys Lys Glu Glu Leu Thr Arg Ala Ser Cys Lys Pro Gly Val
130                 135                 140

Leu Thr Met Lys Gly Asp Thr Ala Pro Ile Val Ser Xaa His Cys Leu
145                 150                 155                 160

Asp Asp Arg Glu Ile Met Val Xaa Xaa Gln Leu Val Ser Thr Met Gly
                165                 170                 175

Gly Val Cys His Val Lys Cys Ser Gly Ala Glu Thr Lys Ala Arg Leu
            180                 185                 190

Ile Val Val Thr Pro Val Gln Thr Asp Ser Ile Phe Ile Ser
        195                 200                 205

<210> SEQ ID NO 27
<211> LENGTH: 144
<212> TYPE: PRT
<213> ORGANISM: Triticum aestivum

<400> SEQUENCE: 27

Met Gly His Gln His Gln Met Phe Glu Asp Pro Phe Ala Ser Ser Ile
1               5                   10                  15

Ser Ser Leu Glu Ala Asp Ile Phe Ser Val Ala Ala Gly His His His
            20                  25                  30

Pro Gln Trp Pro Gly Leu Asp His Asp Val Pro Leu Ala Pro Ala Ala
        35                  40                  45

Asn Asn Gly Thr Ser Ser Gly Tyr Gly Ser Pro Gly Gly Gly Asp
50                  55                  60

Gly Ser Gly Ser His Arg Lys Ile Ser His Asn Ala Tyr Glu Arg Asp
65                  70                  75                  80

Arg Arg Lys Gln Leu Asn Glu Leu Tyr Ser Asp Leu Arg Ser Leu Leu
                85                  90                  95
```

```
Pro Asp Thr Asp His Thr Lys Lys Leu Ser Ile Pro Ile Thr Val Ser
        100                 105                 110

Arg Val Leu Lys Tyr Ile Pro Glu Leu Gln Lys Gln Val Asp Gly Leu
    115                 120                 125

Glu Lys Lys Lys Glu Glu Leu Thr Arg Ala Asn Cys Ser Pro Ala Cys
130                 135                 140

<210> SEQ ID NO 28
<211> LENGTH: 87
<212> TYPE: PRT
<213> ORGANISM: Triticum aestivum

<400> SEQUENCE: 28

Asn Asn Ala Thr Ser Ser Gly Gly Ser Gly Ser His Arg Lys Met Ser
1               5                   10                  15

His Asn Ala Tyr Glu Arg Asp Arg Arg Lys Gln Leu Asn Glu Gln Tyr
            20                  25                  30

Ser Ser Leu Arg Ser Leu Leu Pro Asp Asp Asp His Asn Lys Lys Met
        35                  40                  45

Ser Ile Pro Thr Thr Val Ser Arg Val Ile Lys Tyr Ile Pro Glu Leu
    50                  55                  60

Gln Lys Glu Val Asp Gly Leu Glu Lys Lys Lys Glu Glu Leu Arg Arg
65                  70                  75                  80

Ala Ser Tyr Glu Gln Ala Pro
                85

<210> SEQ ID NO 29
<211> LENGTH: 762
<212> TYPE: DNA
<213> ORGANISM: Arabidopsis thaliana

<400> SEQUENCE: 29
atgtgtgcat tagtcccttc attttcaca  aacttcggtt ggccgtcaac gaatcaatac      60
gaaagctatt acggtgccgg agataaccta ataacggca  catttcttga attgacggta     120
ccacagactt atgaagtgac tcatcatcag aatagcttgg gagtatctgt tcgtcagaa      180 ggaaatgaga tagacaacaa tccggttgtg gtcaagaagc ttaatcacaa tgctagtgaa     240
cgtgaccgac gcaagaagat caacactttg ttctcatctc tccgttcatg tcttccagct     300
tctgatcaat cgaagaagct aagtattcct gaaacggttt caaagagctt aaagtacata     360
ccagagctgc aacagcaagt gaagaggcta atacaaaaga aggaagaaat tttggtacga     420
gtatcgggtc aaagagactt tgagctttac gataagcagc aaccaaaggc ggtcgcgagt     480
tatctctcaa cggtttctgc cactaggctt ggtgacaacg aagtgatggt ccaagtctca     540
tcgtccaaga ttcataactt ttcgatatca aatgtgttgg gtgggataga agaagatggg     600
tttgttcttg tggatgtttc atcatcaaga tctcaaggag agaggctctt ctacactttg     660
catcttcaag tggagaatat ggatgattac aagattaatt gcgaagaatt aagtgaaagg     720
atgttgtact tgtacgagaa atgtgaaaac tcgtttaact ag                       762

<210> SEQ ID NO 30
<211> LENGTH: 753
<212> TYPE: DNA
<213> ORGANISM: Brassica napus
```

<400> SEQUENCE: 30

```
atgtgtgcat tagtccctcc attgttccca aactttgggt ggccgtcgac aggagagtac      60
gagagtaact acctggccgg agtgaacctc gaggacttta cgtttcttga ttttccggca     120
ccagagacat atggagtgga acatcatcag gagattcagg aaatgttggg ggtctctgtt     180
ccgtccgagg ggaatggagt tgtaaccaag aagcttaatc acaatgctag tgagcgtgac     240
cgtcgcaaga gatcaactc tttgttctcg tctctccgtt catgtctccc agcttctgat      300
caaacgaaga agctaagtat tcctcagacg gtttctcgga gcttgaagta cattccagag     360
ctgcaagagc aagtgaagaa gctaatacaa aagaaggaag aactcttggt gcgagtatca     420
ggtcaaagag ccattgaaca ttatgttgag ccgcagccaa aggccgttgc acgttacgtc     480
tcgaccattt ctgcgactaa gcttggagac aacgaagtgc tggtccaaat ctcatcgtcc     540
aagaatcata acttttcgat atctaatgtg ttgagtgggt tagaagaaga tgggtttgtt     600
cttgttgatg tttcatcttc caggtatcat ggaaaatggc tcttctactc tttgcatctt     660
caaatgggaa ataaagataa tcacaaactg aagtgcgaag agctaagcca gagaattttg     720
tacttgtatg aggaatgtga aaactcattt aga                                  753
```

<210> SEQ ID NO 31
<211> LENGTH: 765
<212> TYPE: DNA
<213> ORGANISM: Brassica oleracea
<220> FEATURE:
<221> NAME/KEY: misc_feature
<222> LOCATION: (758)..(760)
<223> OTHER INFORMATION: n is a, c, g, or t

<400> SEQUENCE: 31

```
atgtgtgcat tagtccctcc actgttcccc gactttgggt ggccgtcgac ggcaggttac      60
gagagctact acctcggcgg agaaaacctc aacaacgaca tgtttcttga ttttccggtt     120
gtggaaactt atggagtatt ggctcatcat cagaacagct taggagtttc tgtttcgtcg     180
gagggaaatg gaatagacaa caacccggtt gttaaaaaga agcttaatca caatgctagt     240
gagcgtgacc gtcgcaagaa gatcaactct ttgtttgcat ctctccgctc atgtcttcca     300
acctcagatc aatcgaaaaa gctaagcatt tcagccaccg tttcacgaag cttgaagtac     360
ataccagagt tgcaagagca agtgaagaag ttattacaaa agaaggaaga actcttggtt     420
cgagtatcag gtcaacgaga cattgaactt tacgttaagc cacaaccaaa ggcaattgca     480
agttatgtct ccactgtttc cgcgactagg cttggagaca acgaagtgat ggtccaaatc     540
tcatcatcca agattcataa cttctcgata tctaaagtgt taactggatt agaagaagat     600
ggttttgttc ttgtggatgt ttcatcttca aggtttcaag gggaaaggct tttctacact     660
ttgcatcttc aagtagaaaa tatggatgat cattacaaaa tgaattgcga agagttaagt     720
gaaaggatgt tgtacttgta cgaggaatgt gaaaattnnn ttagg                     765
```

<210> SEQ ID NO 32
<211> LENGTH: 435
<212> TYPE: DNA
<213> ORGANISM: Brassica rapa

<400> SEQUENCE: 32

```
attcctcaga cggtttctcg gagcttgaag tacataccag agctacaaga gcaagtgaag      60
aagctaatac aaaagaagga agaactcttg gtgcgagtat caggtcaaag agacattgaa     120
cattacgttg agccgcaccc aaaggccgtt gcacgttacg tctcgaccat ttctgcgact     180
```

```
aagcttggag acaacgaagt gatggtccaa atctcatcgt ccaagaatca taacttttcg    240
atatctaatg tgttgagtgg gttagaagaa gatgggtttg ttcttgttga tgtttcatct    300
tcaaggtctc atggagaaag gctcttctac actttgcatc ttcaaatggg aaataaagat    360
gattacaaac tgacatgcga agagctacgc cagagaatgt tatacttgta tgaggaatgt    420
ggaaactcgt ttaga                                                    435

<210> SEQ ID NO 33
<211> LENGTH: 300
<212> TYPE: DNA
<213> ORGANISM: Cicer arietinum

<400> SEQUENCE: 33
attccaactc cctcacaagc cacaagcagc gaccttagca tggtcaagaa acttatccgc     60
aatgctagtg aacgagatcg ccgcaagaaa atcaatactt tgtattcttc acttcgttca    120
cttcttcctg tggcagaaca gatgaagaag ttgagcaatc cggcaacaat ttcacgagtc    180
ctaaagtaca tacgtgagtt acagaagcag gtagaaggac tacttacgag aaaggaggcg    240
attttattga aactatctcc agaagtagat gaggtgaaga gtaaagaatc tgagaggaag    300

<210> SEQ ID NO 34
<211> LENGTH: 501
<212> TYPE: DNA
<213> ORGANISM: Hordeum vulgare

<400> SEQUENCE: 34
agcgaccgcc gcaagcagct caacgagcaa tattcctccc tccgctccct cctccccgat     60
gacgatcaca ataagaagat gagcattccg accacggtgt cgcgggtgat caagtacatc    120
ccggagctac agaaggaggt cgacggtctg gagaagaaga aggaggagct caggcgagct    180
agcagcgagc aaggcgtgct gactatgagg cagaacacgg ctcctgtcgt ctccgccacc    240
tgcctcgacg acagggaaat catggtccag gtcagtctgg tgagcaccat ggccgcagct    300
ctgcccatgt ccaagtgcat caaggtgctg gagaacgaag gccttcgcct cataaattcc    360
tcgacttccg cgttccagaa caggaccttc tatagcctcc atcttcagag aacccaacga    420
acaatgagca aggagggcca acatttttgt aacgaactgg agaacgccgt gaagcaaaag    480
gcaggactgc atctgcatca t                                             501

<210> SEQ ID NO 35
<211> LENGTH: 759
<212> TYPE: DNA
<213> ORGANISM: Hordeum vulgare

<400> SEQUENCE: 35
atggggcacc agacccagat gttcgacgac ccgttcgcga gcagtatgtc gtccctggac     60
gcagacatct tctccgtcgc cggcggcctc cacccatcgc agtggccggg actcgaccac    120
gacgtctcgc tggcgccggc tgccaacaac ggcacctcct ccggcggcta cggctccccc    180
gggggcggcg atggctcggg ctcccaccgc aagatcagcc acaacgcgta cgagcgcgac    240
cgccgcaagc agctcaacga gctctactcc gacctccgct ccctcctccc cgactccgat    300
cacaccaaga agctgagcat tccgatcacg gtgtcgcgcg tgctcaagta catcccggag    360
ctgcagaagc aggtggacgg actggagaag aagaaggagg agcttacgcg gccagctgc    420 aagccaggcg tattgaccat gaaggagaac acggtcccga tcgtgtccgc cacctgcctc    480
gacgaaaggg agatcatggt ccaggttagc ttggtgagca ccatggccgg agctctgccc    540
```

```
atgtccaagc gcatcaaagt gctggagaac gaaggcctcc gcctcatcag ctcgtccact    600
tctgctttcc agaacaggac gttctatagc ctccatcttc agagaaccca acggacgatg    660
agcaaagagt gtccggcatt tgtgaagaa ctggagaatg ccctgacgca aaggcgggg    720 tacgtctaca tcaccagtag attatatgta gcagaataa                          759
```

<210> SEQ ID NO 36
<211> LENGTH: 767
<212> TYPE: DNA
<213> ORGANISM: Medicago truncatula

<400> SEQUENCE: 36

```
atgttagcga tatctcctcc tatgttttca acaattggat ggccctttga ggagccttta     60
agccataacc agcatcagaa ttcattctac aaagacactg ttgatcaatt atttaatttt    120
catgatcaag ttgaggcaga aattaattca acagatccct cacaatccac aagcagtgac    180
cttagcatgg tcaagaagct tgttcataat gccagtgaac gcgatcgccg caagaagatc    240
aataatttgt attcatcact tcgatcactc cttcctgttt ctgatcaaat gaaattaagc    300
attccgggaa caatttctag agtcctgaaa tacatacctg aattacagaa tcaagtagag    360
ggactaatta agagaaagga tgagatctta ttgggacttt ctccacaagt agaagagttt    420
attctaagca aagaatctca aaggaagaag catagttaca actctggttt tgtagtttca    480
agtagtaggc tcaatgatag tgaaattacc attcagattt catgttacac tgtccaaaag    540
attccacttt ctgagatctt gatttgtttg gaaaatgatg ccttttgct gcttaatgtt    600 tcttcatcaa agacctttgg agggagggtc ttctataatt tgcatttcca ggtggataaa    660
acacagatat tagaatctca tattctaaat gagaagctct tatcaataat ggagaaggaa    720
ggagagtttt aaaacaata attaaagttt aggatttggc tctttaa                    767
```

<210> SEQ ID NO 37
<211> LENGTH: 780
<212> TYPE: DNA
<213> ORGANISM: Medicago truncatula

<400> SEQUENCE: 37

```
atggttgcat tctgcccacc tcagttctca tactcaaaca tgggatggct cttagaggag     60
ttagagccag agtccttaat tagtcataaa gagaagaact atgcatcttt agagtactcg    120
ttaccgtatc atcaattctc ttcaccaaag gaacatgttg aaattgaaag gccaccatcc    180
cctaaactta tggccaagaa acttaaccac aatgctagtg aacgtgatcg ccgcaagaag    240
attaatagct tgatttcttc acttcgttca cttcttcccg gtgaagatca aacgaaaaaa    300
atgagcattc cggtaacaat ttcacgtgtc ttaaaataca tccctgattt acaaaagcag    360
gtgcaaggac ttaccaagaa aaagaagag cttctatcaa gaatttctca tcgacaagaa    420
tatgcagtta caaagaatc acaaggaag aaaattccaa attacaattc tgcttttgta    480
gtttcaacaa gtaggcttaa tgatactgag cttgttattc atatttcgtc ttatgaggcc    540
aacaagattc ctctatctga gatcttgatg tgtttagaaa ataatggtct tcttctactt    600
aactcttctt cttctaaaac ctttggaggg aggctcttct ataacttgca ttttcaggtg    660
gataaaactc aaagatatga gtgtgatgat ctgattcaaa agcttcttc aatatatgag    720 aagcagcaaa ataatcattt gggcactatg gatcaaacga tcaatagtgg tctgatatat    780
```

<210> SEQ ID NO 38
<211> LENGTH: 300
<212> TYPE: DNA
<213> ORGANISM: Medicago truncatula

<400> SEQUENCE: 38

```
atgttagcga tatctcctcc tatgttttca acaattggat ggccctttga ggagcccttta      60 agccataacc agcatcagaa ttcattctac aaagacactg ttgatcaatt atttaattt      120 catgatcaag ttgaggcaga aattaattca acagatccct cacaatccac aagcagtgac     180
cttagcatgg tcaagaagct tgttcattat gccagtgaac gcgatcgccg caagaagatc     240
aataatttgt attcatcact tcgatcactc cttcctgttt ctgatcaaat ggtacttaat     300
```

<210> SEQ ID NO 39
<211> LENGTH: 690
<212> TYPE: DNA
<213> ORGANISM: Panicum virgatum

<400> SEQUENCE: 39

```
atggagcacc agctgttcga tgaccccttc tctagcagca tctcgtcgct ggaggcggac      60
atcttctccg ccggcggcca gctgccgtcg ccgccgtggc cggacctcga cctcgacctc     120
gacgacgacg acatccacga cctctccgcg ccgaccggca accccacctc ctcaggaggc     180
tatggctcgg gcggaggctc cggaggctcc cacaggaagc acagccacaa cgcgtacgag     240
cgcgaccgcc ggaagcagct caacgagctc tactcctcgc tccgctccct cctccccgac     300
gctgaccaca ctaagaagct gagcatcccc accacggtct cccgagttct caagtacatc     360
cccgagctgc agaagcaggt ggacaacctg gagaggagga agaaagagct gacgaacgcc     420
aactgcaaac caggagttct gaacacgagc cagattgtaa ctcccattgt ttctgctact     480
tgcctcaacg atacggagat catggttcag gtcagcctgc acagcaacgt ggctgccaca     540
agtcttcctc tgtccaagtg cataaaagtg atggagaatg aaggccttca cctaattagt     600
tcatcaactt actccacctt cgacaacagg acattctata gcctccatgt tcagagaagt     660
caaagaacga tgaaagagga gtgcccagca                                      690
```

<210> SEQ ID NO 40
<211> LENGTH: 549
<212> TYPE: DNA
<213> ORGANISM: Populus

<400> SEQUENCE: 40

```
atggtcaaga aacttagcca caacgctaat gaacgtgacc gtcgcaagaa gattaaaagt      60
ttgtattctt cacttcgttc acttctccca gcagcagatc aaatgaagaa attaagcgtg     120
ccggccactg tttcacgtgc gcttaagtac ctaccagagc ttcaacagca agtggagaga     180
ctggttcaaa gaaaggagga gcttttatca aagttatcaa agcaaggtgg tataattcat     240
caagaaaatc aaagaaatga caccgtgtat agctctttat catcggtatc ggcaagccag     300
cttagtgata gagaagttgt cgttcatatt tccacttaca agaaccataa aagtccatta     360
tcagaaatct tgctcacctt agaggaagat ggacttgttc taaaaaactc ttcttccttt     420
gagtcatttg gggacagggt cttctataat ttacatcttc aggtcatgga aggaacttac     480
acattggata gtgaggccat gagggcgaag cttgtgtctt tatctgtaaa gagggaatca     540
tcgtctcta                                                             549
```

<210> SEQ ID NO 41
<211> LENGTH: 795
<212> TYPE: DNA
<213> ORGANISM: Populus

<400> SEQUENCE: 41

```
atgttagaag aattatctcc catcagtttg ttctcaacat ttggatggcc cttggaggaa      60
gccataagcc atgaacagca ctacagcttt agagatggtg aaactccaga gtcatttact     120
cacttccctc catctcagcc agatgtaaga cagcttgatc gctccacatc attcacggcc     180
cacagtggaa gcggtgaccc tagcatggct aagaagctta accacaacgc tagcgaacgt     240
gaccgtcgca aaaagatcaa cagtttgtat tcttcactcc gttcactact tcctgcagcc     300
gatcaaagga agaaattaag cataccgtat acagtttcac gtgtgcttgt atacatacca     360
aaacttcaac aacaagtgga gagactgatt caaaggaagg aggagcttct atcgaagtta     420
tctaggcaag ctgacgattt aactcatcaa gaaaatcaaa gaaaaggcac catgtatagc     480
tctttatcat cggtatcggc gagccggctc agtgacaggg aagttgtcat tcatatctca     540
actaacaagc tccatagaag ttcattatca gaaatcttgg ttaatttaga ggaggctgga     600
cttcttctac taaattcttc ttccttcgag tcctttggag cagagtctt ctataattta      660
caccttcagg ccatggaagg aacttacaca gtagagtgcg aggccttgaa tgagaggctt     720
gtgtccttgt gcgagaagag ggagtcattg tttccattaa attcaagttc tccatattct     780
aactgtgtat tctag                                                      795
```

<210> SEQ ID NO 42
<211> LENGTH: 474
<212> TYPE: DNA
<213> ORGANISM: Populus

<400> SEQUENCE: 42

```
gatcctaaca tggttaagaa gcttaaccac aacgctagcg aacgtgatcg tcgcaagaag      60
atcaacagtt tgtattcttc actccgttca cttcttccag cttccgatgg aatgaagaaa     120
ttaagcatac cgtccacaat ttcacgtgtg cttaagtaca taccagaact tcaacagcaa     180
gtggagagac agatccaaag gaaggaggag cttctatcaa atctatctcg gcaagatgat     240
ttaattcatc aagaaaatca agaaaaagac accatgtata gctctttatc atcggtatcg     300
gcaagccggc ttggtgatag agaagttgtc gttcaaattt ccacttgcaa ggtccttaaa     360
agcccaatat cagaaatctt gcttaattta gaggaaaatg acttgttct aataaattct      420
tcttcctttg agtcctttgg aggcaacgtc ttctaccatt tacatcttca ggta           474
```

<210> SEQ ID NO 43
<211> LENGTH: 774
<212> TYPE: DNA
<213> ORGANISM: Ricinus communis

<400> SEQUENCE: 43

```
atgttagcat tatctcctcc tgtatttcca acacctgaat ggcccttaga ggacccctta      60
ggcattgacc aaatctccta cttctgtaga gaaactcagc ctgctactgc tgcttttctt     120
ccatcttatc agcaagagtt attattatta gagcttgatc atcaacaatc cacatctttc     180
acagcctata atagcagtgg tggtgacgct aacgatatgg tgaagaagct taatcataat     240
gcaagcgaac gtgatcgtcg caagaagatg aacaccctct attcttccct ccgatcacta     300
tttccggccg ccgatgaaat gaagaagctg agtataccct ccacaatttc gagggtgttg     360
```

```
aagtacatac cagaactaca agaacagtta gagagattgg tccaaaggaa ggaagagatt    420
ttgctaagaa tatctaagca aaatcatatt gttaatcccc aaataaacca aagaaaaggc    480
acttctcaca gcagtttatc agtagtatca gctaatcaaa ttagtgacaa agaagccatt    540
attcaaattt ctacgtacag taatactatc catacaagtc cactatcaga aatcttgctt    600
cttttggagg aggaaggcct tcttttgatt aattcttctt ccgctgaatc ctttggtggc    660
agggtcttca acaatttaca tgttcaggtt gatgatactt atacattgga atgtgatgct    720
ttaagtgaga agcttgcatc tctgtatgcc aagagggacg ggctgttccc atga          774
```

<210> SEQ ID NO 44
<211> LENGTH: 555
<212> TYPE: DNA
<213> ORGANISM: Ricinus communis

<400> SEQUENCE: 44

```
atggtcaaga agcttaatca taatgcaagc gaaagggatc gccgcaagaa gatgaacact     60
ctctattctt ccctccgatc acttcttccg gcctccgatc aaatgaagaa gctgagcata    120
cctgccacaa tttccagggt gttgaagtac ataccagaac tacaacaaca attggagaga    180
ttcgtccaaa ggaaagaaga actattactg agaatatcta gcagaatcaa tattattaat    240
ccccaaataa accaagaaaa aggcactact cacagcacct tatcagtagt atcagctaat    300
caaattagtg acaagaagt tgttattcaa gtttctactt acaataatac tatccataca    360
agtccattat cagaaatctt gcttcttctg gaggaggaag ccttcttct gattaattct    420 tcctcctttg agtcctttgg aggcagggtc ttctacaatt tacatcttca ggttgatgga    480
acttatatat tggagtgtga tgctttaagc gagaagcttg cagctttata tgagagagac    540
gggttatttc catga                                                    555
```

<210> SEQ ID NO 45
<211> LENGTH: 717
<212> TYPE: DNA
<213> ORGANISM: Solanum lycopersicum

<400> SEQUENCE: 45

```
acaacgataa taactacgcc tcaatttcaa actgatcaga ataacaagtt gtttgaaggt     60
ttacgtgccg ataatactat tgatttacct tcatctcatc attatcaaca acaatgtttg    120
aaaggaagtg agtttgatgt tgatgagtta ggggtagaaa ggtcattaat ggagaagaag    180
ctaaatcata atgcaagtga acgtaataga aggaagaaga tgaattttct ttattcaact    240
cttcgttctt tgcttcctcc tcctactaat aaacatcaaa agaaaaaatt aagctttcca    300
gcaacagtat catatgtaca agaatacatc ccagagttga agaaagaaat agagaggcta    360
agcaaaacaa aagatttgct tttatcaaag aaatcaaatt attcattact caaaattgat    420
gataataata agagaaaatt aattattggt ggaacttctt gtaattcttc aacaacatca    480
atttgtgcaa gtcaactaag taattcacaa gttttggtac aaatttcaac aactcaagaa    540 aataatttc caatttcaca agtatttgca agtgtagagg aagatggatt aattttgcta    600
aatgcatcat cctttaaatc ttttggagac aagattttc acagcttgca ttttcagatg    660
caaggaccaa ttgaaatgga cattcaggtt ttgaagacta agcttttagt aatgtgt        717
```

<210> SEQ ID NO 46
<211> LENGTH: 642
<212> TYPE: DNA
<213> ORGANISM: Sorghum bicolor

<400> SEQUENCE: 46

```
atggaccatc agctgttcga cgacccttc gggagcagca tctcgtcgct ggaggcggac      60
atcttctccg ccggcggcgg cggacagctg ccgtcgccgc cgtggccgga cctcgacctc     120
gacgacgact acgacataca cgacctctcc gcgccggccg ccaacgccgc cacctcctcg     180
ggaggaggct atggctccgg cggctccggc aggaagctca gccacaacgc atacgagcgc     240
gaccgccgga agcagctcaa cgagctctac tcctcgctcc gatccctcct ccggacgct      300
gatcacacta agaagctgag catccccacc accgtgtccc gagttctcaa caccaaagag     360
atcgtaactc ccattgtttc tgctacttgc cttaacgaca cggagatcat ggttcaggtc     420
agcctgcaca gcaatgtggc cgccacagct ctccctctct ccaagtgcat aaaggtgcta     480
gaaaacgaag gccttctcct cgtcagctca tcaacctact ccaccttcga gaacaagaca     540
ttctatagcc tccatcttca gagaagtcaa agaacgatga aggagcagtg cccaggattc     600
tgcgacgaac tggagaagat cgtcaggaag aaagcagggg cg                        642
```

<210> SEQ ID NO 47
<211> LENGTH: 672
<212> TYPE: DNA
<213> ORGANISM: Triticum aestivum

<400> SEQUENCE: 47

```
atggagcatc aactattcga cgacgccgtc ccgagcagca tgatctggcc gttagaggca      60
gaaaacggtt tcaccgacga gctgccgtct ttgcagttac cggacgtgga ccttgacttc     120
gacatccacg agttctccgc accggcaacg gcaccggcga agcggcctc ctcgggtggc      180
tccggattgg ttggttccgg ttcaggatcg cataagaagc tcaaccacaa cgcgtacgag     240
cgcgaccggc ggacgcagct caatcagctc tactcgactc tccgttctct catccccaac     300
gcagatcaca caaagaagct gagcattccg acgacggtgt gtcaggtcct cgactacata     360
cccaagctgc agaagcaggt cgaggatctc aagaagaaga acaggagct cagtacagcc     420
aaatgcagag aaagactgca gcgcgtcaag gacaacacat gccgtattgt ttctgccact     480
cctctcgatg gcaacgaaat catggtccag gttagcctgc tgagcaacat ggctgcaagt     540
cttcctctat ccaagtgcat aaacgtattt gagaacaaag ggcttcacct catcagttca     600
tcgactttct ccaccgaggt caatagaaca ttttacagct tccactttga ggtacgtttt     660
tacatgcgcc ct                                                        672
```

<210> SEQ ID NO 48
<211> LENGTH: 390
<212> TYPE: DNA
<213> ORGANISM: Triticum aestivum
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t

```
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (379)..(380)
<223> OTHER INFORMATION: n is a, c, g, or t

<400> SEQUENCE: 48
ggcgatggct cgggctccca tcgcaagatc agccacaacg cctacgagcg cgaccgccgc      60
aagcagctca acgagctcta ctccgacctc cgctccctcc tccccgacac cgatcacacg     120
aagaagctta gcattccgat cacggtgtcg cgggtgctca agtacatccc ggagctgcag     180
aagcagtggg cttgnagaaa naaagaagga ggagntgacg cgcgccaact gcaacccggn     240
gtgntgacca tgaaggggaa cacggtccga ttgttccgcc acctgcctcg acgacgggga     300
nattatggtc caagtcaacc tggtgagcac atggccggan tntgcccatt tcaaatgcat     360
caaagtgctg gaaaacaann gctccggtca                                      390

<210> SEQ ID NO 49
<211> LENGTH: 459
<212> TYPE: DNA
<213> ORGANISM: Triticum aestivum

<400> SEQUENCE: 49
atggagcagc tgttcgtcga cgacccagcc ttcgcgagca gcatgtcgtc gcttgaggcg      60
gacatcttct ccggcgccgg ccagctgccg tcctcgccgt ggctggacct agacctcgac     120
gacgatgtcc aagacctctc catggcgccg acgacggcga acgcggtgtc ctccggctac     180
ggctccggcg gatccggctc ccacaggaag ctcagccaca acgcctacga gcgcgaccgc     240
cggaagcagc tcaacgagct ctactcctcc ctccgcgctc tcctcccgga cgccgatcac     300
actaagaagc tgagcatccc gacgacggtg tctcgcgtgc tcaaatacat acccgagctg     360
cagaagcagg tggagaatct ggagaggaag aagaaggagc tgacgacgac gagcaccacc     420
aactgccaac caagagtgtt ggggagccag ctgatgagc                            459

<210> SEQ ID NO 50
<211> LENGTH: 732
<212> TYPE: DNA
<213> ORGANISM: Vigna unguiculata

<400> SEQUENCE: 50
atggtcgcat tgttctctcc tcctctcttc tcaaccaaag ggtggctctt agaggaggag      60
ccattcggct ataataatac ccataatctc tcctacaaag atgatgcgtc ttctcagtac     120
tcctttccct atcaatttta ttcaccacag acacagattg aggttgaaat tgaaaggtcc     180
actgcaccat cctctgaccc tgccatggtc aagaaactta gccacaatgc tagcgaacgt     240
gatcgccgca agaaggtcaa caacttggtt tcttcacttc gctcacttct tccaatggca     300
```

```
gatcaaacga aaaaaatgag cattcctgca acagtttcca gagtgttgaa atacatacct      360
gaactacaac agcaagtgca agcactaaca aagagaaaag aggagcttct gtgcagaatt      420
tctcggcaat tgcaaggaga agcagtgaac aaagaatctc agagaaaaat ttcccatcac      480
aactcttctt tgttgtctc aacgactagg cttaacgatt gtgaagctgt agttcacatt       540
tcatctcatg agacacacaa ggctccacta tcagagattc tgcagtgctt agaaaatgat      600 ggccttttc tgctacatgc ttcttcctca gaaacctttg gaggaaggtt cttctacaat       660
ttgcattttc acgtggagaa aactgataga ttagagaccg agattttaac tgagaagctt     720
ttaccaatat at                                                          732

<210> SEQ ID NO 51
<211> LENGTH: 1563
<212> TYPE: DNA
<213> ORGANISM: Vitis vinifera

<400> SEQUENCE: 51
atgttagcat tctcccctcc attgtttcca acccttggat ggcccttgga ggatcccata       60
agccatgcac agaactacat atatggagaa acagaaactt cagaatcgtt tcttcacttg      120
ccctcatctc agccacaagt ggaactcaat tgctccaccc catatgcagc agttagtggt      180
aatcccacga tggttaagaa acttaaccac aacgtcagtg tgcgggatcg tcggaagaag      240
atcaacagct tgtactcctc tctgcgttca ctacttccat cagctgatca agtgaagaaa      300
ttaagcattc cttcgacagt ttcatgtgtg ctaaaataca taccagagct gcaacggcaa      360
gtggagagac tgatccaaaa gaagaagag ttttatcaa agatttctag ggaaggagat         420
ctaattcacc tagaaaatca agaaatggc acacttggaa gctctttatc tgctgtttca      480
gcaagaaggc ttagtgacag ggaaattgtg gttcagatat ccacatttaa ggtccatgag      540
agtccacttt ctgaggtttt gttaaatttg gaggaggatg gcttcttgt aatcaatgca      600 tcatcttttg agtcctttgg agggagggtc ttctacaact tacatcttca ggttgaagga     660
actcaaggaa tggagtcgac cgcccacttg gagatgacaa gaactctaaa aaacaaacac     720
atgaatatat tggtgattca tatggacttt cctccttttt ttcttaagat gttcctgatc     780
tttacaagag tatttaccaa tcatatatca acttcctacc aatgctatgt tggtaaatta     840
attatcattc tactgctaca tgtaattaag aaagaaaatt ttgaaacttc taaacatcaa     900
ttggccagcg ccgaaccaat aattgtagca ggtcaagctg ccaaaaaatt ggatgatgag     960
cttctcttgg aaaccaagat gaaaactgaa gggatgggag tactggaaac accaatattg   1020
attaaagcaa agaatggtac caagaaatg gtggagagaa tccttgatct ttaccccatg    1080
gcaattcatg acatagactc caacaagaag aatatagtgc tattggcggt ggagaatagg   1140 caccccatg tgtatgagct cttcctgaag agaaatattg tgaaagatag tgtatttggt    1200
gcagttgata ataaaggcaa cagtgcattg catctggctg ccatgtttgc agattatcgg   1260
ccttgggtca ctcctggtgt tgcattgcaa atgcaatggg aagtcaaatg gtatgagtat   1320
gtgaagaagt ccatgccacc aaatttcttc cgtttccaca acaatgaaaa caagtctaca   1380
aagcagattt tcacccgtga acacagagat ctggtgcaaa agggtgggca atggctaaat   1440
aacacagcca cctcatgctc gttggtagta acactcattg caacagttgc cttcgccaca   1500
tcaactgctg taccgggcgg caccaaggag gggactgatt catgtcctct caatggtccc   1560
taa                                                                  1563
```

<210> SEQ ID NO 52
<211> LENGTH: 735
<212> TYPE: DNA
<213> ORGANISM: Vitis vinifera
<220> FEATURE:
<221> NAME/KEY: misc_feature
<222> LOCATION: (293)..(293)
<223> OTHER INFORMATION: n is a, c, g, or t

<400> SEQUENCE: 52

```
atgttagcat tctcccctcc attgtttcca acccttggat ggcccttgga ggatcccata      60
agccatgcac agaactacat atatggagaa acagaaactt cagaatcgtt tcttcacttg     120
tcctcatctc agccacaagt ggaactcaat tgctccaccc catctgcagc agttagtggt     180
aatcccacga tggttaagaa acttaaccac aacgccagtg agcgggatcg tcggaagaag     240
atcaacagct tgtactcctc tatgcgttca ctacttccat cagctgatca agngaagaaa     300
ttaagcattc cttcgacagt ttcacgtgtg ctaaaataca taccagaact gcaacgacaa     360
gtggagagat tgattcaaaa gaagaagag tttttatcaa agatttgtag ggaaggagat     420
ccaattcacc tagaaaatca agaaatggc acacttggaa gctctttatc tgctgtttca     480
gcaagaaggc ttagtgacag ggaaattgtg gttcagatat ccacatttaa tgtccatgag     540
agtcctcttt ctgaggtttt gttaaatttg gaggaggatg gcttcttgt aatcaatgca     600
tcatcttttg agtcctttgg agggagggtc ttctacaact tacatcttca ggttgaagga     660
actcaaggaa tggagtgtga gttgttgagc gagaagctac tttcattgtg tgaaaggaga     720
gaggcttttc catga                                                     735
```

<210> SEQ ID NO 53
<211> LENGTH: 253
<212> TYPE: PRT
<213> ORGANISM: Arabidopsis thaliana

<400> SEQUENCE: 53

Met Cys Ala Leu Val Pro Ser Phe Phe Thr Asn Phe Gly Trp Pro Ser
1               5                   10                  15

Thr Asn Gln Tyr Glu Ser Tyr Tyr Gly Ala Gly Asp Asn Leu Asn Asn
            20                  25                  30

Gly Thr Phe Leu Glu Leu Thr Val Pro Gln Thr Tyr Glu Val Thr His
        35                  40                  45

His Gln Asn Ser Leu Gly Val Ser Val Ser Ser Glu Gly Asn Glu Ile
    50                  55                  60

Asp Asn Pro Val Val Val Lys Lys Leu Asn His Asn Ala Ser Glu
65                  70                  75                  80

Arg Asp Arg Arg Lys Lys Ile Asn Thr Leu Phe Ser Ser Leu Arg Ser
                85                  90                  95

Cys Leu Pro Ala Ser Asp Gln Ser Lys Lys Leu Ser Ile Pro Glu Thr
            100                 105                 110

Val Ser Lys Ser Leu Lys Tyr Ile Pro Glu Leu Gln Gln Gln Val Lys
        115                 120                 125

Arg Leu Ile Gln Lys Lys Glu Glu Ile Leu Val Arg Val Ser Gly Gln
    130                 135                 140

Arg Asp Phe Glu Leu Tyr Asp Lys Gln Gln Pro Lys Ala Val Ala Ser
145                 150                 155                 160

Tyr Leu Ser Thr Val Ser Ala Thr Arg Leu Gly Asp Asn Glu Val Met
                165                 170                 175

```
Val Gln Val Ser Ser Lys Ile His Asn Phe Ser Ile Ser Asn Val
            180                 185                 190

Leu Gly Gly Ile Glu Glu Asp Gly Phe Val Leu Val Asp Val Ser Ser
        195                 200                 205

Ser Arg Ser Gln Gly Glu Arg Leu Phe Tyr Thr Leu His Leu Gln Val
    210                 215                 220

Glu Asn Met Asp Asp Tyr Lys Ile Asn Cys Glu Glu Leu Ser Glu Arg
225                 230                 235                 240

Met Leu Tyr Leu Tyr Glu Lys Cys Glu Asn Ser Phe Asn
                245                 250

<210> SEQ ID NO 54
<211> LENGTH: 251
<212> TYPE: PRT
<213> ORGANISM: Brassica napus

<400> SEQUENCE: 54

Met Cys Ala Leu Val Pro Pro Leu Phe Pro Asn Phe Gly Trp Pro Ser
1               5                   10                  15

Thr Gly Glu Tyr Glu Ser Asn Tyr Leu Ala Gly Val Asn Leu Glu Asp
            20                  25                  30

Phe Thr Phe Leu Asp Phe Pro Ala Pro Glu Thr Tyr Gly Val Glu His
        35                  40                  45

His Gln Glu Ile Gln Glu Met Leu Gly Val Ser Val Pro Ser Glu Gly
    50                  55                  60

Asn Gly Val Val Thr Lys Lys Leu Asn His Asn Ala Ser Glu Arg Asp
65                  70                  75                  80

Arg Arg Lys Lys Ile Asn Ser Leu Phe Ser Ser Leu Arg Ser Cys Leu
                85                  90                  95

Pro Ala Ser Asp Gln Thr Lys Lys Leu Ser Ile Pro Gln Thr Val Ser
            100                 105                 110

Arg Ser Leu Lys Tyr Ile Pro Glu Leu Gln Glu Gln Val Lys Lys Leu
        115                 120                 125

Ile Gln Lys Lys Glu Glu Leu Leu Val Arg Val Ser Gly Gln Arg Ala
    130                 135                 140

Ile Glu His Tyr Val Glu Pro Gln Pro Lys Ala Val Ala Arg Tyr Val
145                 150                 155                 160

Ser Thr Ile Ser Ala Thr Lys Leu Gly Asp Asn Glu Val Leu Val Gln
                165                 170                 175

Ile Ser Ser Ser Lys Asn His Asn Phe Ser Ile Ser Asn Val Leu Ser
            180                 185                 190

Gly Leu Glu Glu Asp Gly Phe Val Leu Val Asp Val Ser Ser Ser Arg
        195                 200                 205

Tyr His Gly Lys Trp Leu Phe Tyr Ser Leu His Leu Gln Met Gly Asn
    210                 215                 220

Lys Asp Asn His Lys Leu Lys Cys Glu Glu Leu Ser Gln Arg Ile Leu
225                 230                 235                 240

Tyr Leu Tyr Glu Glu Cys Glu Asn Ser Phe Arg
                245                 250

<210> SEQ ID NO 55
<211> LENGTH: 255
<212> TYPE: PRT
<213> ORGANISM: Brassica oleracea
```

```
<220> FEATURE:
<221> NAME/KEY: misc_feature
<222> LOCATION: (253)..(254)
<223> OTHER INFORMATION: Xaa can be any naturally occurring amino acid

<400> SEQUENCE: 55

Met Cys Ala Leu Val Pro Pro Leu Phe Pro Asp Phe Gly Trp Pro Ser
1               5                   10                  15

Thr Ala Gly Tyr Glu Ser Tyr Tyr Leu Gly Gly Glu Asn Leu Asn Asn
            20                  25                  30

Asp Met Phe Leu Asp Phe Pro Val Val Glu Thr Tyr Gly Val Leu Ala
        35                  40                  45

His His Gln Asn Ser Leu Gly Val Ser Val Ser Glu Gly Asn Gly
    50                  55                  60

Ile Asp Asn Asn Pro Val Val Lys Lys Leu Asn His Asn Ala Ser
65                  70                  75                  80

Glu Arg Asp Arg Arg Lys Lys Ile Asn Ser Leu Phe Ala Ser Leu Arg
                85                  90                  95

Ser Cys Leu Pro Thr Ser Asp Gln Ser Lys Lys Leu Ser Ile Ser Ala
            100                 105                 110

Thr Val Ser Arg Ser Leu Lys Tyr Ile Pro Glu Leu Gln Glu Gln Val
        115                 120                 125

Lys Lys Leu Leu Gln Lys Lys Glu Glu Leu Leu Val Arg Val Ser Gly
130                 135                 140

Gln Arg Asp Ile Glu Leu Tyr Val Lys Pro Gln Pro Lys Ala Ile Ala
145                 150                 155                 160

Ser Tyr Val Ser Thr Val Ser Ala Thr Arg Leu Gly Asp Asn Glu Val
                165                 170                 175

Met Val Gln Ile Ser Ser Ser Lys Ile His Asn Phe Ser Ile Ser Lys
            180                 185                 190

Val Leu Thr Gly Leu Glu Glu Asp Gly Phe Val Leu Val Asp Val Ser
        195                 200                 205

Ser Ser Arg Phe Gln Gly Glu Arg Leu Phe Tyr Thr Leu His Leu Gln
    210                 215                 220

Val Glu Asn Met Asp Asp His Tyr Lys Met Asn Cys Glu Glu Leu Ser
225                 230                 235                 240

Glu Arg Met Leu Tyr Leu Tyr Glu Glu Cys Glu Asn Xaa Xaa Arg
                245                 250                 255

<210> SEQ ID NO 56
<211> LENGTH: 145
<212> TYPE: PRT
<213> ORGANISM: Brassica rapa

<400> SEQUENCE: 56

Ile Pro Gln Thr Val Ser Arg Ser Leu Lys Tyr Ile Pro Glu Leu Gln
1               5                   10                  15

Glu Gln Val Lys Lys Leu Ile Gln Lys Lys Glu Glu Leu Leu Val Arg
            20                  25                  30

Val Ser Gly Gln Arg Asp Ile Glu His Tyr Val Glu Pro His Pro Lys
        35                  40                  45

Ala Val Ala Arg Tyr Val Ser Thr Ile Ser Ala Thr Lys Leu Gly Asp
    50                  55                  60

Asn Glu Val Met Val Gln Ile Ser Ser Lys Asn His Asn Phe Ser
65                  70                  75                  80
```

```
Ile Ser Asn Val Leu Ser Gly Leu Glu Glu Asp Gly Phe Val Leu Val
                85                  90                  95

Asp Val Ser Ser Arg Ser His Gly Glu Arg Leu Phe Tyr Thr Leu
                100                 105                 110        Leu

His Leu Gln Met Gly Asn Lys Asp Asp Tyr Lys Leu Thr Cys Glu Glu
            115                 120                 125

Leu Arg Gln Arg Met Leu Tyr Leu Tyr Glu Glu Cys Gly Asn Ser Phe
        130                 135                 140

Arg
145

<210> SEQ ID NO 57
<211> LENGTH: 100
<212> TYPE: PRT
<213> ORGANISM: Cicer arietinum

<400> SEQUENCE: 57

Ile Pro Thr Pro Ser Gln Ala Thr Ser Ser Asp Leu Ser Met Val Lys
1               5                   10                  15

Lys Leu Ile Arg Asn Ala Ser Glu Arg Asp Arg Lys Lys Ile Asn
            20                  25                  30

Thr Leu Tyr Ser Ser Leu Arg Ser Leu Leu Pro Val Ala Glu Gln Met
        35                  40                  45

Lys Lys Leu Ser Asn Pro Ala Thr Ile Ser Arg Val Leu Lys Tyr Ile
50                  55                  60

Arg Glu Leu Gln Lys Gln Val Glu Gly Leu Leu Thr Arg Lys Glu Ala
65                  70                  75                  80

Ile Leu Leu Lys Leu Ser Pro Glu Val Asp Glu Val Lys Ser Lys Glu
                85                  90                  95

Ser Glu Arg Lys
            100

<210> SEQ ID NO 58
<211> LENGTH: 167
<212> TYPE: PRT
<213> ORGANISM: Hordeum vulgare

<400> SEQUENCE: 58

Ser Asp Arg Arg Lys Gln Leu Asn Glu Gln Tyr Ser Ser Leu Arg Ser
1               5                   10                  15

Leu Leu Pro Asp Asp His Asn Lys Lys Met Ser Ile Pro Thr Thr
            20                  25                  30

Val Ser Arg Val Ile Lys Tyr Ile Pro Glu Leu Gln Lys Glu Val Asp
        35                  40                  45

Gly Leu Glu Lys Lys Glu Glu Leu Arg Arg Ala Ser Ser Glu Gln
50                  55                  60

Gly Val Leu Thr Met Arg Gln Asn Thr Ala Pro Val Val Ser Ala Thr
65                  70                  75                  80

Cys Leu Asp Asp Arg Glu Ile Met Val Gln Val Ser Leu Val Ser Thr
                85                  90                  95

Met Ala Ala Ala Leu Pro Met Ser Lys Cys Ile Lys Val Leu Glu Asn
                100                 105                 110

Glu Gly Leu Arg Leu Ile Asn Ser Ser Thr Ser Ala Phe Gln Asn Arg
            115                 120                 125

Thr Phe Tyr Ser Leu His Leu Gln Arg Thr Gln Arg Met Thr Ser Lys
        130                 135                 140
```

```
Glu Gly Gln Thr Phe Cys Asn Glu Leu Glu Asn Ala Val Lys Gln Lys
145                 150                 155                 160

Ala Gly Leu His Leu His His
                165

<210> SEQ ID NO 59
<211> LENGTH: 252
<212> TYPE: PRT
<213> ORGANISM: Hordeum vulgare

<400> SEQUENCE: 59

Met Gly His Gln Thr Gln Met Phe Asp Asp Pro Phe Ala Ser Ser Met
1               5                   10                  15

Ser Ser Leu Asp Ala Asp Ile Phe Ser Val Ala Gly Gly Leu His Pro
                20                  25                  30

Ser Gln Trp Pro Gly Leu Asp His Asp Val Ser Leu Ala Pro Ala Ala
            35                  40                  45

Asn Asn Gly Thr Ser Ser Gly Gly Tyr Gly Ser Pro Gly Gly Gly Asp
        50                  55                  60

Gly Ser Gly Ser His Arg Lys Ile Ser His Asn Ala Tyr Glu Arg Asp
65                  70                  75                  80

Arg Arg Lys Gln Leu Asn Glu Leu Tyr Ser Asp Leu Arg Ser Leu Leu
                85                  90                  95

Pro Asp Ser Asp His Thr Lys Lys Leu Ser Ile Pro Ile Thr Val Ser
            100                 105                 110

Arg Val Leu Lys Tyr Ile Pro Glu Leu Gln Lys Gln Val Asp Gly Leu
        115                 120                 125

Glu Lys Lys Lys Glu Glu Leu Thr Arg Ala Ser Cys Lys Pro Gly Val
130                 135                 140

Leu Thr Met Lys Glu Asn Thr Val Pro Ile Val Ser Ala Thr Cys Leu
145                 150                 155                 160

Asp Glu Arg Glu Ile Met Val Gln Val Ser Leu Val Ser Thr Met Ala
                165                 170                 175

Gly Ala Leu Pro Met Ser Lys Arg Ile Lys Val Leu Glu Asn Glu Gly
            180                 185                 190

Leu Arg Leu Ile Ser Ser Ser Thr Ser Ala Phe Gln Asn Arg Thr Phe
        195                 200                 205

Tyr Ser Leu His Leu Gln Arg Thr Gln Arg Thr Met Ser Lys Glu Cys
    210                 215                 220

Pro Ala Phe Cys Glu Glu Leu Glu Asn Ala Leu Thr Gln Lys Ala Gly
225                 230                 235                 240

Tyr Val Tyr Ile Thr Ser Arg Leu Tyr Val Ala Glu
                245                 250

<210> SEQ ID NO 60
<211> LENGTH: 246
<212> TYPE: PRT
<213> ORGANISM: Medicago truncatula

<400> SEQUENCE: 60

Met Leu Ala Ile Ser Pro Pro Met Phe Ser Thr Ile Gly Trp Pro Phe
1               5                   10                  15

Glu Glu Pro Leu Ser His Asn Gln His Gln Asn Ser Phe Tyr Lys Asp
                20                  25                  30

Thr Val Asp Gln Leu Phe Asn Phe His Asp Gln Val Glu Ala Glu Ile
            35                  40                  45
```

```
Asn Ser Thr Asp Pro Ser Gln Ser Thr Ser Ser Asp Leu Ser Met Val
 50                  55                  60
Lys Lys Leu Val His Asn Ala Ser Glu Arg Asp Arg Arg Lys Lys Ile
 65                      70                  75                  80
Asn Asn Leu Tyr Ser Ser Leu Arg Ser Leu Pro Val Ser Asp Gln
             85                  90                  95
Met Lys Leu Ser Ile Pro Gly Thr Ile Ser Arg Val Leu Lys Tyr Ile
             100                 105                 110
Pro Glu Leu Gln Asn Gln Val Glu Gly Leu Ile Lys Arg Lys Asp Glu
             115                 120                 125
Ile Leu Leu Gly Leu Ser Pro Gln Val Glu Glu Phe Ile Leu Ser Lys
 130                 135                 140
Glu Ser Gln Arg Lys Lys His Ser Tyr Asn Ser Gly Phe Val Val Ser
 145                 150                 155                 160
Ser Ser Arg Leu Asn Asp Ser Glu Ile Thr Ile Gln Ile Ser Cys Tyr
             165                 170                 175
Thr Val Gln Lys Ile Pro Leu Ser Glu Ile Leu Ile Cys Leu Glu Asn
             180                 185                 190
Asp Gly Leu Leu Leu Leu Asn Val Ser Ser Ser Lys Thr Phe Gly Gly
             195                 200                 205
Arg Val Phe Tyr Asn Leu His Phe Gln Val Asp Lys Thr Gln Ile Leu
             210                 215                 220
Glu Ser His Ile Leu Asn Glu Lys Leu Leu Ser Ile Met Glu Lys Glu
 225                 230                 235                 240
Gly Glu Phe Leu Lys Gln
             245

<210> SEQ ID NO 61
<211> LENGTH: 260
<212> TYPE: PRT
<213> ORGANISM: Medicago truncatula

<400> SEQUENCE: 61

Met Val Ala Phe Cys Pro Pro Gln Phe Ser Tyr Ser Asn Met Gly Trp
 1               5                   10                  15
Leu Leu Glu Glu Leu Glu Pro Glu Ser Leu Ile Ser His Lys Glu Lys
                 20                  25                  30
Asn Tyr Ala Ser Leu Glu Tyr Ser Leu Pro Tyr His Gln Phe Ser Ser
             35                  40                  45
Pro Lys Glu His Val Glu Ile Glu Arg Pro Ser Pro Lys Leu Met
 50                  55                  60
Ala Lys Lys Leu Asn His Asn Ala Ser Glu Arg Asp Arg Arg Lys Lys
 65                  70                  75                  80
Ile Asn Ser Leu Ile Ser Ser Leu Arg Ser Leu Leu Pro Gly Glu Asp
             85                  90                  95
Gln Thr Lys Lys Met Ser Ile Pro Val Thr Ile Ser Arg Val Leu Lys
             100                 105                 110
Tyr Ile Pro Asp Leu Gln Lys Gln Val Gln Gly Leu Thr Lys Lys Lys
             115                 120                 125
Glu Glu Leu Leu Ser Arg Ile Ser His Arg Gln Glu Tyr Ala Val Asn
 130                 135                 140
Lys Glu Ser Gln Arg Lys Lys Ile Pro Asn Tyr Asn Ser Ala Phe Val
 145                 150                 155                 160
Val Ser Thr Ser Arg Leu Asn Asp Thr Glu Leu Val Ile His Ile Ser
             165                 170                 175
```

```
Ser Tyr Glu Ala Asn Lys Ile Pro Leu Ser Glu Ile Leu Met Cys Leu
            180                 185                 190

Glu Asn Asn Gly Leu Leu Leu Asn Ser Ser Ser Lys Thr Phe
        195                 200                 205

Gly Gly Arg Leu Phe Tyr Asn Leu His Phe Gln Val Asp Lys Thr Gln
        210                 215                 220

Arg Tyr Glu Cys Asp Asp Leu Ile Gln Lys Leu Ser Ser Ile Tyr Glu
225                 230                 235                 240

Lys Gln Gln Asn Asn His Leu Gly Thr Met Asp Gln Thr Ile Asn Ser
                245                 250                 255

Gly Leu Ile Tyr
            260

<210> SEQ ID NO 62
<211> LENGTH: 100
<212> TYPE: PRT
<213> ORGANISM: Medicago truncatula

<400> SEQUENCE: 62

Met Leu Ala Ile Ser Pro Pro Met Phe Ser Thr Ile Gly Trp Pro Phe
1               5                   10                  15

Glu Glu Pro Leu Ser His Asn Gln His Gln Asn Ser Phe Tyr Lys Asp
            20                  25                  30

Thr Val Asp Gln Leu Phe Asn Phe His Asp Gln Val Glu Ala Glu Ile
        35                  40                  45

Asn Ser Thr Asp Pro Ser Gln Ser Thr Ser Ser Asp Leu Ser Met Val
    50                  55                  60

Lys Lys Leu Val His Tyr Ala Ser Glu Arg Asp Arg Arg Lys Lys Ile
65                  70                  75                  80

Asn Asn Leu Tyr Ser Ser Leu Arg Ser Leu Leu Pro Val Ser Asp Gln
                85                  90                  95

Met Val Leu Asn
            100

<210> SEQ ID NO 63
<211> LENGTH: 247
<212> TYPE: PRT
<213> ORGANISM: Oryza sativa

<400> SEQUENCE: 63

Met Glu Gln Leu Phe Val Asp Asp Pro Ala Phe Ala Ser Ser Met Ser
1               5                   10                  15

Ser Leu Glu Ala Asp Ile Phe Ser Gly Ala Gly Gln Leu Pro Ser Ser
            20                  25                  30

Pro Trp Leu Asp Leu Asp Leu Asp Asp Val Gln Asp Leu Ser Met
        35                  40                  45

Ala Pro Thr Thr Ala Asn Ala Val Ser Ser Gly Tyr Gly Ser Gly Gly
    50                  55                  60

Ser Gly Ser His Arg Lys Leu Ser His Asn Ala Tyr Glu Arg Asp Arg
65                  70                  75                  80

Arg Lys Gln Leu Asn Glu Leu Tyr Ser Ser Leu Arg Ala Leu Leu Pro
                85                  90                  95

Asp Ala Asp His Thr Lys Leu Ser Ile Pro Thr Thr Val Ser Arg Val
            100                 105                 110

Leu Lys Tyr Ile Pro Glu Leu Gln Lys Gln Val Glu Asn Leu Glu Arg
        115                 120                 125
```

```
Lys Lys Lys Glu Leu Thr Thr Thr Ser Thr Thr Asn Cys Lys Pro Gly
    130                 135                 140
Val Leu Gly Ser Gln Leu Met Ser Gly Met Ala Pro Ile Val Ser
145                 150                 155                 160
Ala Thr Cys Ile Asn Asp Met Glu Ile Met Val Gln Val Ser Leu Leu
                165                 170                 175
Ser Asn Val Ala Gly Ser Val Leu Pro Leu Ser Lys Cys Ile Lys Val
                180                 185                 190
Leu Glu Asn Glu Gly Leu His Phe Ile Ser Ser Ser Thr Ser Ser Gly
                195                 200                 205
Phe Gly Asn Arg Thr Phe Tyr Ser Ile His Leu Gln Arg Ser Glu Gly
210                 215                 220
Thr Ile Asn Glu Glu Cys Pro Ala Phe Cys Glu Arg Leu Glu Lys Val
225                 230                 235                 240
Val Arg Asn Lys Ala Lys Leu
                245
```

<210> SEQ ID NO 64
<211> LENGTH: 230
<212> TYPE: PRT
<213> ORGANISM: Panicum virgatum

<400> SEQUENCE: 64

```
Met Glu His Gln Leu Phe Asp Asp Pro Phe Ser Ser Ser Ile Ser Ser
1               5                   10                  15
Leu Glu Ala Asp Ile Phe Ser Ala Gly Gly Gln Leu Pro Ser Pro Pro
                20                  25                  30
Trp Pro Asp Leu Asp Leu Asp Leu Asp Asp Asp Ile His Asp Leu
            35                  40                  45
Ser Ala Pro Thr Gly Asn Pro Thr Ser Ser Gly Gly Tyr Gly Ser Gly
50                  55                  60
Gly Gly Ser Gly Gly Ser His Arg Lys His Ser His Asn Ala Tyr Glu
65                  70                  75                  80
Arg Asp Arg Arg Lys Gln Leu Asn Glu Leu Tyr Ser Ser Leu Arg Ser
                85                  90                  95
Leu Leu Pro Asp Ala Asp His Thr Lys Lys Leu Ser Ile Pro Thr Thr
                100                 105                 110
Val Ser Arg Val Leu Lys Tyr Ile Pro Glu Leu Gln Lys Gln Val Asp
                115                 120                 125
Asn Leu Glu Arg Arg Lys Lys Glu Leu Thr Asn Ala Asn Cys Lys Pro
130                 135                 140
Gly Val Leu Asn Thr Ser Gln Ile Val Thr Pro Ile Val Ser Ala Thr
145                 150                 155                 160
Cys Leu Asn Asp Thr Glu Ile Met Val Gln Val Ser Leu His Ser Asn
                165                 170                 175
Val Ala Ala Thr Ser Leu Pro Leu Ser Lys Cys Ile Lys Val Met Glu
                180                 185                 190
Asn Glu Gly Leu His Leu Ile Ser Ser Ser Thr Tyr Ser Thr Phe Asp
                195                 200                 205
Asn Arg Thr Phe Tyr Ser Leu His Val Gln Arg Ser Gln Arg Thr Met
        210                 215                 220
Lys Glu Glu Cys Pro Ala
225                 230
```

```
<210> SEQ ID NO 65
<211> LENGTH: 183
<212> TYPE: PRT
<213> ORGANISM: Populus

<400> SEQUENCE: 65

Met Val Lys Lys Leu Ser His Asn Ala Asn Glu Arg Asp Arg Arg Lys
1               5                   10                  15

Lys Ile Lys Ser Leu Tyr Ser Ser Leu Arg Ser Leu Leu Pro Ala Ala
            20                  25                  30

Asp Gln Met Lys Lys Leu Ser Val Pro Ala Thr Val Ser Arg Ala Leu
        35                  40                  45

Lys Tyr Leu Pro Glu Leu Gln Gln Gln Val Glu Arg Leu Val Gln Arg
    50                  55                  60

Lys Glu Glu Leu Leu Ser Lys Leu Ser Lys Gln Gly Gly Ile Ile His
65                  70                  75                  80

Gln Glu Asn Gln Arg Asn Asp Thr Val Tyr Ser Ser Leu Ser Ser Val
                85                  90                  95

Ser Ala Ser Gln Leu Ser Asp Arg Glu Val Val His Ile Ser Thr
            100                 105                 110

Tyr Lys Asn His Lys Ser Pro Leu Ser Glu Ile Leu Leu Thr Leu Glu
        115                 120                 125

Glu Asp Gly Leu Val Leu Lys Asn Ser Ser Phe Glu Ser Phe Gly
    130                 135                 140

Asp Arg Val Phe Tyr Asn Leu His Leu Gln Val Met Glu Gly Thr Tyr
145                 150                 155                 160

Thr Leu Asp Ser Glu Ala Met Arg Ala Lys Leu Val Ser Leu Ser Val
                165                 170                 175

Lys Arg Glu Ser Ser Ser Leu
            180

<210> SEQ ID NO 66
<211> LENGTH: 264
<212> TYPE: PRT
<213> ORGANISM: Populus

<400> SEQUENCE: 66

Met Leu Glu Glu Leu Ser Pro Ile Ser Leu Phe Ser Thr Phe Gly Trp
1               5                   10                  15

Pro Leu Glu Glu Ala Ile Ser His Glu Gln His Tyr Ser Phe Arg Asp
            20                  25                  30

Gly Glu Thr Pro Glu Ser Phe Thr His Phe Pro Pro Ser Gln Pro Asp
        35                  40                  45

Val Arg Gln Leu Asp Arg Ser Thr Ser Phe Thr Ala His Ser Gly Ser
    50                  55                  60

Gly Asp Pro Ser Met Ala Lys Lys Leu Asn His Asn Ala Ser Glu Arg
65                  70                  75                  80

Asp Arg Arg Lys Lys Ile Asn Ser Leu Tyr Ser Ser Leu Arg Ser Leu
                85                  90                  95

Leu Pro Ala Ala Asp Gln Arg Lys Lys Leu Ser Ile Pro Tyr Thr Val
            100                 105                 110

Ser Arg Val Leu Val Tyr Ile Pro Lys Leu Gln Gln Gln Val Glu Arg
        115                 120                 125

Leu Ile Gln Arg Lys Glu Glu Leu Leu Ser Lys Leu Ser Arg Gln Ala
    130                 135                 140
```

```
Asp Asp Leu Thr His Gln Glu Asn Gln Arg Lys Gly Thr Met Tyr Ser
145                 150                 155                 160

Ser Leu Ser Ser Val Ser Ala Ser Arg Leu Ser Asp Arg Glu Val Val
                165                 170                 175

Ile His Ile Ser Thr Asn Lys Leu His Arg Ser Ser Leu Ser Glu Ile
            180                 185                 190

Leu Val Asn Leu Glu Glu Ala Gly Leu Leu Leu Asn Ser Ser Ser
        195                 200                 205

Phe Glu Ser Phe Gly Gly Arg Val Phe Tyr Asn Leu His Leu Gln Ala
    210                 215                 220

Met Glu Gly Thr Tyr Thr Val Glu Cys Glu Ala Leu Asn Glu Arg Leu
225                 230                 235                 240

Val Ser Leu Cys Glu Lys Arg Glu Ser Leu Phe Pro Leu Asn Ser Ser
                245                 250                 255

Ser Pro Tyr Ser Asn Cys Val Phe
                260

<210> SEQ ID NO 67
<211> LENGTH: 158
<212> TYPE: PRT
<213> ORGANISM: Populus

<400> SEQUENCE: 67

Asp Pro Asn Met Val Lys Lys Leu Asn His Asn Ala Ser Glu Arg Asp
1               5                   10                  15

Arg Arg Lys Lys Ile Asn Ser Leu Tyr Ser Ser Leu Arg Ser Leu Leu
                20                  25                  30

Pro Ala Ser Asp Gly Met Lys Lys Leu Ser Ile Pro Ser Thr Ile Ser
            35                  40                  45

Arg Val Leu Lys Tyr Ile Pro Glu Leu Gln Gln Val Glu Arg Gln
50                  55                  60

Ile Gln Arg Lys Glu Glu Leu Leu Ser Asn Leu Ser Arg Gln Asp Asp
65                  70                  75                  80

Leu Ile His Gln Glu Asn Gln Arg Lys Asp Thr Met Tyr Ser Ser Leu
                85                  90                  95

Ser Ser Val Ser Ala Ser Arg Leu Gly Asp Arg Glu Val Val Val Gln
                100                 105                 110

Ile Ser Thr Cys Lys Val Leu Lys Ser Pro Ile Ser Glu Ile Leu Leu
            115                 120                 125

Asn Leu Glu Glu Asn Gly Leu Val Leu Ile Asn Ser Ser Phe Glu
        130                 135                 140

Ser Phe Gly Gly Asn Val Phe Tyr His Leu His Leu Gln Val
145                 150                 155

<210> SEQ ID NO 68
<211> LENGTH: 257
<212> TYPE: PRT
<213> ORGANISM: Ricinus communis

<400> SEQUENCE: 68

Met Leu Ala Leu Ser Pro Val Phe Pro Thr Pro Glu Trp Pro Leu
1               5                   10                  15

Glu Asp Pro Leu Gly Ile Asp Gln Ile Ser Tyr Phe Cys Arg Glu Thr
                20                  25                  30

Gln Pro Ala Thr Ala Ala Phe Leu Pro Ser Tyr Gln Leu Glu Leu Leu
            35                  40                  45
```

```
Leu Leu Glu Leu Asp His Gln Gln Ser Thr Ser Phe Thr Ala Tyr Asn
 50                  55                  60

Ser Ser Gly Gly Asp Ala Asn Asp Met Val Lys Lys Leu Asn His Asn
 65                  70                  75                  80

Ala Ser Glu Arg Asp Arg Arg Lys Met Asn Thr Leu Tyr Ser Ser
                 85                  90                  95

Leu Arg Ser Leu Phe Pro Ala Ala Asp Glu Met Lys Lys Leu Ser Ile
                100                 105                 110

Pro Ala Thr Ile Ser Arg Val Leu Lys Tyr Ile Pro Glu Leu Gln Glu
                115                 120                 125

Gln Leu Glu Arg Leu Val Gln Arg Lys Glu Glu Ile Leu Leu Arg Ile
130                 135                 140

Ser Lys Gln Asn His Ile Val Asn Pro Gln Ile Asn Gln Arg Lys Gly
145                 150                 155                 160

Thr Ser His Ser Ser Leu Ser Val Val Ser Ala Asn Gln Ile Ser Asp
                165                 170                 175

Lys Glu Ala Ile Ile Gln Ile Ser Thr Tyr Ser Asn Thr Ile His Thr
                180                 185                 190

Ser Pro Leu Ser Glu Ile Leu Leu Leu Glu Glu Glu Gly Leu Leu
                195                 200                 205

Leu Ile Asn Ser Ser Ser Ala Glu Ser Phe Gly Gly Arg Val Phe Asn
210                 215                 220

Asn Leu His Val Gln Val Asp Asp Thr Tyr Thr Leu Glu Cys Asp Ala
225                 230                 235                 240

Leu Ser Glu Lys Leu Ala Ser Leu Tyr Ala Lys Arg Asp Gly Leu Phe
                245                 250                 255

Pro

<210> SEQ ID NO 69
<211> LENGTH: 184
<212> TYPE: PRT
<213> ORGANISM: Ricinus communis

<400> SEQUENCE: 69

Met Val Lys Lys Leu Asn His Asn Ala Ser Glu Arg Asp Arg Arg Lys
 1               5                  10                  15

Lys Met Asn Thr Leu Tyr Ser Ser Leu Arg Ser Leu Leu Pro Ala Ser
                20                  25                  30

Asp Gln Met Lys Lys Leu Ser Ile Pro Ala Thr Ile Ser Arg Val Leu
                35                  40                  45

Lys Tyr Ile Pro Glu Leu Gln Gln Gln Leu Glu Arg Phe Val Gln Arg
 50                  55                  60

Lys Glu Glu Leu Leu Leu Arg Ile Ser Lys Gln Asn His Ile Ile Asn
 65                  70                  75                  80

Pro Gln Ile Asn Gln Arg Lys Gly Thr Thr His Ser Thr Leu Ser Val
                85                  90                  95

Val Ser Ala Asn Gln Ile Ser Asp Lys Glu Val Val Ile Gln Val Ser
                100                 105                 110

Thr Tyr Asn Asn Thr Ile His Thr Ser Pro Leu Ser Glu Ile Leu Leu
                115                 120                 125

Leu Leu Glu Glu Glu Gly Leu Leu Leu Ile Asn Ser Ser Ser Phe Glu
130                 135                 140

Ser Phe Gly Gly Arg Val Phe Tyr Asn Leu His Leu Gln Val Asp Gly
145                 150                 155                 160
```

Thr Tyr Ile Leu Glu Cys Asp Ala Leu Ser Glu Lys Leu Ala Ala Leu
            165                 170                 175

Tyr Glu Arg Asp Gly Leu Phe Pro
            180

<210> SEQ ID NO 70
<211> LENGTH: 239
<212> TYPE: PRT
<213> ORGANISM: Solanum lycopersicum

<400> SEQUENCE: 70

Thr Thr Ile Ile Thr Thr Pro Gln Phe Gln Thr Asp Gln Asn Asn Lys
1               5                   10                  15

Leu Phe Glu Gly Leu Arg Ala Asp Asn Thr Ile Asp Leu Pro Ser Ser
                20                  25                  30

His His Tyr Gln Gln Gln Cys Leu Lys Gly Ser Glu Phe Asp Val Asp
            35                  40                  45

Glu Leu Gly Val Glu Arg Ser Leu Met Glu Lys Lys Leu Asn His Asn
        50                  55                  60

Ala Ser Glu Arg Asn Arg Arg Lys Lys Met Asn Phe Leu Tyr Ser Thr
65                  70                  75                  80

Leu Arg Ser Leu Leu Pro Pro Thr Asn Lys His Gln Lys Lys Lys
                85                  90                  95

Leu Ser Phe Pro Ala Thr Val Ser Tyr Val Gln Glu Tyr Ile Pro Glu
                100                 105                 110

Leu Lys Lys Glu Ile Glu Arg Leu Ser Lys Thr Lys Asp Leu Leu Leu
            115                 120                 125

Ser Lys Lys Ser Asn Tyr Ser Leu Leu Lys Ile Asp Asp Asn Asn Lys
        130                 135                 140

Arg Lys Leu Ile Ile Gly Gly Thr Ser Cys Asn Ser Thr Thr Ser
145                 150                 155                 160

Ile Cys Ala Ser Gln Leu Ser Asn Ser Gln Val Leu Val Gln Ile Ser
                165                 170                 175

Thr Thr Gln Glu Asn Asn Phe Pro Ile Ser Gln Val Phe Ala Ser Val
            180                 185                 190

Glu Glu Asp Gly Leu Ile Leu Leu Asn Ala Ser Ser Phe Lys Ser Phe
        195                 200                 205

Gly Asp Lys Ile Phe His Ser Leu His Phe Gln Met Gln Gly Pro Ile
    210                 215                 220

Glu Met Asp Ile Gln Val Leu Lys Thr Lys Leu Leu Val Met Cys
225                 230                 235

<210> SEQ ID NO 71
<211> LENGTH: 214
<212> TYPE: PRT
<213> ORGANISM: Sorghum bicolor

<400> SEQUENCE: 71

Met Asp His Gln Leu Phe Asp Asp Pro Phe Gly Ser Ser Ile Ser Ser
1               5                   10                  15

Leu Glu Ala Asp Ile Phe Ser Ala Gly Gly Gly Gln Leu Pro Ser
                20                  25                  30

Pro Pro Trp Pro Asp Leu Asp Leu Asp Asp Tyr Asp Ile His Asp
            35                  40                  45

Leu Ser Ala Pro Ala Ala Asn Ala Ala Thr Ser Ser Gly Gly Gly Tyr
        50                  55                  60

```
Gly Ser Gly Gly Ser Gly Arg Lys Leu Ser His Asn Ala Tyr Glu Arg
 65                  70                  75                  80

Asp Arg Arg Lys Gln Leu Asn Glu Leu Tyr Ser Ser Leu Arg Ser Leu
                 85                  90                  95

Leu Pro Asp Ala Asp His Thr Lys Lys Leu Ser Ile Pro Thr Thr Val
            100                 105                 110

Ser Arg Val Leu Asn Thr Lys Glu Ile Val Thr Pro Ile Val Ser Ala
        115                 120                 125

Thr Cys Leu Asn Asp Thr Glu Ile Met Val Gln Val Ser Leu His Ser
    130                 135                 140

Asn Val Ala Ala Thr Ala Leu Pro Leu Ser Lys Cys Ile Lys Val Leu
145                 150                 155                 160

Glu Asn Glu Gly Leu Leu Leu Val Ser Ser Thr Tyr Ser Thr Phe
                165                 170                 175

Glu Asn Lys Thr Phe Tyr Ser Leu His Leu Gln Arg Ser Gln Arg Thr
            180                 185                 190

Met Lys Glu Gln Cys Pro Gly Phe Cys Asp Glu Leu Glu Lys Ile Val
        195                 200                 205

Arg Lys Lys Ala Gly Ala
    210

<210> SEQ ID NO 72
<211> LENGTH: 224
<212> TYPE: PRT
<213> ORGANISM: Triticum aestivum

<400> SEQUENCE: 72

Met Glu His Gln Leu Phe Asp Asp Ala Val Pro Ser Ser Met Ile Trp
  1               5                  10                  15

Pro Leu Glu Ala Glu Asn Gly Phe Thr Asp Glu Leu Pro Ser Leu Gln
                 20                  25                  30

Leu Pro Asp Val Asp Leu Asp Phe Asp Ile His Glu Phe Ser Ala Pro
             35                  40                  45

Ala Thr Ala Pro Ala Lys Ala Ala Ser Ser Gly Gly Ser Gly Leu Val
         50                  55                  60

Gly Ser Gly Ser Gly Ser His Lys Lys Leu Asn His Asn Ala Tyr Glu
 65                  70                  75                  80

Arg Asp Arg Arg Thr Gln Leu Asn Gln Leu Tyr Ser Thr Leu Arg Ser
                 85                  90                  95

Leu Ile Pro Asn Ala Asp His Thr Lys Lys Leu Ser Ile Pro Thr Thr
            100                 105                 110

Val Cys Gln Val Leu Asp Tyr Ile Pro Lys Leu Gln Lys Gln Val Glu
        115                 120                 125

Asp Leu Lys Lys Lys Gln Glu Leu Ser Thr Ala Lys Cys Arg Glu
    130                 135                 140

Arg Leu Gln Arg Val Lys Asp Asn Thr Cys Arg Ile Val Ser Ala Thr
145                 150                 155                 160

Pro Leu Asp Gly Asn Glu Ile Met Val Gln Val Ser Leu Leu Ser Asn
                165                 170                 175

Met Ala Ala Ser Leu Pro Leu Ser Lys Cys Ile Asn Val Phe Glu Asn
            180                 185                 190

Lys Gly Leu His Leu Ile Ser Ser Ser Thr Phe Ser Thr Glu Val Asn
        195                 200                 205

Arg Thr Phe Tyr Ser Phe His Phe Glu Val Arg Phe Tyr Met Arg Pro
    210                 215                 220
```

```
<210> SEQ ID NO 73
<211> LENGTH: 130
<212> TYPE: PRT
<213> ORGANISM: Triticum aestivum
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid

<400> SEQUENCE: 73

Gly Asp Gly Ser Gly Ser His Arg Lys Ile Ser His Asn Ala Tyr Glu
1               5                   10                  15

Arg Asp Arg Arg Lys Gln Leu Asn Glu Leu Tyr Ser Asp Leu Arg Ser
                20                  25                  30

Leu Leu Pro Asp Thr Asp His Thr Lys Lys Leu Ser Ile Pro Ile Thr
            35                  40                  45

Val Ser Arg Val Leu Lys Tyr Ile Pro Glu Leu Gln Lys Gln Trp Ala
    50                  55                  60

Xaa Arg Xaa Lys Glu Gly Gly Xaa Asp Ala Arg Gln Leu Gln Pro Gly
65                  70                  75                  80

Val Xaa Thr Met Lys Gly Asn Thr Val Arg Leu Phe Arg His Leu Pro
                85                  90                  95

Arg Arg Gln Gly Xaa Tyr Gly Pro Ser Gln Pro Gly Glu His Met Ala
            100                 105                 110

Gly Xaa Cys Pro Phe Gln Met His Gln Ser Ala Gly Lys Gln Xaa Leu
        115                 120                 125

Arg Ser
    130

<210> SEQ ID NO 74
<211> LENGTH: 153
<212> TYPE: PRT
<213> ORGANISM: Triticum aestivum

<400> SEQUENCE: 74

Met Glu Gln Leu Phe Val Asp Asp Pro Ala Phe Ala Ser Ser Met Ser
1               5                   10                  15

Ser Leu Glu Ala Asp Ile Phe Ser Gly Ala Gly Gln Leu Pro Ser Ser
                20                  25                  30
```

```
Pro Trp Leu Asp Leu Asp Leu Asp Asp Val Gln Asp Leu Ser Met
            35                  40                  45

Ala Pro Thr Thr Ala Asn Ala Val Ser Ser Gly Tyr Gly Ser Gly Gly
 50                  55                  60

Ser Gly Ser His Arg Lys Leu Ser His Asn Ala Tyr Glu Arg Asp Arg
 65                  70                  75                  80

Arg Lys Gln Leu Asn Glu Leu Tyr Ser Ser Leu Arg Ala Leu Leu Pro
                 85                  90                  95

Asp Ala Asp His Thr Lys Lys Leu Ser Ile Pro Thr Thr Val Ser Arg
                100                 105                 110

Val Leu Lys Tyr Ile Pro Glu Leu Gln Lys Gln Val Glu Asn Leu Glu
                115                 120                 125

Arg Lys Lys Lys Glu Leu Thr Thr Thr Ser Thr Thr Asn Cys Gln Pro
130                 135                 140

Arg Val Leu Gly Ser Gln Leu Met Ser
145                 150

<210> SEQ ID NO 75
<211> LENGTH: 244
<212> TYPE: PRT
<213> ORGANISM: Vigna unguiculata

<400> SEQUENCE: 75

Met Val Ala Leu Phe Ser Pro Pro Leu Phe Ser Thr Lys Gly Trp Leu
 1                5                  10                  15

Leu Glu Glu Glu Pro Phe Gly Tyr Asn Asn Thr His Asn Leu Ser Tyr
                 20                  25                  30

Lys Asp Asp Ala Ser Ser Gln Tyr Ser Phe Pro Tyr Gln Phe Tyr Ser
             35                  40                  45

Pro Gln Thr Gln Ile Glu Val Glu Ile Glu Arg Ser Thr Ala Pro Ser
 50                  55                  60

Ser Asp Pro Ala Met Val Lys Lys Leu Ser His Asn Ala Ser Glu Arg
 65                  70                  75                  80

Asp Arg Arg Lys Lys Val Asn Asn Leu Val Ser Ser Leu Arg Ser Leu
                 85                  90                  95

Leu Pro Met Ala Asp Gln Thr Lys Lys Met Ser Ile Pro Ala Thr Val
                100                 105                 110

Ser Arg Val Leu Lys Tyr Ile Pro Glu Leu Gln Gln Gln Val Gln Ala
                115                 120                 125

Leu Thr Lys Arg Lys Glu Glu Leu Leu Cys Arg Ile Ser Arg Gln Leu
130                 135                 140

Gln Gly Glu Ala Val Asn Lys Glu Ser Gln Arg Lys Ile Ser His His
145                 150                 155                 160

Asn Ser Ser Phe Val Val Ser Thr Thr Arg Leu Asn Asp Cys Glu Ala
                165                 170                 175

Val Val His Ile Ser Ser His Glu Thr His Lys Ala Pro Leu Ser Glu
                180                 185                 190

Ile Leu Gln Cys Leu Glu Asn Asp Gly Leu Phe Leu Leu His Ala Ser
                195                 200                 205

Ser Ser Glu Thr Phe Gly Gly Arg Phe Phe Tyr Asn Leu His Phe His
                210                 215                 220

Val Glu Lys Thr Asp Arg Leu Glu Thr Glu Ile Leu Thr Glu Lys Leu
225                 230                 235                 240

Leu Pro Ile Tyr
```

-continued

```
<210> SEQ ID NO 76
<211> LENGTH: 245
<212> TYPE: PRT
<213> ORGANISM: Vitis vinifera
<220> FEATURE:
<221> NAME/KEY: misc_feature
<222> LOCATION: (20)..(20)
<223> OTHER INFORMATION: Xaa can be any naturally occurring amino acid

<400> SEQUENCE: 76

Met Leu Ala Phe Ser Pro Pro Leu Phe Ser Thr Phe Gly Trp Pro Trp
 1               5                  10                  15

Glu Asp Pro Xaa Ser His Glu Gln Asn Tyr Ile Tyr Gln Glu Thr Glu
            20                  25                  30

Ala Ser Glu Ser Phe Leu His Leu Pro Ser Ser Glu Pro Gln Ala Glu
        35                  40                  45

Leu Asn Tyr Ser Thr Pro Ser Ala Ala Val Ser Gly Asn Pro Thr Met
    50                  55                  60

Val Lys Lys Leu Asn His Asn Ala Ser Glu Arg Asp Arg Arg Lys Lys
 65                  70                  75                  80

Ile Asn Ser Leu Tyr Ser Ser Leu Arg Ser Leu Leu Pro Ala Ala Asp
                85                  90                  95

Gln Ala Lys Lys Leu Ser Ile Pro Ser Thr Val Ser Arg Val Leu Lys
            100                 105                 110

Tyr Ile Pro Glu Leu Gln Lys Gln Val Glu Arg Leu Ile Gln Lys Lys
        115                 120                 125

Glu Glu Leu Leu Ser Lys Ile Ser Arg Gln Gly Asp Ile Ile His Gln
    130                 135                 140

Glu Lys Gln Arg Lys Ala Thr Leu Ala Ser Ser Leu Ser Ala Val Ser
145                 150                 155                 160

Ala Asn Arg Leu Ser Asp Arg Glu Ile Val Gln Ile Ser Thr Phe
                165                 170                 175

Lys Val His Glu Ser Pro Leu Ser Glu Val Leu Leu Asn Leu Glu Glu
            180                 185                 190

Asp Gly Leu Leu Val Ile Asn Ala Ser Ser Phe Glu Ser Phe Gly Gly
        195                 200                 205

Arg Val Phe Tyr Asn Leu His Leu Gln Val Glu Gly Thr His Arg Met
    210                 215                 220

Glu Cys Glu Val Leu Ser Glu Lys Leu Leu Ser Leu Cys Glu Lys Arg
225                 230                 235                 240

Arg Asp Ala Phe Pro
            245

<210> SEQ ID NO 77
<211> LENGTH: 520
<212> TYPE: PRT
<213> ORGANISM: Vitis vinifera

<400> SEQUENCE: 77

Met Leu Ala Phe Ser Pro Pro Leu Phe Pro Thr Leu Gly Trp Pro Leu
 1               5                  10                  15

Glu Asp Pro Ile Ser His Ala Gln Asn Tyr Ile Tyr Gly Glu Thr Glu
            20                  25                  30

Thr Ser Glu Ser Phe Leu His Leu Pro Ser Ser Gln Pro Gln Val Glu
        35                  40                  45

Leu Asn Cys Ser Thr Pro Tyr Ala Ala Val Ser Gly Asn Pro Thr Met
    50                  55                  60
```

```
Val Lys Lys Leu Asn His Asn Val Ser Val Arg Asp Arg Arg Lys Lys
 65                  70                  75                  80

Ile Asn Ser Leu Tyr Ser Ser Leu Arg Ser Leu Leu Pro Ser Ala Asp
                 85                  90                  95

Gln Val Lys Lys Leu Ser Ile Pro Ser Thr Val Ser Cys Val Leu Lys
            100                 105                 110

Tyr Ile Pro Glu Leu Gln Arg Gln Val Glu Arg Leu Ile Gln Lys Lys
        115                 120                 125

Glu Glu Phe Leu Ser Lys Ile Ser Arg Glu Gly Asp Leu Ile His Leu
    130                 135                 140

Glu Asn Gln Arg Asn Gly Thr Leu Gly Ser Ser Leu Ser Ala Val Ser
145                 150                 155                 160

Ala Arg Arg Leu Ser Asp Arg Glu Ile Val Gln Ile Ser Thr Phe
                165                 170                 175

Lys Val His Glu Ser Pro Leu Ser Glu Val Leu Leu Asn Leu Glu Glu
                180                 185                 190

Asp Gly Leu Leu Val Ile Asn Ala Ser Ser Phe Glu Ser Phe Gly Gly
            195                 200                 205

Arg Val Phe Tyr Asn Leu His Leu Gln Val Glu Gly Thr Gln Gly Met
        210                 215                 220

Glu Ser Thr Ala His Leu Glu Met Thr Arg Thr Leu Lys Asn Lys His
225                 230                 235                 240

Met Asn Ile Leu Val Ile His Met Asp Phe Pro Pro Phe Phe Leu Lys
                245                 250                 255

Met Phe Leu Ile Phe Thr Arg Val Phe Thr Asn His Ile Ser Thr Ser
                260                 265                 270

Tyr Gln Cys Tyr Val Gly Lys Leu Ile Ile Leu Leu Leu His Val
                275                 280                 285

Ile Lys Lys Glu Asn Phe Glu Thr Ser Lys His Gln Leu Ala Ser Ala
    290                 295                 300

Glu Pro Ile Ile Val Ala Gly Gln Ala Ala Lys Lys Leu Asp Asp Glu
305                 310                 315                 320

Leu Leu Leu Glu Thr Lys Met Lys Thr Glu Gly Met Gly Val Leu Glu
                325                 330                 335

Thr Pro Ile Leu Ile Lys Ala Lys Asn Gly Thr Lys Glu Met Val Glu
                340                 345                 350

Arg Ile Leu Asp Leu Tyr Pro Met Ala Ile His Asp Ile Asp Ser Asn
            355                 360                 365

Lys Lys Asn Ile Val Leu Leu Ala Val Glu Asn Arg His Pro His Val
    370                 375                 380

Tyr Glu Leu Phe Leu Lys Arg Asn Ile Val Lys Asp Ser Val Phe Gly
385                 390                 395                 400

Ala Val Asp Asn Lys Gly Asn Ser Ala Leu His Leu Ala Ala Met Phe
                405                 410                 415

Ala Asp Tyr Arg Pro Trp Val Thr Pro Gly Val Ala Leu Gln Met Gln
            420                 425                 430

Trp Glu Val Lys Trp Tyr Glu Tyr Val Lys Lys Ser Met Pro Pro Asn
        435                 440                 445

Phe Phe Arg Phe His Asn Asn Glu Asn Lys Ser Thr Lys Gln Ile Phe
    450                 455                 460

Thr Arg Glu His Arg Asp Leu Val Gln Lys Gly Gly Gln Trp Leu Asn
465                 470                 475                 480
```

Asn Thr Ala Thr Ser Cys Ser Leu Val Val Thr Leu Ile Ala Thr Val
                485                 490                 495

Ala Phe Ala Thr Ser Thr Ala Val Pro Gly Gly Thr Lys Glu Gly Thr
            500                 505                 510

Asp Ser Cys Pro Leu Asn Gly Pro
        515                 520

<210> SEQ ID NO 78
<211> LENGTH: 244
<212> TYPE: PRT
<213> ORGANISM: Vitis vinifera
<220> FEATURE:
<221> NAME/KEY: misc_feature
<222> LOCATION: (98)..(98)
<223> OTHER INFORMATION: Xaa can be any naturally occurring amino acid

<400> SEQUENCE: 78

Met Leu Ala Phe Ser Pro Pro Leu Phe Pro Thr Leu Gly Trp Pro Leu
1               5                   10                  15

Glu Asp Pro Ile Ser His Ala Gln Asn Tyr Ile Tyr Gly Glu Thr Glu
            20                  25                  30

Thr Ser Glu Ser Phe Leu His Leu Ser Ser Gln Pro Gln Val Glu
        35                  40                  45

Leu Asn Cys Ser Thr Pro Ser Ala Ala Val Ser Gly Asn Pro Thr Met
50                  55                  60

Val Lys Lys Leu Asn His Asn Ala Ser Glu Arg Asp Arg Arg Lys Lys
65                  70                  75                  80

Ile Asn Ser Leu Tyr Ser Ser Met Arg Ser Leu Leu Pro Ser Ala Asp
                85                  90                  95

Gln Xaa Lys Lys Leu Ser Ile Pro Ser Thr Val Ser Arg Val Leu Lys
            100                 105                 110

Tyr Ile Pro Glu Leu Gln Arg Gln Val Glu Arg Leu Ile Gln Lys Lys
        115                 120                 125

Glu Glu Phe Leu Ser Lys Ile Cys Arg Glu Gly Asp Pro Ile His Leu
    130                 135                 140

Glu Asn Gln Arg Asn Gly Thr Leu Gly Ser Ser Leu Ser Ala Val Ser
145                 150                 155                 160

Ala Arg Arg Leu Ser Asp Arg Glu Ile Val Val Gln Ile Ser Thr Phe
                165                 170                 175

Asn Val His Glu Ser Pro Leu Ser Glu Val Leu Leu Asn Leu Glu Glu
            180                 185                 190

Asp Gly Leu Leu Val Ile Asn Ala Ser Ser Phe Glu Ser Phe Gly Gly
        195                 200                 205

Arg Val Phe Tyr Asn Leu His Leu Gln Val Glu Gly Thr Gln Gly Met
    210                 215                 220

Glu Cys Glu Leu Leu Ser Glu Lys Leu Leu Ser Leu Cys Glu Arg Arg
225                 230                 235                 240

Glu Ala Phe Pro

<210> SEQ ID NO 79
<211> LENGTH: 723
<212> TYPE: DNA
<213> ORGANISM: Arabidopsis thaliana

<400> SEQUENCE: 79
atggagtatc catggctgca gtctcaagtt cattccttt cacctactct ccatttcct      60 tccttccttc atcctttaga tgattccaag agccataaca tcaatcttca tcatatgagt    120

```
cttagtcaca gcaataatac taacagtaac aataacaatt atcaagaaga agatcgagga      180
gcggtggttt tggagaagaa actgaatcac aacgcaagcg aacgagaccg ccgtagaaaa      240
cttaacgcct tgtactcttc acttcgtgct ctcttgcctc tttctgatca aaagaggaag      300
ctgagcattc ctatgacggt agcgagagta gtgaaataca taccagagca gaagcaagaa      360
cttcaacgtt tgtctcggag aaaagaagag ctcttgaaga ggatctcgag aaaaactcac      420
caagagcagc tgagaaacaa agcaatgatg gactcaatag attcttcttc ctctcaacgg      480
atcgcagcaa attggctcac tgacacagag attgctgtcc agattgctac gtcgaaatgg      540
acatctgttt cagacatgtt gcttaggtta aagaaaacg gcttaatgt cataagcgtc       600 tcttcttccg tttcttccac cgcaaggatc ttctacactc tacatcttca gatgagagga      660
gattgcaaag tgagactgga ggaactcatc aatggtatgc tcttgggatt acgccaatca      720
taa                                                                    723

<210> SEQ ID NO 80
<211> LENGTH: 546
<212> TYPE: DNA
<213> ORGANISM: Brassica oleracea

<400> SEQUENCE: 80
atgtgtgcct taacaccaat gtttccaagt aaccaacaag aatggtactc tacttcaaca      60
atggagtatc catggcttga ttccttctct cctactctcc cttcttctct ttatcccttct     120 ttcgaccaac tagatgaatt caagagctat aacatcaatc ttcttcctca tcatatgaat      180
cttgctgaca taaatggtac taacaatgat caagaagaac atcaaggatc ggttttggaa      240
aagaaactga atcacaacgc aagtgaacgc gaccgccgta gaaagctaaa cgccttatac      300
gcttcacttc gtgctctctt gcctccttct gatcaaaaga gaaagttgag cattccaaag      360
accatagcgg gagtggtgaa gtatatacca gagcagaagc aagaacttca acgtttgtct      420
aggaggaaag aagagcttat gaagagaatc tccaataaga cagagacttt gaatcatcaa      480
caagaacagc tgagaaatag agcattaatg atggagtcaa tagattcttc ttcacaaaag      540
atcgct                                                                 546

<210> SEQ ID NO 81
<211> LENGTH: 678
<212> TYPE: DNA
<213> ORGANISM: Brassica rapa

<400> SEQUENCE: 81
atggagtatc catggcttga ttccttctct cctactctcc cttcttctct ttatccttct      60
ttcgaccaac tagatgaatt caagaactat aacatcaatc ttcttcctca tcatatgaat      120
cttgccgaca taaatggtac taacaatacc agtaacaatg atcaagaaga acatcaagga     180
tcggttttgg aaaagaaact gaatcacaac gcaagtgaac gcgaccgccg tagaaagcta     240
aacgccttat acgcttcact tcgtgctctc ttgcctcctt ctgatcaaaa gtcggcgaat     300
cagagaaagt tgagcattcc aaagaccgta gcgggagtgg tgaagtatat accagagcag     360
aagcaagaac ttcaacgttt gtataggagg aaagaagagc ttatgaagag gatctccaat     420
aagatagaga ctttgaatca tcaacaagaa cagctgagaa atagagcatt aatgatggag    480
tcaatagatt cttcttcaca aaagatcgct gcaaattgga tcaccaacac agaaatagct    540
gtccagattg ctacatggaa atggacatct atctcagaca tgttgcttag gttagaagaa    600
```

```
aacgggctta atgtcataag cgtctcttct tcggtttctt ccaccgcaag gatcttctac    660
acactgcatc ttcagatg                                                  678

<210> SEQ ID NO 82
<211> LENGTH: 261
<212> TYPE: DNA
<213> ORGANISM: Oryza sativa

<400> SEQUENCE: 82
gctttctctt tcagctcgat cgatccacag ctcaacgagc tctactcctc cctccgcgct    60 ctcctcccg acgccgatca cactaagaag ctgagcatcc cgacgacggt gtctcgcgtg    120
ctcaagtaca tacccgagct gcagaagcag gtggagaatc tggagaggaa gaagaaggag    180
ctgacgacga cgagcaccac caactgcaaa ccaggagtgt tggggagcca gctgatgagc    240
gagggcatgg ctcccatcgt t                                              261

<210> SEQ ID NO 83
<211> LENGTH: 450
<212> TYPE: DNA
<213> ORGANISM: Oryza sativa

<400> SEQUENCE: 83
atggagcagc tgttcgtcga cgacccagcc ttcgcgagca gcatgtcgtc gcttgaggcg    60
gacatcttct ccggcgccgg ccagctgccg tcctcgccgt ggctggacct agacctcgac    120
gacgatgtcc aagacctctc catggcgccg acgacggcga acgcggtgtc ctccggctac    180
ggcttcggcg gatccggctc ccacaggaag ctcagccaca cgcctacga gcgcgaccgc    240 cggaagcagc tcaacgagct ctactcctcc ctccgcgctc tcctccccga cgccgatcac    300
actaagaaac tgagcatttc gacgaacgtg tcctgcgtgg ttcagtacat aaccgaacct    360
gcagaaacaa gtggagaata tggagaagaa aaaaagagc tgacgacgac gagcaccacc    420
aactgtcaac cccaagatgt gggtagaagc                                     450

<210> SEQ ID NO 84
<211> LENGTH: 240
<212> TYPE: PRT
<213> ORGANISM: Arabidopsis thaliana

<400> SEQUENCE: 84

Met Glu Tyr Pro Trp Leu Gln Ser Gln Val His Ser Phe Ser Pro Thr
1               5                   10                  15

Leu His Phe Pro Ser Phe Leu His Pro Leu Asp Asp Ser Lys Ser His
            20                  25                  30

Asn Ile Asn Leu His His Met Ser Leu Ser His Ser Asn Asn Thr Asn
        35                  40                  45

Ser Asn Asn Asn Tyr Gln Glu Glu Asp Arg Gly Ala Val Val Leu
    50                  55                  60

Glu Lys Lys Leu Asn His Asn Ala Ser Glu Arg Asp Arg Arg Lys
65                  70                  75                  80

Leu Asn Ala Leu Tyr Ser Ser Leu Arg Ala Leu Leu Pro Leu Ser Asp
                85                  90                  95

Gln Lys Arg Lys Leu Ser Ile Pro Met Thr Val Ala Arg Val Val Lys
            100                 105                 110

Tyr Ile Pro Glu Gln Lys Gln Glu Leu Gln Arg Leu Ser Arg Arg Lys
        115                 120                 125
```

Glu Glu Leu Leu Lys Arg Ile Ser Arg Lys Thr His Gln Glu Gln Leu
130                 135                 140

Arg Asn Lys Ala Met Met Asp Ser Ile Asp Ser Ser Ser Ser Gln Arg
145                 150                 155                 160

Ile Ala Ala Asn Trp Leu Thr Asp Thr Glu Ile Ala Val Gln Ile Ala
                165                 170                 175

Thr Ser Lys Trp Thr Ser Val Ser Asp Met Leu Leu Arg Leu Glu Glu
                180                 185                 190

Asn Gly Leu Asn Val Ile Ser Val Ser Ser Val Ser Ser Thr Ala
                195                 200                 205

Arg Ile Phe Tyr Thr Leu His Leu Gln Met Arg Gly Asp Cys Lys Val
        210                 215                 220

Arg Leu Glu Glu Leu Ile Asn Gly Met Leu Leu Gly Leu Arg Gln Ser
225                 230                 235                 240

<210> SEQ ID NO 85
<211> LENGTH: 182
<212> TYPE: PRT
<213> ORGANISM: Brassica oleracea

<400> SEQUENCE: 85

Met Cys Ala Leu Thr Pro Met Phe Pro Ser Asn Gln Gln Glu Trp Tyr
1               5                   10                  15

Ser Thr Ser Thr Met Glu Tyr Pro Trp Leu Asp Ser Phe Ser Pro Thr
                20                  25                  30

Leu Pro Ser Ser Leu Tyr Pro Ser Phe Asp Gln Leu Asp Glu Phe Lys
            35                  40                  45

Ser Tyr Asn Ile Asn Leu Leu Pro His His Met Asn Leu Ala Asp Ile
50                  55                  60

Asn Gly Thr Asn Asn Asp Gln Glu Glu His Gly Ser Val Leu Glu
65                  70                  75                  80

Lys Lys Leu Asn His Asn Ala Ser Glu Arg Asp Arg Arg Lys Leu
                85                  90                  95

Asn Ala Leu Tyr Ala Ser Leu Arg Ala Leu Leu Pro Pro Ser Asp Gln
                100                 105                 110

Lys Arg Lys Leu Ser Ile Pro Lys Thr Ile Ala Gly Val Val Lys Tyr
                115                 120                 125

Ile Pro Glu Gln Lys Gln Glu Leu Gln Arg Leu Ser Arg Arg Lys Glu
130                 135                 140

Glu Leu Met Lys Arg Ile Ser Asn Lys Thr Glu Thr Leu Asn His Gln
145                 150                 155                 160

Gln Glu Gln Leu Arg Asn Arg Ala Leu Met Met Glu Ser Ile Asp Ser
                165                 170                 175

Ser Ser Gln Lys Ile Ala
                180

<210> SEQ ID NO 86
<211> LENGTH: 226
<212> TYPE: PRT
<213> ORGANISM: Brassica rapa

<400> SEQUENCE: 86

Met Glu Tyr Pro Trp Leu Asp Ser Phe Ser Pro Thr Leu Pro Ser Ser
1               5                   10                  15

Leu Tyr Pro Ser Phe Asp Gln Leu Asp Glu Phe Lys Asn Tyr Asn Ile
                20                  25                  30

Asn Leu Leu Pro His His Met Asn Leu Ala Asp Ile Asn Gly Thr Asn
            35                  40                  45

Asn Thr Ser Asn Asp Gln Glu His Gln Gly Ser Val Leu Glu
 50                  55                  60

Lys Lys Leu Asn His Asn Ala Ser Glu Arg Asp Arg Arg Lys Leu
 65                  70                  75                  80

Asn Ala Leu Tyr Ala Ser Leu Arg Ala Leu Leu Pro Pro Ser Asp Gln
                85                  90                  95

Lys Ser Ala Asn Gln Arg Lys Leu Ser Ile Pro Lys Thr Val Ala Gly
                100                 105                 110

Val Val Lys Tyr Ile Pro Glu Gln Lys Gln Glu Leu Gln Arg Leu Tyr
            115                 120                 125

Arg Arg Lys Glu Glu Leu Met Lys Arg Ile Ser Asn Lys Ile Glu Thr
130                 135                 140

Leu Asn His Gln Gln Glu Gln Leu Arg Asn Arg Ala Leu Met Met Glu
145                 150                 155                 160

Ser Ile Asp Ser Ser Ser Gln Lys Ile Ala Ala Asn Trp Ile Thr Asn
                165                 170                 175

Thr Glu Ile Ala Val Gln Ile Ala Thr Trp Lys Trp Thr Ser Ile Ser
            180                 185                 190

Asp Met Leu Leu Arg Leu Glu Glu Asn Gly Leu Asn Val Ile Ser Val
            195                 200                 205

Ser Ser Ser Val Ser Ser Thr Ala Arg Ile Phe Tyr Thr Leu His Leu
                210                 215                 220

Gln Met
225

<210> SEQ ID NO 87
<211> LENGTH: 87
<212> TYPE: PRT
<213> ORGANISM: Oryza sativa

<400> SEQUENCE: 87

Ala Phe Ser Phe Ser Ser Ile Asp Pro Gln Leu Asn Glu Leu Tyr Ser
1               5                   10                  15

Ser Leu Arg Ala Leu Leu Pro Asp Ala Asp His Thr Lys Lys Leu Ser
            20                  25                  30

Ile Pro Thr Thr Val Ser Arg Val Leu Lys Tyr Ile Pro Glu Leu Gln
            35                  40                  45

Lys Gln Val Glu Asn Leu Glu Arg Lys Lys Glu Leu Thr Thr Thr
 50                  55                  60

Ser Thr Thr Asn Cys Lys Pro Gly Val Leu Gly Ser Gln Leu Met Ser
 65                  70                  75                  80

Glu Gly Met Ala Pro Ile Val
                85

<210> SEQ ID NO 88
<211> LENGTH: 150
<212> TYPE: PRT
<213> ORGANISM: Oryza sativa

<400> SEQUENCE: 88

Met Glu Gln Leu Phe Val Asp Asp Pro Ala Phe Ala Ser Ser Met Ser
1               5                   10                  15

Ser Leu Glu Ala Asp Ile Phe Ser Gly Ala Gly Gln Leu Pro Ser Ser
            20                  25                  30

| | | | | | | | | | | | | |
|---|---|---|---|---|---|---|---|---|---|---|---|---|
|Pro|Trp|Leu|Asp|Leu|Asp|Leu|Asp|Asp|Val|Gln|Asp|Leu|Ser|Met|
| |35| | | |40| | | |45| | | |

Ala Pro Thr Thr Ala Asn Ala Val Ser Ser Gly Tyr Gly Phe Gly Gly
        50                  55                  60

Ser Gly Ser His Arg Lys Leu Ser His Asn Ala Tyr Glu Arg Asp Arg
65              70                  75                  80

Arg Lys Gln Leu Asn Glu Leu Tyr Ser Ser Leu Arg Ala Leu Leu Pro
                85                  90                  95

Asp Ala Asp His Thr Lys Lys Leu Ser Ile Ser Thr Asn Val Ser Cys
                100                 105                 110

Val Val Gln Tyr Ile Thr Glu Pro Ala Glu Thr Ser Gly Leu Tyr Gly
            115                 120                 125

Glu Glu Lys Lys Glu Leu Thr Thr Thr Ser Thr Thr Asn Cys Gln Pro
        130                 135                 140

Gln Asp Val Gly Arg Ser
145             150

```
<210> SEQ ID NO 89
<211> LENGTH: 726
<212> TYPE: DNA
<213> ORGANISM: Arabidopsis thaliana

<400> SEQUENCE: 89
atgtgtgcac ttgtccctcc attatatccc aatttcggct ggccttgcgg agatcatagc    60
ttctatgaaa ccgacgacgt atccaacacg tttcttgatt ttccgttgcc ggacttgacg   120
gtgactcatg agaatgtgtc gtctgagaat aacagaacat tactagacaa tcccgtggtg   180
atgaagaagc ttaatcacaa cgcgagtgaa cgtgagcgtc gcaagaagat caacacaatg   240
ttctcatctc ttcgttcttg tcttcctccc accaatcaaa cgaagttaag tgtttcggca   300
acagtttcac aagcattgaa gtacatacca gagctgcaag agcaagttaa aaagctcatg   360
aagaagaaag aagagctctc gtttcaaatt tcgggtcaaa gagatctcgt ttacaccgac   420
caaaacagta agtcagagga aggggttaca agctatgcgt cgacagtttc ttcgactagg   480
ctcagtgaga ctgaagtgat ggtccaaatt tcatcgttac agactgaaaa atgttcgttt   540
gggaatgtct tgagtggtgt agaagaagat gggttggttc ttgtgggtgc ttcatcttca   600
aggtctcatg gagagcgact cttttactct atgcatcttc agataaaaaa tggccaggtg   660
aattccgaag aattaggtga tagattgttg tacttgtacg agaaatgtgg acactcgttt   720
acatga                                                              726

<210> SEQ ID NO 90
<211> LENGTH: 729
<212> TYPE: DNA
<213> ORGANISM: Arabidopsis thaliana

<400> SEQUENCE: 90
atgtgtgcac ttgtccctcc attatatccc aatttcggct ggccttgcgg agatcatagc    60
ttctatgaaa ccgacgacgt atccaacacg tttcttgatt ttccgttgcc ggacttgacg   120
gtgactcatg agaatgtgtc gtctgagaat aacagaacat tactagacaa tcccgtggtg   180
atgaagaagc ttaatcacaa cgcgagtgaa cgtgagcgtc gcaagaagat caacacaatg   240
ttctcatctc ttcgttcttg tcttcctccc accaatcaaa cgaagaagtt aagtgtttcg   300
gcaacagttt cacaagcatt gaagtacata ccagagctgc aagagcaagt taaaaagctc   360
atgaagaaga agaagagct ctcgtttcaa atttcgggtc aaagagatct cgtttacacc   420
```

```
gaccaaaaca gtaagtcaga ggaaggggtt acaagctatg cgtcgacagt ttcttcgact    480
aggctcagtg agactgaagt gatggtccaa atttcatcgt tacagactga aaaatgttcg    540
tttgggaatg tcttgagtgg tgtagaagaa gatgggttgg ttcttgtggg tgcttcatct    600
tcaaggtctc atggagagcg actcttttac tctatgcatc ttcagataaa aaatggccag    660
gtgaattccg aagaattagg tgatagattg ttgtacttgt acgagaaatg tggacactcg    720
tttacatga                                                            729

<210> SEQ ID NO 91
<211> LENGTH: 621
<212> TYPE: DNA
<213> ORGANISM: Oryza sativa

<400> SEQUENCE: 91
ccacgtcgtc tgcgcggccg actccttcta cgtcggcctc ccgatcccgg tggtgtccgc     60
cggcgaggag ctgatggcgg ggcgaacctc atccacaacg cctacgagcg cgaccgccgg    120
aagcagcgca acgagctcta ctcctccctc cgcgctctcc tccccgacgc cgatcacact    180
aagaagctga gcatcccgac gacggtgtct cgcgtgctca agtacatacc cgagctgcag    240
aagcaggtgg agaatctgga gaggaagaag aaggagctga cgacgacgag caccaccaac    300
tgcaaaccag gagtgttggg gagccagctg atgagcgagg gcatggctcc catcgtttcg    360
gctacctgca tcaatgacat ggagatcatg gttcaggtca gcttgttgag caatgtggcg    420
ggttcagttc ttcctctctc caagtgtatc aaagtactgg agaacgaagg tcttcacttc    480
atcagttcat cgacttcctc cggatttggg aacaggacat tctacagtat ccatcttcag    540
agaagtgaag gaacgatcaa cgaggagtgc ccagcatttt gtgaaaggtt ggagaaagtc    600
gtcaggaaca aagcaaagct t                                              621

<210> SEQ ID NO 92
<211> LENGTH: 711
<212> TYPE: DNA
<213> ORGANISM: Panicum virgatum

<400> SEQUENCE: 92
atggagcacc agctgttcga tgacccctto tctagcagca tctcgtcgct ggaggcggac     60
atcttctccg ccggcggcca gctgccgtcg ccgccgtggc cggacctcga cctcgacctc    120
gacgacgacg acggcatcca cgacctctcc gcgccggccg gcaacccccac ctcttcagga    180 ggctatggct cgggcggagg ctcccacagg aagatcagcc acaacgcgta cgagcgtgac    240
cgccggaagc agctcaacga gctctactcc tcgctccgct ccctcctccc cgacgctgac    300
cacactaaga agctgagcat ccccaccacg gtctcccgag ttctcaagta catccccgag    360
ctgcagaagc aggtggacaa cctggagagg aggaagaagg agctgacgaa cgccaactgc    420
aaaccaggag ttctgaacac gagccagatt gtaactccca ttgtttctgc tacttgcctc    480
aacgatacgg agatcatggt tcaggtcagc ctgcacagca acgtggctgc cacaagtctt    540
cctctgtcca agtgcataaa agtgatggag aacgaaggcc ttcacctaat tagttcatca    600
acttactcca ccttcgacaa caggacattc tatagcctcc atgttcagag aagtcaaaga    660
acgatgaagg aggagtgccc agcattctgc gatgaactgg agaggattat c              711

<210> SEQ ID NO 93
<211> LENGTH: 732
<212> TYPE: DNA
<213> ORGANISM: Sorghum bicolor
```

<400> SEQUENCE: 93

```
atggaccatc agctgttcga cgacccottc gggagcagca tctcgtcgct ggaggcggac      60
atcttctccg ccggcggcgg cggacagctg ccgtcgccgc cgtggccgga cctcgacctc     120
gacgacgact acgacataca cgacctctcc gcgccggccg ccaacgccgc cacctcctcg     180
ggcggcggct atggctccgg cggctccggc aggaagctca gccacaacgc atacgagcgc     240
gaccgccgga agcagctcaa cgagctctac tcctcgctcc gatccctcct cccggacgct     300
gatcacacta agaagctgag catccccacc accgtgtccc gagttctcaa gtacatcccg     360
gagctgcaga agcaggtgga taacctggag aggaggaaga aggagctgac caacgccaac     420
tgcaagccgg gagttctcaa caccaaagag atcgtaactc ccattgtttc tgctacttgc     480
cttaacgaca cggagatcat ggttcaggtc agcctgcaca gcaatgtggc cgccacagct     540
ctccctctct ccaagtgcat aaaggtgcta gaaaacgaag gcttctcct cgtcagctca     600
tcaacctact ccaccttcga gaacaagaca ttctatagcc tccatcttca gagaagtcaa     660
agaacgatga aggagcagtg cccaggattc tgcgacgaac tggagaagat cgtcaggaag     720
aaagcagggg cg                                                          732
```

<210> SEQ ID NO 94
<211> LENGTH: 417
<212> TYPE: DNA
<213> ORGANISM: Triticum aestivum

<400> SEQUENCE: 94

```
gcctcgtgcc ggcgggtgct caagtacatc ccggagctgc agaagcaggt ggacggactg      60
gagaagaaga aggaggagct gacgcgcgcc aactgcaagc ccggcgtgct gaccatgaag     120
gagaacatgg ctccgatcgt gtccgccacc tgcctcgatg acagagaaat catggtccag     180
gtcagcctgg tgagcaccat ggccggagtt ctgcccatgt ccaagtgcat caaggtgctg     240
gagaacgaag gcctacgcct catcagctcg tccacttccg cgtttcacaa caggacgttc     300
tatagcctcc atcttcagag aacccaacgg acgatgagca aggagtgtcc ggcatttgt     360
gaagaactgg agaacgccct gacgcaaaag gcaggactac gtctacatca ccaccag        417
```

<210> SEQ ID NO 95
<211> LENGTH: 705
<212> TYPE: DNA
<213> ORGANISM: Triticum aestivum

<400> SEQUENCE: 95

```
atggatcacc agctgtacgg cgaccoctcc gcgagcagct tctctccgct ggaggcacag      60
atcttctccg ccagctgcc gccgtcgtca acgccatggc caaatctcga cgttgacctc     120
gccctggacc tcgacgttct cgaggatgac atcgtccggg agctctctgc tggcacagtg     180
gcaaacgcgg catcgtcagg ttccggctcc ggcgcccaca agaagctcag ccacaacgcg     240
tacgagcgcg accgccggaa gcagctcaac gagctatacc tctcgctccg ttctctcctc     300
ccggacgcca accacaccaa gaagctgagt attccgacga cggtgtgtcg agcgctcaag     360
tacatccccg agctgcagaa acaggtcgag aatctggaga agaagaaaga gaaactggct     420
agtgccaact gcaaaccagg ggtactgagc gtgaccggca gcatagctcc aactgtgtcc     480
gctacttgcc tcaaccacaa ggaaatcatg gttcagatta gcttgctgag agatacagat     540
gcttctacag ctctacctct ttccaagtgt ataaatgtac tggagaacga aggacttcag     600
```

```
ctcatcagtt catcgacttc ctccacctttt gggaacaaaa cgttctataa cctccatctt    660
cagagaagtc aaggagccac taaacatgga gtgcccatcg ttttg                     705

<210> SEQ ID NO 96
<211> LENGTH: 691
<212> TYPE: DNA
<213> ORGANISM: Triticum aestivum

<400> SEQUENCE: 96
cgcagatctt ctccagccag ctgccgccgt caccgccgtg gccgaatctc gatgttgacg     60
ttgacctgga cctcgacgtt cttgaggacg acgtcgtccg cgaactctca gggaggccgg    120
caaacgcggc atcgtcaggc tccggctccg gcggccccgg ctcccacaag aagctcagtc    180
acaacgcgta cgagcgcgac cgccggaagc agctcaacga gctctacctc tcactccgtt    240
ctctcctgcc ggacgccgac cacactaaga agctgagtat tccgacgatg gtgtgtcgag    300
cgctcaagta catcccgagc tgcagaaaca ggtcgagaat ctggagaaga agaaagagaa    360
acttgctagt tccaactgca aaccagaggt actgagcgca agcggcagca tagctctaac    420
tgtgtccgct acttgcctca acgacaagga aatcatggtt cagattagct tgctgagaca    480 tacgatgct gctacagctc tacctctttc caagtgtata aatgtactgg agaacgaagg    540
acttgagctc gtcagttcat cgacttcctg caccttggg aacaaaatgt tctataacct    600
ccatcttcag agaagtcaag gagcgctaac atgggagtgt ccatccttct gtgacaaatt    660
ggaacaagca atcaggaaaa cagcaggatt a                                   691

<210> SEQ ID NO 97
<211> LENGTH: 465
<212> TYPE: DNA
<213> ORGANISM: Zea mays

<400> SEQUENCE: 97
cgacggaagc agctcaacga cctttactcc tcgctccgct ccctcctccc ggacgctgac     60
cacaccaaga agctgagcat ccccaccacc gtgtcccgag tcctcaagta catcccggag    120
ctgcagaagc aggtggacaa cctggagagg aggaagcggg agctgaccaa cgccaactgc    180
aagccgggag ttctcaacac cagcgagatc gtaactactc ccattgtttc tgctacttgc    240
ctcaacgaca cggagatcat ggttcaggtc agcctgcaca gcaatgtggc agccacggct    300
ctccctctct ccaagtgcat aaaggtgctg gaggacgcag gccttcacct catcagctca    360
tcaacctact ccacctttgg gaacaagaca ttctatagcc tccatcttca ggtgtgcatg    420
catgttcatt caatggttcc tgccgtttcc ttcaattttt ttatc                    465

<210> SEQ ID NO 98
<211> LENGTH: 241
<212> TYPE: PRT
<213> ORGANISM: Arabidopsis thaliana

<400> SEQUENCE: 98

Met Cys Ala Leu Val Pro Pro Leu Tyr Pro Asn Phe Gly Trp Pro Cys
 1               5                  10                  15

Gly Asp His Ser Phe Tyr Glu Thr Asp Asp Val Ser Asn Thr Phe Leu
                20                  25                  30

Asp Phe Pro Leu Pro Asp Leu Thr Val Thr His Glu Asn Val Ser Ser
            35                  40                  45

Glu Asn Asn Arg Thr Leu Leu Asp Asn Pro Val Val Met Lys Lys Leu
        50                  55                  60
```

```
Asn His Asn Ala Ser Glu Arg Glu Arg Lys Lys Ile Asn Thr Met
 65                  70                  75                  80

Phe Ser Ser Leu Arg Ser Cys Leu Pro Pro Thr Asn Gln Thr Lys Leu
             85                  90                  95

Ser Val Ser Ala Thr Val Ser Gln Ala Leu Lys Tyr Ile Pro Glu Leu
            100                 105                 110

Gln Glu Gln Val Lys Lys Leu Met Lys Lys Glu Glu Leu Ser Phe
        115                 120                 125

Gln Ile Ser Gly Gln Arg Asp Leu Val Tyr Thr Asp Gln Asn Ser Lys
    130                 135                 140

Ser Glu Glu Gly Val Thr Ser Tyr Ala Ser Thr Val Ser Ser Thr Arg
145                 150                 155                 160

Leu Ser Glu Thr Glu Val Met Val Gln Ile Ser Ser Leu Gln Thr Glu
                165                 170                 175

Lys Cys Ser Phe Gly Asn Val Leu Ser Gly Val Glu Glu Asp Gly Leu
            180                 185                 190

Val Leu Val Gly Ala Ser Ser Arg Ser His Gly Glu Arg Leu Phe
        195                 200                 205

Tyr Ser Met His Leu Gln Ile Lys Asn Gly Gln Val Asn Ser Glu Glu
210                 215                 220

Leu Gly Asp Arg Leu Leu Tyr Leu Tyr Glu Lys Cys Gly His Ser Phe
225                 230                 235                 240

Thr

<210> SEQ ID NO 99
<211> LENGTH: 242
<212> TYPE: PRT
<213> ORGANISM: Arabidopsis thaliana

<400> SEQUENCE: 99

Met Cys Ala Leu Val Pro Pro Leu Tyr Pro Asn Phe Gly Trp Pro Cys
 1               5                  10                  15

Gly Asp His Ser Phe Tyr Glu Thr Asp Asp Val Ser Asn Thr Phe Leu
                20                  25                  30

Asp Phe Pro Leu Pro Asp Leu Thr Val Thr His Glu Asn Val Ser Ser
            35                  40                  45

Glu Asn Asn Arg Thr Leu Leu Asp Asn Pro Val Val Met Lys Lys Leu
 50                  55                  60

Asn His Asn Ala Ser Glu Arg Glu Arg Lys Lys Ile Asn Thr Met
 65                  70                  75                  80

Phe Ser Ser Leu Arg Ser Cys Leu Pro Pro Thr Asn Gln Thr Lys Lys
             85                  90                  95

Leu Ser Val Ser Ala Thr Val Ser Gln Ala Leu Lys Tyr Ile Pro Glu
            100                 105                 110

Leu Gln Glu Gln Val Lys Lys Leu Met Lys Lys Glu Glu Leu Ser
        115                 120                 125

Phe Gln Ile Ser Gly Gln Arg Asp Leu Val Tyr Thr Asp Gln Asn Ser
    130                 135                 140

Lys Ser Glu Glu Gly Val Thr Ser Tyr Ala Ser Thr Val Ser Ser Thr
145                 150                 155                 160

Arg Leu Ser Glu Thr Glu Val Met Val Gln Ile Ser Ser Leu Gln Thr
                165                 170                 175

Glu Lys Cys Ser Phe Gly Asn Val Leu Ser Gly Val Glu Glu Asp Gly
            180                 185                 190
```

```
Leu Val Leu Val Gly Ala Ser Ser Arg Ser His Gly Glu Arg Leu
            195                 200                 205

Phe Tyr Ser Met His Leu Gln Ile Lys Asn Gly Gln Val Asn Ser Glu
    210                 215                 220

Glu Leu Gly Asp Arg Leu Leu Tyr Leu Tyr Glu Lys Cys Gly His Ser
225                 230                 235                 240

Phe Thr

<210> SEQ ID NO 100
<211> LENGTH: 207
<212> TYPE: PRT
<213> ORGANISM: Oryza sativa

<400> SEQUENCE: 100

Pro Arg Arg Leu Arg Gly Arg Leu Leu Arg Arg Pro Pro Asp Pro
1               5                   10                  15

Gly Gly Val Arg Arg Gly Ala Asp Gly Ala Asn Leu Ile His
            20                  25                  30

Asn Ala Tyr Glu Arg Asp Arg Lys Gln Arg Asn Glu Leu Tyr Ser
            35                  40                  45

Ser Leu Arg Ala Leu Leu Pro Asp Ala Asp His Thr Lys Lys Leu Ser
    50                  55                  60

Ile Pro Thr Thr Val Ser Arg Val Leu Lys Tyr Ile Pro Glu Leu Gln
65                  70                  75                  80

Lys Gln Val Glu Asn Leu Glu Arg Lys Lys Glu Leu Thr Thr Thr
                85                  90                  95

Ser Thr Thr Asn Cys Lys Pro Gly Val Leu Gly Ser Gln Leu Met Ser
                100                 105                 110

Glu Gly Met Ala Pro Ile Val Ser Ala Thr Cys Ile Asn Asp Met Glu
            115                 120                 125

Ile Met Val Gln Val Ser Leu Leu Ser Asn Val Ala Gly Ser Val Leu
    130                 135                 140

Pro Leu Ser Lys Cys Ile Lys Val Leu Glu Asn Glu Gly Leu His Phe
145                 150                 155                 160

Ile Ser Ser Ser Thr Ser Ser Gly Phe Gly Asn Arg Thr Phe Tyr Ser
                165                 170                 175

Ile His Leu Gln Arg Ser Glu Gly Thr Ile Asn Glu Glu Cys Pro Ala
            180                 185                 190

Phe Cys Glu Arg Leu Glu Lys Val Val Arg Asn Lys Ala Lys Leu
    195                 200                 205

<210> SEQ ID NO 101
<211> LENGTH: 237
<212> TYPE: PRT
<213> ORGANISM: Panicum virgatum

<400> SEQUENCE: 101

Met Glu His Gln Leu Phe Asp Asp Pro Phe Ser Ser Ile Ser Ser
1               5                   10                  15

Leu Glu Ala Asp Ile Phe Ser Ala Gly Gly Gln Leu Pro Ser Pro
            20                  25                  30

Trp Pro Asp Leu Asp Leu Asp Leu Asp Asp Asp Gly Ile His Asp
            35                  40                  45

Leu Ser Ala Pro Ala Gly Asn Pro Thr Ser Ser Gly Gly Tyr Gly Ser
    50                  55                  60
```

```
Gly Gly Gly Ser His Arg Lys Ile Ser His Asn Ala Tyr Glu Arg Asp
65                  70                  75                  80

Arg Arg Lys Gln Leu Asn Glu Leu Tyr Ser Ser Leu Arg Ser Leu Leu
                85                  90                  95

Pro Asp Ala Asp His Thr Lys Lys Leu Ser Ile Pro Thr Thr Val Ser
            100                 105                 110

Arg Val Leu Lys Tyr Ile Pro Glu Leu Gln Lys Gln Val Asp Asn Leu
        115                 120                 125

Glu Arg Arg Lys Lys Glu Leu Thr Asn Ala Asn Cys Lys Pro Gly Val
    130                 135                 140

Leu Asn Thr Ser Gln Ile Val Thr Pro Ile Val Ser Ala Thr Cys Leu
145                 150                 155                 160

Asn Asp Thr Glu Ile Met Val Gln Val Ser Leu His Ser Asn Val Ala
                165                 170                 175

Ala Thr Ser Leu Pro Leu Ser Lys Cys Ile Lys Val Met Glu Asn Glu
            180                 185                 190

Gly Leu His Leu Ile Ser Ser Thr Tyr Ser Thr Phe Asp Asn Arg
        195                 200                 205

Thr Phe Tyr Ser Leu His Val Gln Arg Ser Gln Arg Thr Met Lys Glu
210                 215                 220

Glu Cys Pro Ala Phe Cys Asp Glu Leu Glu Arg Ile Ile
225                 230                 235
```

<210> SEQ ID NO 102
<211> LENGTH: 244
<212> TYPE: PRT
<213> ORGANISM: Sorghum bicolor

<400> SEQUENCE: 102

```
Met Asp His Gln Leu Phe Asp Asp Pro Phe Gly Ser Ser Ile Ser Ser
1               5                   10                  15

Leu Glu Ala Asp Ile Phe Ser Ala Gly Gly Gly Gly Gln Leu Pro Ser
                20                  25                  30

Pro Pro Trp Pro Asp Leu Asp Leu Asp Asp Tyr Asp Ile His Asp
            35                  40                  45

Leu Ser Ala Pro Ala Ala Asn Ala Ala Thr Ser Ser Gly Gly Gly Tyr
50                  55                  60

Gly Ser Gly Gly Ser Gly Arg Lys Leu Ser His Asn Ala Tyr Glu Arg
65                  70                  75                  80

Asp Arg Arg Lys Gln Leu Asn Glu Leu Tyr Ser Ser Leu Arg Ser Leu
                85                  90                  95

Leu Pro Asp Ala Asp His Thr Lys Lys Leu Ser Ile Pro Thr Thr Val
            100                 105                 110

Ser Arg Val Leu Lys Tyr Ile Pro Glu Leu Gln Lys Gln Val Asp Asn
        115                 120                 125

Leu Glu Arg Arg Lys Lys Glu Leu Thr Asn Ala Asn Cys Lys Pro Gly
    130                 135                 140

Val Leu Asn Thr Lys Glu Ile Val Thr Pro Ile Val Ser Ala Thr Cys
145                 150                 155                 160

Leu Asn Asp Thr Glu Ile Met Val Gln Val Ser Leu His Ser Asn Val
                165                 170                 175

Ala Ala Thr Ala Leu Pro Leu Ser Lys Cys Ile Lys Val Leu Glu Asn
            180                 185                 190

Glu Gly Leu Leu Leu Val Ser Ser Ser Thr Tyr Ser Thr Phe Glu Asn
        195                 200                 205
```

```
Lys Thr Phe Tyr Ser Leu His Leu Gln Arg Ser Gln Arg Thr Met Lys
    210                 215                 220
Glu Gln Cys Pro Gly Phe Cys Asp Glu Leu Glu Lys Ile Val Arg Lys
225                 230                 235                 240
Lys Ala Gly Ala

<210> SEQ ID NO 103
<211> LENGTH: 139
<212> TYPE: PRT
<213> ORGANISM: Triticum aestivum

<400> SEQUENCE: 103

Ala Ser Cys Arg Arg Val Leu Lys Tyr Ile Pro Glu Leu Gln Lys Gln
1               5                   10                  15
Val Asp Gly Leu Glu Lys Lys Glu Leu Thr Arg Ala Asn Cys
            20                  25                  30
Lys Pro Gly Val Leu Thr Met Lys Glu Asn Met Ala Pro Ile Val Ser
            35                  40                  45
Ala Thr Cys Leu Asp Asp Arg Glu Ile Met Val Gln Val Ser Leu Val
        50                  55                  60
Ser Thr Met Ala Gly Val Leu Pro Met Ser Lys Cys Ile Lys Val Leu
65                  70                  75                  80
Glu Asn Glu Gly Leu Arg Leu Ile Ser Ser Thr Ser Ala Phe His
                85                  90                  95
Asn Arg Thr Phe Tyr Ser Leu His Leu Gln Arg Thr Gln Arg Thr Met
                100                 105                 110
Ser Lys Glu Cys Pro Ala Phe Cys Glu Glu Leu Glu Asn Ala Leu Thr
            115                 120                 125
Gln Lys Ala Gly Leu Arg Leu His His Gln
        130                 135

<210> SEQ ID NO 104
<211> LENGTH: 235
<212> TYPE: PRT
<213> ORGANISM: Triticum aestivum

<400> SEQUENCE: 104

Met Asp His Gln Leu Tyr Gly Asp Pro Ser Ala Ser Ser Phe Ser Pro
1               5                   10                  15
Leu Glu Ala Gln Ile Phe Ser Gly Gln Leu Pro Pro Ser Ser Thr Pro
            20                  25                  30
Trp Pro Asn Leu Asp Val Asp Leu Ala Leu Asp Leu Asp Val Leu Glu
            35                  40                  45
Asp Asp Ile Val Arg Glu Leu Ser Ala Gly Thr Val Ala Asn Ala Ala
        50                  55                  60
Ser Ser Gly Ser Gly Ser Gly Ala His Lys Lys Leu Ser His Asn Ala
65                  70                  75                  80
Tyr Glu Arg Asp Arg Arg Lys Gln Leu Asn Glu Leu Tyr Leu Ser Leu
                85                  90                  95
Arg Ser Leu Leu Pro Asp Ala Asp His Thr Lys Leu Ser Ile Pro
            100                 105                 110
Thr Thr Val Cys Arg Ala Leu Lys Tyr Ile Pro Glu Leu Gln Lys Gln
            115                 120                 125
Val Glu Asn Leu Glu Lys Lys Lys Glu Lys Leu Ala Ser Ala Asn Cys
        130                 135                 140
```

```
Lys Pro Gly Val Leu Ser Val Thr Gly Ser Ile Ala Pro Thr Val Ser
145                 150                 155                 160

Ala Thr Cys Leu Asn His Lys Glu Ile Met Val Gln Ile Ser Leu Leu
                165                 170                 175

Arg Asp Thr Asp Ala Ser Thr Ala Leu Pro Leu Ser Lys Cys Ile Asn
            180                 185                 190

Val Leu Glu Asn Glu Gly Leu Gln Leu Ile Ser Ser Thr Ser Ser Ser
        195                 200                 205

Thr Phe Gly Asn Lys Thr Phe Tyr Asn Leu His Leu Gln Arg Ser Gln
    210                 215                 220

Gly Ala Thr Lys His Gly Val Pro Ile Val Leu
225                 230                 235
```

<210> SEQ ID NO 105
<211> LENGTH: 155
<212> TYPE: PRT
<213> ORGANISM: Zea mays

<400> SEQUENCE: 105

```
Arg Arg Lys Gln Leu Asn Asp Leu Tyr Ser Ser Leu Arg Ser Leu Leu
1               5                   10                  15

Pro Asp Ala Asp His Thr Lys Lys Leu Ser Ile Pro Thr Thr Val Ser
            20                  25                  30

Arg Val Leu Lys Tyr Ile Pro Glu Leu Gln Lys Gln Val Asp Asn Leu
        35                  40                  45

Glu Arg Arg Lys Arg Glu Leu Thr Asn Ala Asn Cys Lys Pro Gly Val
    50                  55                  60

Leu Asn Thr Ser Glu Ile Val Thr Thr Pro Ile Val Ser Ala Thr Cys
65                  70                  75                  80

Leu Asn Asp Thr Glu Ile Met Val Gln Val Ser Leu His Ser Asn Val
                85                  90                  95

Ala Ala Thr Ala Leu Pro Leu Ser Lys Cys Ile Lys Val Leu Glu Asp
            100                 105                 110

Ala Gly Leu His Leu Ile Ser Ser Ser Thr Tyr Ser Thr Phe Gly Asn
        115                 120                 125

Lys Thr Phe Tyr Ser Leu His Leu Gln Val Cys Met His Val His Ser
    130                 135                 140

Met Val Pro Ala Val Ser Phe Asn Phe Phe Ile
145                 150                 155
```

<210> SEQ ID NO 106
<211> LENGTH: 37
<212> TYPE: DNA
<213> ORGANISM: Artificial Sequence
<220> FEATURE:
<223> OTHER INFORMATION: An Artificially Synthesized Primer Sequence

<400> SEQUENCE: 106
aaatctagaa tgtgtgcatt agtacctcca ttgtttc    37

<210> SEQ ID NO 107
<211> LENGTH: 40
<212> TYPE: DNA
<213> ORGANISM: Artificial Sequence
<220> FEATURE:
<223> OTHER INFORMATION: An Artificially Synthesized Primer Sequence

<400> SEQUENCE: 107
aaaggatcct catatatatg agtttccaca ttcctcatac    40

```
<210> SEQ ID NO 108
<211> LENGTH: 34
<212> TYPE: DNA
<213> ORGANISM: Artificial Sequence
<220> FEATURE:
<223> OTHER INFORMATION: An Artificially Synthesized Primer Sequence

<400> SEQUENCE: 108
aaatctagaa tggagtatcc atggctgcag tctc                              34

<210> SEQ ID NO 109
<211> LENGTH: 34
<212> TYPE: DNA
<213> ORGANISM: Artificial Sequence
<220> FEATURE:
<223> OTHER INFORMATION: An Artificially Synthesized Primer Sequence

<400> SEQUENCE: 109
aaaggatcct tatgattggc gtaatcccaa gagc                              34

<210> SEQ ID NO 110
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 110
acgtgtcgac cttagccaat ggatgaggat g                                 31

<210> SEQ ID NO 111
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 111
acgttctaga tttttgttta ctgtagaaga g                                 31

<210> SEQ ID NO 112
<211> LENGTH: 33
<212> TYPE: DNA
<213> ORGANISM: Artificial Sequence
<220> FEATURE:
<223> OTHER INFORMATION: An Artificially Synthesized Primer Sequence

<400> SEQUENCE: 112
acgtgtttaa acgcatagac tctcagcgga gag                               33

<210> SEQ ID NO 113
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 113
acgtgctagc gaaaactcct ggtgagagtg g                                 31

<210> SEQ ID NO 114
<211> LENGTH: 34
<212> TYPE: DNA
<213> ORGANISM: Artificial Sequence
<220> FEATURE:
<223> OTHER INFORMATION: An Artificially Synthesized Primer Sequence
```

```
<400> SEQUENCE: 114
acgtgctagc atgattgaac aagatggatt gcac                        34

<210> SEQ ID NO 115
<211> LENGTH: 30
<212> TYPE: DNA
<213> ORGANISM: Artificial Sequence
<220> FEATURE:
<223> OTHER INFORMATION: An Artificially Synthesized Primer Sequence

<400> SEQUENCE: 115
acgtgtcgac ctgcaggcat gcaagcttgg                             30

<210> SEQ ID NO 116
<211> LENGTH: 33
<212> TYPE: DNA
<213> ORGANISM: Artificial Sequence
<220> FEATURE:
<223> OTHER INFORMATION: An Artificially Synthesized Primer Sequence

<400> SEQUENCE: 116
acgtgtcgac ctctggatgc ctaaacaaac gac                         33

<210> SEQ ID NO 117
<211> LENGTH: 30
<212> TYPE: DNA
<213> ORGANISM: Artificial Sequence
<220> FEATURE:
<223> OTHER INFORMATION: An Artificially Synthesized Primer Sequence

<400> SEQUENCE: 117
acgttctaga ggcttttgtc ggtcggcctg                             30

<210> SEQ ID NO 118
<211> LENGTH: 30
<212> TYPE: DNA
<213> ORGANISM: Artificial Sequence
<220> FEATURE:
<223> OTHER INFORMATION: An Artificially Synthesized Primer Sequence

<400> SEQUENCE: 118
acgtgtcgac ggaggtgcag tttgcagcag                             30

<210> SEQ ID NO 119
<211> LENGTH: 33
<212> TYPE: DNA
<213> ORGANISM: Artificial Sequence
<220> FEATURE:
<223> OTHER INFORMATION: An Artificially Synthesized Primer Sequence

<400> SEQUENCE: 119
acgttctaga tatagagaga gggtgatcaa cga                         33

<210> SEQ ID NO 120
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 120
acgttctaga atggggcaca agcagctgtt c                           31
```

```
<210> SEQ ID NO 121
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 121
acgtggatcc tcactgatgc atatgcagtc c                                 31

<210> SEQ ID NO 122
<211> LENGTH: 258
<212> TYPE: PRT
<213> ORGANISM: Artificial Sequence
<220> FEATURE:
<223> OTHER INFORMATION: PROTEIN SEQUENCE OF AtbHLH39

<400> SEQUENCE: 122
```

Met Cys Ala Leu Val Pro Pro Leu Phe Pro Asn Phe Gly Trp Pro Ser
1               5                   10                  15

Thr Gly Glu Tyr Asp Ser Tyr Tyr Leu Ala Gly Asp Ile Leu Asn Asn
            20                  25                  30

Gly Gly Phe Leu Asp Phe Pro Val Pro Glu Glu Thr Tyr Gly Ala Val
        35                  40                  45

Thr Ala Val Thr Gln His Gln Asn Ser Phe Gly Val Ser Val Ser Ser
    50                  55                  60

Glu Gly Asn Glu Ile Asp Asn Asn Pro Val Val Lys Lys Leu Asn
65                  70                  75                  80

His Asn Ala Ser Glu Arg Asp Arg Arg Lys Ile Asn Ser Leu Phe
                85                  90                  95

Ser Ser Leu Arg Ser Cys Leu Pro Ala Ser Gly Gln Ser Lys Lys Leu
            100                 105                 110

Ser Ile Pro Ala Thr Val Ser Arg Ser Leu Lys Tyr Ile Pro Glu Leu
        115                 120                 125

Gln Glu Gln Val Lys Lys Leu Ile Lys Lys Glu Glu Leu Leu Val
130                 135                 140

Gln Ile Ser Gly Gln Arg Asn Thr Glu Cys Tyr Val Lys Gln Pro Pro
145                 150                 155                 160

Lys Ala Val Ala Asn Tyr Ile Ser Thr Val Ser Ala Thr Arg Leu Gly
                165                 170                 175

Asp Asn Glu Val Met Val Gln Ile Ser Ser Ser Lys Ile His Asn Phe
            180                 185                 190

Ser Ile Ser Asn Val Leu Ser Gly Leu Glu Glu Asp Arg Phe Val Leu
        195                 200                 205

Val Asp Met Ser Ser Ser Arg Ser Gln Gly Glu Arg Leu Phe Tyr Thr
    210                 215                 220

Leu His Leu Gln Val Glu Lys Ile Glu Asn Tyr Lys Leu Asn Cys Glu
225                 230                 235                 240

Glu Leu Ser Gln Arg Met Leu Tyr Leu Tyr Glu Glu Cys Gly Asn Ser
                245                 250                 255

Tyr Ile

```
<210> SEQ ID NO 123
<211> LENGTH: 253
<212> TYPE: PRT
<213> ORGANISM: Artificial Sequence
<220> FEATURE:
<223> OTHER INFORMATION: PROTEIN SEQUENCE OF AtbHLH38
```

<400> SEQUENCE: 123

Met Cys Ala Leu Val Pro Ser Phe Phe Thr Asn Phe Gly Trp Pro Ser
1               5                   10                  15

Thr Asn Gln Tyr Glu Ser Tyr Tyr Gly Ala Gly Asp Asn Leu Asn Asn
            20                  25                  30

Gly Thr Phe Leu Glu Leu Thr Val Pro Gln Thr Tyr Glu Val Thr His
        35                  40                  45

His Gln Asn Ser Leu Gly Val Ser Val Ser Ser Glu Gly Asn Glu Ile
    50                  55                  60

Asp Asn Asn Pro Val Val Lys Lys Leu Asn His Asn Ala Ser Glu
65                  70                  75                  80

Arg Asp Arg Arg Lys Lys Ile Asn Thr Leu Phe Ser Ser Leu Arg Ser
                85                  90                  95

Cys Leu Pro Ala Ser Asp Gln Ser Lys Lys Leu Ser Ile Pro Glu Thr
            100                 105                 110

Val Ser Lys Ser Leu Lys Tyr Ile Pro Glu Leu Gln Gln Gln Val Lys
        115                 120                 125

Arg Leu Ile Gln Lys Lys Glu Glu Ile Leu Val Arg Val Ser Gly Gln
    130                 135                 140

Arg Asp Phe Glu Leu Tyr Asp Lys Gln Gln Pro Lys Ala Val Ala Ser
145                 150                 155                 160

Tyr Leu Ser Thr Val Ser Ala Thr Arg Leu Gly Asp Asn Glu Val Met
                165                 170                 175

Val Gln Val Ser Ser Ser Lys Ile His Asn Phe Ser Ile Ser Asn Val
            180                 185                 190

Leu Gly Gly Ile Glu Glu Asp Gly Phe Val Leu Val Asp Val Ser Ser
        195                 200                 205

Ser Arg Ser Gln Gly Glu Arg Leu Phe Tyr Thr Leu His Leu Gln Val
    210                 215                 220

Glu Asn Met Asp Asp Tyr Lys Ile Asn Cys Glu Leu Ser Glu Arg
225                 230                 235                 240

Met Leu Tyr Leu Tyr Glu Lys Cys Glu Asn Ser Phe Asn
                245                 250

<210> SEQ ID NO 124
<211> LENGTH: 242
<212> TYPE: PRT
<213> ORGANISM: Artificial Sequence
<220> FEATURE:
<223> OTHER INFORMATION: PROTEIN SEQUENCE OF AtbHLH100

<400> SEQUENCE: 124

Met Cys Ala Leu Val Pro Pro Leu Tyr Pro Asn Phe Gly Trp Pro Cys
1               5                   10                  15

Gly Asp His Ser Phe Tyr Glu Thr Asp Asp Val Ser Asn Thr Phe Leu
            20                  25                  30

Asp Phe Pro Leu Pro Asp Leu Thr Val Thr His Glu Asn Val Ser Ser
        35                  40                  45

Glu Asn Asn Arg Thr Leu Leu Asp Asn Pro Val Val Met Lys Lys Leu
    50                  55                  60

Asn His Asn Ala Ser Glu Arg Glu Arg Arg Lys Lys Ile Asn Thr Met
65                  70                  75                  80

Phe Ser Ser Leu Arg Ser Cys Leu Pro Pro Thr Asn Gln Thr Lys Lys
                85                  90                  95

```
Leu Ser Val Ser Ala Thr Val Ser Gln Ala Leu Lys Tyr Ile Pro Glu
                100                 105                 110

Leu Gln Glu Gln Val Lys Lys Leu Met Lys Lys Glu Glu Leu Ser
            115                 120                 125

Phe Gln Ile Ser Gly Gln Arg Asp Leu Val Tyr Thr Asp Gln Asn Ser
        130                 135                 140

Lys Ser Glu Glu Gly Val Thr Ser Tyr Ala Ser Thr Val Ser Ser Thr
145                 150                 155                 160

Arg Leu Ser Glu Thr Glu Val Met Val Gln Ile Ser Ser Leu Gln Thr
                165                 170                 175

Glu Lys Cys Ser Phe Gly Asn Val Leu Ser Gly Val Glu Glu Asp Gly
            180                 185                 190

Leu Val Leu Val Gly Ala Ser Ser Arg Ser His Gly Glu Arg Leu
        195                 200                 205

Phe Tyr Ser Met His Leu Gln Ile Lys Asn Gly Gln Val Asn Ser Glu
210                 215                 220

Glu Leu Gly Asp Arg Leu Leu Tyr Leu Tyr Glu Lys Cys Gly His Ser
225                 230                 235                 240

Phe Thr

<210> SEQ ID NO 125
<211> LENGTH: 240
<212> TYPE: PRT
<213> ORGANISM: Artificial Sequence
<220> FEATURE:
<223> OTHER INFORMATION: PROTEIN SEQUENCE OF AtbHLH101

<400> SEQUENCE: 125

Met Glu Tyr Pro Trp Leu Gln Ser Gln Val His Ser Phe Ser Pro Thr
1               5                   10                  15

Leu His Phe Pro Ser Phe Leu His Pro Leu Asp Asp Ser Lys Ser His
            20                  25                  30

Asn Ile Asn Leu His His Met Ser Leu Ser His Ser Asn Asn Thr Asn
        35                  40                  45

Ser Asn Asn Asn Tyr Gln Glu Glu Asp Arg Gly Ala Val Val Leu
    50                  55                  60

Glu Lys Lys Leu Asn His Asn Ala Ser Glu Arg Asp Arg Arg Lys
65                  70                  75                  80

Leu Asn Ala Leu Tyr Ser Ser Leu Arg Ala Leu Leu Pro Leu Ser Asp
                85                  90                  95

Gln Lys Arg Lys Leu Ser Ile Pro Met Thr Val Ala Arg Val Val Lys
            100                 105                 110

Tyr Ile Pro Glu Gln Lys Gln Glu Leu Gln Arg Leu Ser Arg Arg Lys
        115                 120                 125

Glu Glu Leu Leu Lys Arg Ile Ser Arg Lys Thr His Gln Glu Gln Leu
130                 135                 140

Arg Asn Lys Ala Met Met Asp Ser Ile Asp Ser Ser Ser Ser Gln Arg
145                 150                 155                 160

Ile Ala Ala Asn Trp Leu Thr Asp Thr Glu Ile Ala Val Gln Ile Ala
                165                 170                 175

Thr Ser Lys Trp Thr Ser Val Ser Asp Met Leu Leu Arg Leu Glu Glu
            180                 185                 190

Asn Gly Leu Asn Val Ile Ser Val Ser Ser Val Ser Ser Thr Ala
        195                 200                 205
```

-continued

```
Arg Ile Phe Tyr Thr Leu His Leu Gln Met Arg Gly Asp Cys Lys Val
    210                 215                 220
Arg Leu Glu Glu Leu Ile Asn Gly Met Leu Leu Gly Leu Arg Gln Ser
225                 230                 235                 240
```